(12) United States Patent
Takahashi et al.

(10) Patent No.: US 9,260,436 B2
(45) Date of Patent: Feb. 16, 2016

(54) FUSED HETEROCYCLIC COMPOUND

(71) Applicant: Sumitomo Chemical Company, Limited, Tokyo (JP)

(72) Inventors: Masaki Takahashi, Takarazuka (JP); Mai Ito, Takarazuka (JP); Yoshihiko Nokura, Takarazuka (JP); Takamasa Tanabe, Takarazuka (JP); Chie Shimizu, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/409,079

(22) PCT Filed: Jun. 10, 2013

(86) PCT No.: PCT/JP2013/066525
§ 371 (c)(1),
(2) Date: Dec. 18, 2014

(87) PCT Pub. No.: WO2013/191112
PCT Pub. Date: Dec. 27, 2013

(65) Prior Publication Data
US 2015/0191474 A1    Jul. 9, 2015

(30) Foreign Application Priority Data
Jun. 22, 2012 (JP) ................ 2012-141029

(51) Int. Cl.
| | | |
|---|---|---|
| C07D 491/02 | (2006.01) | |
| A61K 31/50 | (2006.01) | |
| C07D 487/04 | (2006.01) | |
| A01N 43/54 | (2006.01) | |
| A01N 43/60 | (2006.01) | |
| A01N 43/90 | (2006.01) | |
| C07D 239/74 | (2006.01) | |
| C07D 239/86 | (2006.01) | |
| C07D 239/94 | (2006.01) | |
| C07D 241/42 | (2006.01) | |
| C07D 471/04 | (2006.01) | |
| A01N 47/02 | (2006.01) | |
| A61K 31/437 | (2006.01) | |
| A61K 31/498 | (2006.01) | |
| A61K 31/5025 | (2006.01) | |
| A61K 31/517 | (2006.01) | |
| A61K 31/519 | (2006.01) | |
| C07D 239/91 | (2006.01) | |

(52) U.S. Cl.
CPC .............. *C07D 487/04* (2013.01); *A01N 43/54* (2013.01); *A01N 43/60* (2013.01); *A01N 43/90* (2013.01); *A01N 47/02* (2013.01); *A61K 31/437* (2013.01); *A61K 31/498* (2013.01); *A61K 31/5025* (2013.01); *A61K 31/517* (2013.01); *A61K 31/519* (2013.01); *C07D 239/74* (2013.01); *C07D 239/86* (2013.01); *C07D 239/91* (2013.01); *C07D 239/94* (2013.01); *C07D 241/42* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 6,429,205 | B1 | 8/2002 | Jacobson et al. |
| 2002/0068744 | A1 | 6/2002 | Schmitt et al. |
| 2003/0096820 | A1 | 5/2003 | Jacobson et al. |
| 2004/0248890 | A1 | 12/2004 | Gonzalez et al. |

(Continued)

FOREIGN PATENT DOCUMENTS

| | | |
|---|---|---|
| JP | 2008-308448 A | 12/2008 |
| WO | 2011090127 A1 | 7/2011 |
| WO | 2013085339 A2 | 6/2013 |

OTHER PUBLICATIONS

Int'l Search Report issued Aug. 20, 2013 in Int'l Application No. PCT/JP2013/066525.

(Continued)

*Primary Examiner* — Heidi Reese
(74) *Attorney, Agent, or Firm* — Panitch Schwarze Belisario & Nadel LLP

(57) ABSTRACT

The fused heterocyclic compound represented by formula (1) has excellent effectiveness in pest control.

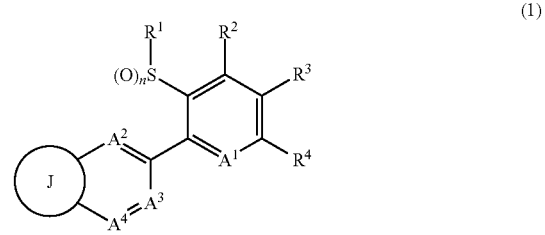

(1)

In the formula (1), J represents formula J1, J2, J3, J4, J5 or J6; $A^1$; $A^2$; $A^3$; $A^4$; $A^5$; $B^1$; $B^2$; $B^4$; $B^5$; and $B^6$ each represent a nitrogen atom, etc.; $B^3$ represents $NR^5$, etc.; $R^1$ represents a C1-C6 chain hydrocarbon group, etc., optionally having one or more atoms or groups selected from group X; the pairs $R^2$ and $R^3$ and $R^5$ and $R^6$ are the same or different, and represent a C1-C6 chain hydrocarbon group, etc., optionally having one or more atoms or groups selected from group X; $R^4$ represents a C1-C6 chain hydrocarbon group, etc., optionally having one or more atoms or groups selected from group W; and n represents 0, 1, or 2.

7 Claims, No Drawings

(56) References Cited

U.S. PATENT DOCUMENTS

| | | |
|---|---|---|
| 2006/0217377 A1 | 9/2006 | Gonzalez et al. |
| 2008/0146637 A1 | 6/2008 | Cheung et al. |
| 2008/0227796 A1 | 9/2008 | Wagner et al. |
| 2010/0160316 A1 | 6/2010 | Gonzalez, III et al. |
| 2011/0021495 A1 | 1/2011 | Gonzalez, III et al. |

OTHER PUBLICATIONS

Sharghi et al, "Tluorothiophenols and Their Derivatives," Journal of Chemical and Engineering Data, vol. 8, pp. 276-278 (1963).

FUSED HETEROCYCLIC COMPOUND

CROSS-REFERENCE TO RELATED APPLICATION

This application is a Section 371 of International Application No. PCT/JP2013/066525, filed Jun. 10, 2013, which was published in the Japanese language on Dec. 27, 2013, under International Publication No. WO 2013/191112 A1, and the disclosure of which is incorporated herein by reference.

TECHNICAL FIELD

The present invention relates to a certain type of a fused heterocyclic compound and a use thereof for pest control.

BACKGROUND ART

Various fused heterocyclic compounds are known in USP-7612211, WO2006/066818, Journal of Chemical and Engineering Data, 8, 276 (1963), and the like.

SUMMARY OF THE INVENTION

The present invention provides a compound having an excellent control effect on pests and a method for controlling pests using the compound.

The present invention is as described below.

[1]

A fused heterocyclic compound represented by formula (1):

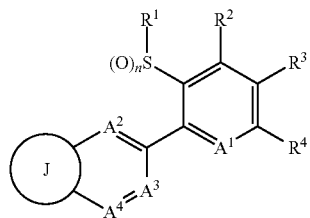

(1)

[wherein
J represents the following formula J1, J2, J3, J4, J5 or J6,

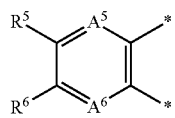
J1

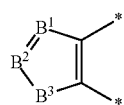
J2

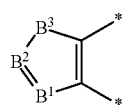
J3

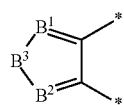
J4

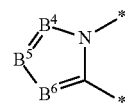
J5

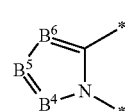
J6

$A^1$ represents a nitrogen atom or $CR^7$,
$A^2$ represents a nitrogen atom or $CR^8$,
$A^3$ represents a nitrogen atom or $CR^9$,
$A^4$ represents a nitrogen atom or $CR^{10}$,
$A^5$ represents a nitrogen atom or $CR^{11}$,
$A^6$ represents a nitrogen atom or $CR^{12}$, (wherein when J is J1, at least one of $A^2$, $A^3$, $A^4$, $A^5$ and $A^6$ represents a nitrogen atom),
$B^1$ represents a nitrogen atom or $CR^{13}$,
$B^2$ represents a nitrogen atom or $CR^{14}$ (wherein $B^1$ and $B^2$ do not represent a nitrogen atom at the same time),
$B^3$ represents $NR^{15}$, an oxygen atom or a sulfur atom,
$B^4$ represents a nitrogen atom or $CR^{16}$,
$B^5$ represents a nitrogen atom or $CR^{17}$,
$B^6$ represents a nitrogen atom or $CR^{18}$ (wherein all of $B^4$, $B^5$ and $B^6$ do not represent a nitrogen atom at the same time),
$R^1$ represents a C1 to C6 chain hydrocarbon group optionally having one or more atoms or groups selected from group X or a C3 to C6 alicyclic hydrocarbon group optionally having one or more atoms or groups selected from group Y,
$R^2$, $R^3$ and $R^7$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, —$OR^{19}$, —$S(O)_mR^{19}$, —$S(O)_2NR^{19}R^{20}$, —$NR^{19}R^{20}$, —$NR^{19}CO_2R^{20}$, —$NR^{19}C(O)R^{20}$, —$CO_2R^{19}$, —$C(O)R^{19}$, —$C(O)NR^{19}R^{20}$, —$SF_5$, a cyano group, a nitro group, a halogen atom or a hydrogen atom,
$R^4$ represents a C1 to C6 chain hydrocarbon group optionally having one or more atoms or groups selected from group W, a phenyl group optionally having one or more atoms or groups selected from group Z, a 5- or 6-membered heterocyclic group optionally having one or more atoms or groups selected from group Z, —$OR^{19}$, —$S(O)_mR^{19}$, —$S(O)_2NR^{19}R^{20}$, —$NR^{19}R^{20}$, —$NR^{19}CO_2R^{20}$, —$NR^{19}C(O)R^{20}$, —$CO_2R^{19}$, —$C(O)R^{19}$, —$C(O)NR^{19}R^{20}$, —$SF_5$, a cyano group, a nitro group, a halogen atom or a hydrogen atom,
$R^5$ and $R^6$ are the same or different and represent a C1 to C6 chain hydrocarbon group optionally having one or more atoms or groups selected from group X, a phenyl group optionally having one or more atoms or groups selected from group Z, a 5-membered heterocyclic group optionally having one or more atoms or groups selected from group Z, a 6-aromatic membered heterocyclic group optionally having one or more atoms or groups selected from group Z, —$OR^{21}$, —$S(O)_mR^{21}$, —$S(O)_2R^{21}R^{22}$, —$NR^{21}R^{22}$, —$NR^{21}CO_2R^{22}$, —$NR^{21}C(O)R^{22}$, —$CO_2R^{21}$, —$C(O)R^{21}$, —$C(O)NR^{21}R^{22}$, —$SF_5$, a cyano group, a nitro group, a halogen atom or a hydrogen atom (wherein $R^5$ and $R^6$ do not represent a hydrogen atom at the same time),
$R^8$, $R^9$ and $R^{10}$ are the same or different and represent a C1 to C6 chain hydrocarbon group optionally having one or more atoms or groups selected from group X, —OR$^{23}$, —S(O)$_m$R$^{24}$, —S(O)$_2$NR$^{24}$R$^{25}$, —NR$^{24}$R$^{25}$, —NR$^{24}$CO$_2$R$^{25}$, —NR$^{24}$C(O)R$^{25}$, —CO$_2$R$^{23}$, —C(O)R$^{24}$, —C(O)NR$^{24}$R$^{25}$, —SF$_5$, a cyano group, a nitro group, a halogen atom or a hydrogen atom, R$^{11}$ and R$^{12}$ represent a C1 to C6 chain hydrocarbon group optionally having one or more halogen atoms, —OR$^{21}$, —S(O)$_m$R$^{21}$, —NR$^{21}$R$^{22}$, —CO$_2$R$^{21}$, —C(O)R$^{21}$, a cyano group, a nitro group, a halogen atom or a hydrogen atom, R$^{13}$, R$^{14}$, R$^{16}$, R$^{17}$ and R$^{18}$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, —OR$^{26}$, —S(O)$_m$R$^{26}$, —S(O)$_2$NR$^{26}$R$^{27}$, —NR$^{26}$R$^{27}$, —NR$^{26}$CO$_2$R$^{27}$, —NR$^{28}$C(O)R$^{29}$, —CO$_2$R$^{26}$, —C(O)R$^{26}$, —C(O)NR$^{26}$R$^{27}$, —SF$_5$, a cyano group, a nitro group, a halogen atom or a hydrogen atom (wherein at least one of R$^{16}$, R$^{17}$ and R$^{18}$ represents other than a hydrogen atom), R$^{15}$ represents a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, —CO$_2$R$^{26}$, —C(O)R$^{26}$, a C3 to C6 alicyclic hydrocarbon group optionally having one or more atoms or groups selected from group Y or a hydrogen atom, R$^{19}$, R$^{20}$, R$^{21}$, R$^{22}$, R$^{24}$, R$^{25}$, R$^{26}$ and R$^{27}$ are the same or different and represent a C1 to C6 chain hydrocarbon group optionally having one or more atoms or groups selected from group X or a hydrogen atom, R$^{23}$, R$^{28}$ and R$^{29}$ are the same or different and represent a C1 to C6 chain hydrocarbon group optionally having one or more atoms or groups selected from group X, m each independently represents 0, 1 or 2, and n represents 0, 1 or 2;

wherein B$^2$ does not represent C(CH$_2$Br), and when m is 1 or 2 in —S(O)$_m$R$^{19}$, R$^{19}$ does not represent a hydrogen atom, when m is 1 or 2 in —S(O)$_m$R$^{21}$, R$^{21}$ does not represent a hydrogen atom, when m is 1 or 2 in —S(O)$_m$R$^{24}$, R$^{24}$ does not represent a hydrogen atom, and when m is 1 or 2 in —S(O)$_m$R$^{26}$, R$^{26}$ does not represent a hydrogen atom;

Also, when A$^1$ and A$^5$ are CH, A$^2$ is nitrogen atom, A$^3$ is CR$^9$, A$^4$ is CCl or CH, A$^6$ is a nitrogen atom, CF or CH, and R$^5$ is a fluorine atom, R$^1$ does not represent a methyl group;

Also, when A$^1$, A$^5$ and A$^6$ are CH, A$^2$ and A$^3$ are a nitrogen atom, and R$^6$ is a chlorine atom, A$^4$ does not represent CN(CH$_3$)$_2$;

Group X: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms, Group Y: a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms, Group Z: a group consisting of C1 to C6 chain hydrocarbon groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C1 to C6 alkylamino groups optionally having one or more halogen atoms, C2 to C8 dialkylamino groups optionally having one or more halogen atoms, halogen atoms, cyano groups, nitro groups, and SF$_5$, Group W: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C3 to C6 cycloalkyl groups optionally having one or more halogen atoms or one or more C1 to C3 alkyl groups, cyano groups, hydroxy groups, and halogen atoms.] or an N-oxide thereof.

[2]

The compound according to [1], wherein

R$^1$ is a C1 to C6 alkyl group optionally having one or more atoms or groups selected from halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a cyclopropyl group optionally having one or more halogen atoms or one or more C1 to C3 alkyl groups, R$^2$, R$^4$ and R$^7$ are the same or different and are a halogen atom or a hydrogen atom, R$^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered aromatic heterocyclic group (wherein the 5- or 6-membered aromatic heterocyclic group optionally has one or more atoms or groups selected from the group consisting of halogen atoms, C1 to C3 alkyl groups optionally having a halogen atom, and C1 to C3 alkoxy groups optionally having a halogen atom), —OR$^{19}$ (wherein R$^{19}$ is a C1 to C6 alkyl group optionally having one or more halogen atoms), —S(O)$_m$R$^{19}$ (wherein R$^{19}$ is a C1 to C6 alkyl group optionally having one or more halogen atoms, and m is 0, 1 or 2), —SF$_5$, a cyano group, a nitro group, a halogen atom or a hydrogen atom, one of R$^5$ and R$^6$ is a C1 to C6 alkyl group optionally having one or more halogen atoms, —OR$^{21}$ (wherein R$^{21}$ is a C1 to C6 alkyl group optionally having one or more halogen atoms), —S(O)$_m$R$^{21}$ (wherein R$^{21}$ is a C1 to C6 alkyl group optionally having one or more halogen atoms, and m is 0, 1 or 2), —SF$_5$ or a halogen atom, and the other is a halogen atom or a hydrogen atom, R$^8$, R$^9$ and R$^{10}$ are the same or different and are a C1 to C6 alkyl group optionally having one or more halogen atoms, —NR$^{24}$R$^{25}$ (wherein R$^{24}$ and R$^{25}$ are the same or different and are a C1 to C6 alkyl group optionally having one or more halogen atoms or a hydrogen atom), a halogen atom or a hydrogen atom, $R^{11}$ and $R^{12}$ are the same or different and are a halogen atom or a hydrogen atom, $R^{13}$ and $R^{14}$ are the same or different and are a C1 to C6 alkyl group optionally having one or more halogen atoms, —$OR^{26}$ (wherein $R^{26}$ is a C1 to C6 alkyl group optionally having one or more halogen atoms), —$S(O)_m R^{26}$ (wherein $R^{26}$ is a C1 to C6 alkyl group optionally having one or more halogen atoms, and m is 0, 1 or 2), —$SF_5$, a halogen atom or a hydrogen atom, $R^{15}$ is a C1 to C6 alkyl group optionally having one or more halogen atoms, a C3 to C6 alkenyl group optionally having one or more halogen atoms, a C3 to C6 alkynyl group optionally having one or more halogen atoms, a C1 to C3 alkyl group having a C1 to C3 alkoxy group optionally having one or more halogen atoms, —$CO_2 R^{26}$ (wherein $R^{26}$ is a C1 to C6 alkyl group optionally having one or more halogen atoms), —$C(O)R^{26}$ (wherein $R^{26}$ is a C1 to C6 alkyl group optionally having one or more halogen atoms) or a hydrogen atom, one of $R^{16}$, $R^{17}$ and $R^{18}$ is a C1 to C6 alkyl group optionally having one or more halogen atoms, —$OR^{26}$ (wherein $R^{26}$ is a C1 to C6 alkyl group optionally having one or more halogen atoms), —$S(O)_m R^{26}$ (wherein $R^{26}$ is a C1 to C6 alkyl group optionally having one or more halogen atoms, and m is 0, 1 or 2), —$SF_5$ or a halogen atom, and the rest are the same or different and each a halogen atom or a hydrogen atom.

[3]
The compound according to [1] or [2],
wherein
$R^1$ is an ethyl group, a cyclopropyl group or a cyclopropylmethyl group,
$R^2$, $R^4$ and $R^7$ are a hydrogen atom,
$R^3$ is a C1 to C6 alkyl group optionally having one or more halogen atoms, —$OR^{19}$ (wherein $R^{19}$ is a C1 to C6 alkyl group optionally having one or more halogen atoms), —$S(O)_m R^9$ (wherein $R^{19}$ is a C1 to C6 alkyl group optionally having one or more halogen atoms, and m is 0, 1 or 2), a halogen atom or a hydrogen atom,
one of $R^5$ and $R^6$ is a C1 to C6 haloalkyl group, —$OR^{21}$ (wherein $R^{21}$ is a C1 to C6 haloalkyl group), —$S(O)_m R^{21}$ (wherein $R^{21}$ is a C1 to C6 haloalkyl group, and m is 0, 1 or 2), or a halogen atom, and the other is a halogen atom or a hydrogen atom,
$R^8$, $R^9$ and $R^{10}$ are the same or different and are a methyl group, a halogen atom or a hydrogen atom,
$R^{11}$ and $R^{12}$ are a hydrogen atom,
$R^{15}$ is a C1 to C6 alkyl group optionally having one or more halogen atoms or a hydrogen atom,
one of $R^{16}$, $R^{17}$ and $R^{18}$ is a C1 to C6 haloalkyl group, —$OR^{26}$ (wherein $R^{26}$ is a C1 to C6 haloalkyl group), —$S(O)_m R^{26}$ (wherein $R^{26}$ is a C1 to C6 haloalkyl group, and m is 0, 1 or 2), or a halogen atom, and the rest are the same or different and each a halogen atom or a hydrogen atom.

[4]
The compound according to [1] to [3], wherein J is J1.

[5]
The compound according to any one of [1] to [3], wherein J is J2, J3, or J4.

[6]
The compound according to any one of [1] to [3], wherein J is J5 or J6.

[7]
The compound according to any one of [1] to [3], wherein J is J2 or J3, $B^1$ is a nitrogen atom, and $B^2$ is $CR^{14}$.

[8]
The compound according to any one of [1] to [3], wherein J is J2, J3 or J4, $B^1$ is a nitrogen atom, $B^2$ is $CR^{14}$, and $B^3$ is $NR^{15}$.

[9]
The compound according to any one of [1] to [3], wherein J is J5 or J6, $B^4$ is $CR^{16}$, $B^5$ is $CR^{17}$, and $B^6$ is a nitrogen atom.

[10]
The compound according to any one of [1] to [3], wherein

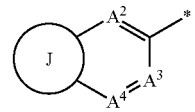

in the formula (1) is any of the following J1-1 to J1-5.

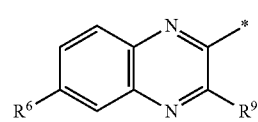

J1-1

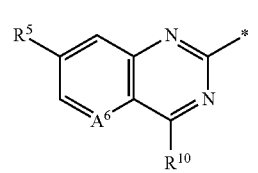

J1-2

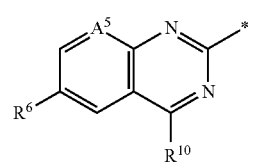

J1-3

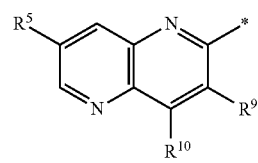

J1-4

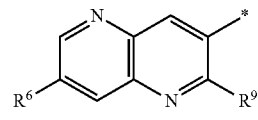

J1-5

[11]
The compound according to any one of [1] to [3], wherein

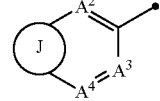

in the formula (1) is the following J2-1.

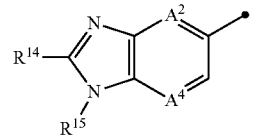

J2-1

-continued

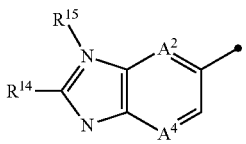
J3-1

[12]
The compound according to any one of [1] to [3], wherein

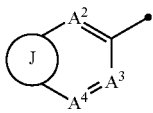

in the formula (1) is the following J5-1 or J6-1.

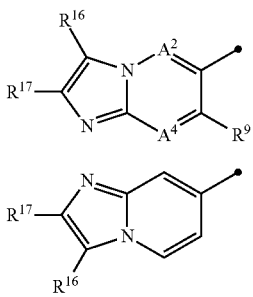
J5-1

J6-1

[13]
A pest control composition comprising the compound as defined in any one of [1] to [12], and an inert carrier.

[14]
A method for controlling pests comprising applying an effective amount of the compound as defined in any one of [1] to [12] to a pest or a pest-infested area.

MODE FOR CARRYING OUT THE INVENTION

In the compound of the present invention, an N-oxide is a compound in which the nitrogen atom constituting the ring on the heterocyclic group is oxidized. Examples of the heterocyclic group that may form an N-oxide include a pyridine ring, fused rings containing a pyridine ring, and the like.

The groups used in the description of the present specification will be described below with examples.

The notation of "Ca to Cb chain hydrocarbon group" in the present specification represents a straight-chain or branched-chain saturated or unsaturated hydrocarbon group having the number of carbon atoms of a to b.

Examples of the "C1 to C6 chain hydrocarbon group" include C1 to C6 alkyl groups such as a methyl group, an ethyl group, a propyl group, an isopropyl group, a butyl group, an isobutyl group, a sec-butyl group, a tert-butyl group, a pentyl group, a neopentyl group and a hexyl group; C2 to C6 alkenyl groups such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group and a 1-hexenyl group; and C2 to C6 alkynyl groups such as an ethynyl group, a propargyl group, a 2-butynyl group, a 3-butynyl group, a 1-pentynyl group and a 1-hexynyl group.

The notation of "Ca to Cb alkyl group" in the present specification represents a straight-chain or branched-chain hydrocarbon group having the number of carbon atoms of a to b.

Examples of the "C1 to C6 alkyl group" include a methyl group, an ethyl group, a propyl group, an isopropyl group, a butyl group, an isobutyl group, a sec-butyl group, a tert-butyl group, a pentyl group, a neopentyl group, and a hexyl group.

Examples of the "C2 to C6 alkyl group" include an ethyl group, a propyl group, an isopropyl group, a butyl group, an isobutyl group, a sec-butyl group, a tert-butyl group, a pentyl group, a neopentyl group, and a hexyl group.

Examples of the "C1 to C3 alkyl group" include a methyl group, an ethyl group, a propyl group, and an isopropyl group.

The notation of "Ca to Cb alkenyl group" in the present specification represents a straight-chain or branched-chain unsaturated hydrocarbon group having the number of carbon atoms of a to b, and having one or two or more double bonds in the molecule.

Examples of the "C2 to C6 alkenyl group" include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

The notation of "Ca to Cb alkynyl group" in the present specification represents a straight-chain or branched-chain unsaturated hydrocarbon group having the number of carbon atoms of a to b, and having one or two or more triple bonds in the molecule.

Examples of the "C2 to C6 alkynyl group" include an ethynyl group, a propargyl group, a 2-butynyl group, a 3-butynyl group, a 1-pentynyl group, and a 1-hexynyl group.

The notation of "Ca to Cb haloalkyl group" in the present specification represents a straight-chain or branched-chain hydrocarbon group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, a heptafluoroisopropyl group, and a nonafluorobutyl group.

Examples of the "C1 to C3 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

The notation of "Ca to Cb perfluoroalkyl group" in the present specification represents a straight or branched alkyl group having the number of carbon atoms of a to b, in which all hydrogen atoms bound to the carbon atom are substituted by a fluorine atom.

Examples of the "C1 to C6 perfluoroalkyl group" include a trifluoromethyl group, a pentafluoroethyl group, a heptafluoropropyl group, a heptafluoroisopropyl group, and a nonafluorobutyl group.

Examples of the "C1 to C3 perfluoroalkyl group" include a trifluoromethyl group, a pentafluoroethyl group, a heptafluoropropyl group, and a heptafluoroisopropyl group.

The notation of "Ca to Cb alkoxy group" in the present specification represents a group represented by a straight-chain or branched-chain alkyl —O— having the number of carbon atoms of a to b.

Examples of the "C1 to C6 alkoxy group" include a methoxy group, an ethoxy group, a propoxy group, an isopropoxy group, a butoxy group, an isobutoxy group, a sec-butoxy group, a tert-butoxy group, a pentyloxy group, a neopentyloxy group, and a hexyloxy group.

Examples of the "C1 to C3 alkoxy group" include a methoxy group, an ethoxy group, a propoxy group, and an isopropyloxy group.

The notation of "Ca to Cb alkenyloxy group" in the present specification represents a group represented by a straight-chain or branched-chain alkenyl —O— having the number of carbon atoms of a to b, and having one or two or more double bonds in the molecule.

Examples of the "C2 to C6 alkenyloxy group" include a vinyloxy group, a 1-propenyloxy group, a 2-propenyloxy group, a 1-methylvinyloxy group, a 2-methyl-1-propenyloxy group, a 1-butenyloxy group, a 2-butenyloxy group, a 3-butenyloxy group, a 1-pentenyloxy group, and a 1-hexenyloxy group.

The notation of "Ca to Cb alkynyloxy group" in the present specification represents a straight-chain or branched-chain alkynyl —O— having the number of carbon atoms of a to b, and having one or two or more triple bonds in the molecule.

Examples of the "C2 to C6 alkynyloxy group" include an ethynyloxy group, a propargyloxy group, a 2-butynyloxy group, a 3-butynyloxy group, a 1-pentynyloxy group, and a 1-hexynyloxy group.

The notation of "Ca to Cb alkylsulfanyl group" in the present specification represents a straight-chain or branched-chain alkyl —S— having the number of carbon atoms of a to b.

Examples of the "C1 to C6 alkylsulfanyl group" include a methylsulfanyl group, an ethylsulfanyl group, a propylsulfanyl group, an isopropylsulfanyl group, a butylsulfanyl group, a pentylsulfanyl group, and a hexylsulfanyl group.

The notation of "Ca to Cb alkylsulfinyl group" in the present specification represents a straight-chain or branched-chain alkyl —S(O)— having the number of carbon atoms of a to b.

Examples of the "C1 to C6 alkylsulfinyl group" include a methylsulfinyl group, an ethylsulfinyl group, a propylsulfinyl group, an isopropylsulfinyl group, a butylsulfinyl group, a pentylsulfinyl group, and a hexylsulfinyl group.

The notation of "Ca to Cb alkylsulfonyl group" in the present specification represents a straight-chain or branched-chain alkyl —S(O)$_2$— having the number of carbon atoms of a to b.

Examples of the "C1 to C6 alkylsulfonyl group" include a methylsulfonyl group, an ethylsulfonyl group, a propylsulfonyl group, an isopropylsulfonyl group, a butylsulfonyl group, a pentylsulfonyl group, and a hexylsulfonyl group.

The notation of "Ca to Cb alkylcarbonyl group" in the present specification represents a straight-chain or branched-chain alkyl —C(O)— having the number of carbon atoms of a to b.

Examples of the "C2 to C6 alkylcarbonyl group" include an acetyl group, a propionyl group, a butyryl group, a pentanoyl group, and a hexanoyl group.

The notation of "Ca to Cb alkoxycarbonyl group" in the present specification represents a straight-chain or branched-chain alkyl —O—C(O)— having the number of carbon atoms of a to b.

Examples of the "C2 to C6 alkoxycarbonyl group" include a methoxycarbonyl group, an ethoxycarbonyl group, a propoxycarbonyl group, a butoxycarbonyl group, a pentyloxycarbonyl group, and a tert-butoxycarbonyl group.

The notation of "Ca to Cb alicyclic hydrocarbon group" in the present specification represents a cyclic nonaromatic hydrocarbon group having the number of carbon atoms of a to b.

Examples of the "C3 to C6 alicyclic hydrocarbon group" include a cyclopropyl group, a cyclobutyl group, a cyclopentyl group, a cyclohexyl group, a 1-cyclohexenyl group, a 2-cyclohexenyl group, and a 3-cyclohexenyl group.

The notation of "Ca to Cb cycloalkyl group" in the present specification represents a cyclic alkyl group having the number of carbon atoms of a to b.

The "C3 to C6 cycloalkyl group" includes a cyclopropyl group, a cyclobutyl group, a cyclopentyl group, and a cyclohexyl group.

The notation of "Ca to Cb alkylamino group" in the present specification represents a straight-chain or branched-chain alkyl —NH— having the number of carbon atoms of a to b.

Examples of the "C1 to C6 alkylamino group" include a methylamino group, an ethylamino group, a propylamino group, an isopropylamino group, and a butylamino group.

The notation of "Ca to Cb dialkylamino group" in the present specification represents a straight-chain or branched-chain dialkylamino group having a total number of carbon atoms of each alkyl group of a to b, in which the number of carbon atoms of each alkyl group may be the same or different.

Examples of the "C2 to C8 dialkylamino group" include a dimethylamino group, a diethylamino group, and a dipropylamino group.

In the notation of "optionally having one or more atoms or groups selected from group X" in the present specification, when having two or more atoms or groups selected from group X, the atoms or groups selected from the group X may be the same or different from each other.

In the notation of "optionally having one or more atoms or groups selected from group Y" in the present specification, when having two or more atoms or groups selected from group Y, the atoms or groups selected from the group Y may be the same or different from each other.

In the notation of "optionally having one or more atoms or groups selected from group Z" in the present specification, when having two or more atoms or groups selected from group Z, the atoms or groups selected from the group Z may be the same or different from each other.

In the notation of "optionally having one or more atoms or groups selected from group W" in the present specification, when having two or more atoms or groups selected from group W, the atoms or groups selected from the group W may be the same or different from each other.

In the notation of "optionally having one or more halogen atoms" in the present specification, when having two or more halogen atoms, those halogen atoms may be the same or different from each other.

The notation of "heterocyclic group" in the present specification represents a heterocyclic compound residue containing one or more atoms selected from the group consisting of a nitrogen atom, an oxygen atom and a sulfur atom, other than a carbon atom, in the cyclic structure, and examples include a 5-membered heterocyclic group and a 6-membered heterocyclic group.

The "5-membered heterocyclic group" represents a 5-membered heterocyclic compound residue containing one or more atoms selected from the group consisting of a nitrogen atom, an oxygen atom and a sulfur atom, other than a carbon atom, in the cyclic structure, and examples include a 5-membered aromatic heterocyclic group and a 5-membered nonaromatic heterocyclic group.

Examples of the "5-membered aromatic heterocyclic group" include a pyrrolyl group, a furyl group, a pyrazolyl group, a thienyl group, an imidazolyl group, a triazolyl group, a tetrazolyl group, and an isoxazolyl group.

Examples of the "5-membered nonaromatic heterocyclic group" include a pyrrolidinyl group, a pyrazolidinyl group, and a tetrahydrofuryl group.

The "6-membered heterocyclic group" represents a 6-membered heterocyclic compound residue containing one or more atoms selected from the group consisting of a nitrogen atom, an oxygen atom and a sulfur atom, other than a carbon atom, in the cyclic structure, and examples include a 6-membered aromatic heterocyclic group and a 6-membered nonaromatic heterocyclic group.

Examples of the "6-membered aromatic heterocyclic group" include a pyrazinyl group, a pyrimidinyl group, and a pyridyl group.

Examples of the "6-membered nonaromatic heterocyclic group" include a piperidyl group, a morpholinyl group, a piperazinyl group, and a thiomorpholinyl group.

The "halogen atom" in the compound of the present invention refers to a fluorine atom, a chlorine atom, a bromine atom, and an iodine atom.

The notation of the "C1 to C6 chain hydrocarbon group optionally having one or more atoms or groups selected from group X" in the compound of the present invention represents a straight-chain or branched-chain hydrocarbon group comprising a carbon atom number of 1 to 6, in which a hydrogen atom bound to the carbon atom is optionally substituted by an atom or group selected from group X, and at that time, when having two or more atoms or groups selected from group X, the atoms or groups selected from group X may be the same or different from each other.

Examples of the "C1 to C6 chain hydrocarbon group optionally having one or more atoms or groups selected from group X" include C1 to C1 alkyl groups optionally having one or more atoms or groups selected from group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2-trifluoroethyl group, a pentafluoroethyl group, a methylsulfanylethyl group, an ethylsulfanylethyl group, a methylsulfinylethyl group, a methylsulfonylethyl group, a 2-hydroxyethyl group, a cyclopropylmethyl group, a 1-methylcyclopropylmethyl group, and a 2,2-difluorocyclopropylmethyl group; C2 to C6 alkenyl groups optionally having one or more atoms or groups selected from group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group X such as an ethynyl group, a propargyl group, a 2-butynyl group, a 3-butynyl group, a 1-pentynyl group, a 1-hexynyl group, a 4,4,4-trifluoro-2-butynyl group, and the C1 to C6 chain hydrocarbon group optionally having one or more atoms or groups selected from group X is selected in the range of each specified number of carbon atoms.

The notation of the "C3 to C6 alicyclic hydrocarbon group optionally having one or more atoms or groups selected from group Y" in the compound of the present invention represents a cyclic nonaromatic hydrocarbon group comprising a carbon atom number of 3 to 6, in which a hydrogen atom bound to the carbon atom is optionally substituted by an atom or group selected from group Y, and at that time, when having two or more atoms or groups selected from group Y, the atoms or groups selected from group Y may be the same or different from each other.

Examples of the "C3 to C6 alicyclic hydrocarbon group optionally having one or more atoms or groups selected from group Y" include a cyclopropyl group, a 2,2-difluorocyclopropyl group, a 2-methylcyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxylcyclohexyl group, a 3-methoxylcyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

The notation of the "C1 to C6 chain hydrocarbon group optionally having one or more halogen atoms" in the compound of the present invention represents a straight-chain or branched-chain hydrocarbon group comprising a carbon atom number of 1 to 6, in which a hydrogen atom bound to the carbon atom is optionally substituted by a halogen atom, and at that time, when having two or more halogen atoms, those halogen atoms may be the same or different from each other.

Examples of the "C1 to C6 chain hydrocarbon group optionally having one or more halogen atoms" include C1 to C6 alkyl groups optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group and a heptafluoroisopropyl group; C2 to C6 alkenyl groups optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more halogen atoms such as an ethynyl group, a propargyl group, a 2-butynyl group, a 3-butynyl group, a 1-pentynyl group, a 1-hexynyl group and a 4,4,4-trifluoro-2-butynyl group, and the C1 to C6 chain hydrocarbon group optionally having one or more halogen atoms is selected in the range of each specified number of carbon atoms.

The notation of the "phenyl group optionally having one or more atoms or groups selected from group Z" in the compound of the present invention represents a phenyl group in which a hydrogen atom bound to the carbon atom is optionally substituted by an atom or group selected from group Z, and at that time, when having two or more atoms or groups selected from group Z, the atoms or groups selected from group Z may be the same or different from each other.

Examples of the "phenyl group optionally having one or more atoms or groups selected from group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

The notation of the "heterocyclic group" in the "5- or 6-membered heterocyclic group optionally having one or more atoms or groups selected from group Z" in the compound of the present invention represents a heterocyclic compound residue containing one or more atoms selected from the group consisting of a nitrogen atom, an oxygen atom and a sulfur atom, other than a carbon atom, in the cyclic structure, and at that time, when having two or more atoms or groups selected from group Z, the atoms or groups selected from group Z may be the same or different from each other.

In addition, in the compound of the present invention, a 5- or 6-membered heterocyclic group means a 5- or 6-membered aromatic heterocyclic group or a 5- or 6-membered nonaromatic heterocyclic group.

Examples of the "5- or 6-membered heterocyclic group optionally having one or more atoms or groups selected from group Z" include 5- or 6-membered nonaromatic heterocyclic groups optionally having one or more atoms or groups selected from group Z such as a pyrrolidin-1-yl group, a 3,3,4,4-tetrafluoropyrrolidin-1-yl group, a tetrahydrofuran-2-yl group, a piperidyl group, a morpholinyl group and a thiomorpholinyl group; and 5- or 6-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

The notation of the "C1 to C6 chain hydrocarbon group optionally having one or more atoms or groups selected from group W" in the compound of the present invention represents a straight-chain or branched-chain hydrocarbon group comprising a carbon atom number of 1 to 6, in which a hydrogen atom bound to the carbon atom is optionally substituted by an atom or group selected from group W, and at that time, when having two or more atoms or groups selected from group W, the atoms or groups selected from group W may be the same or different from each other.

Examples of the "C1 to C6 chain hydrocarbon group optionally having one or more atoms or groups selected from group W" include C1 to C6 alkyl groups optionally having one or more atoms or groups selected from group W such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2-trifluoroethyl group, a pentafluoroethyl group, a methylsulfanylethyl group, an ethylsulfanylethyl group, a methylsulfinylethyl group, a methylsulfonylethyl group, a 2-hydroxyethyl group, a cyclopropylmethyl group, a 1-methylcyclopropylmethyl group, and a 2,2-difluorocyclopropylmethyl group; C2 to C6 alkenyl groups optionally having one or more atoms or groups selected from group W such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group W such as an ethynyl group, a propargyl group, a 2-butynyl group, a 3-butynyl group, a 1-pentynyl group, a 1-hexynyl group, a 4,4,4-trifluoro-2-butynyl group, and the C1 to C6 chain hydrocarbon group optionally having one or more atoms or groups selected from group W is selected in the range of each specified number of carbon atoms.

The notation of the "heterocyclic group" in the "5-membered heterocyclic group optionally having one or more atoms or groups selected from group Z" in the compound of the present invention represents a heterocyclic compound residue containing one or more atoms selected from the group consisting of a nitrogen atom, an oxygen atom and a sulfur atom, other than a carbon atom, in the cyclic structure, and at that time, when having two or more atoms or groups selected from group Z, the atoms or groups selected from group Z may be the same or different from each other.

In addition, a 5-membered heterocyclic group means a 5-membered aromatic heterocyclic group or a 5-membered nonaromatic heterocyclic group in the compound of the present invention.

Examples of the "5-membered heterocyclic group optionally having one or more atoms or groups selected from group Z" include 5-membered nonaromatic heterocyclic groups optionally having one or more atoms or groups selected from group Z such as a pyrrolidin-1-yl group, a 3,3,4,4-tetrafluoropyrrolidin-1-yl group and a tetrahydrofuran-2-yl group; and 5-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group and a 4-trifluoromethylpyrazol-1-yl group.

The notation of the "heterocyclic group" in the "6-membered aromatic heterocyclic group optionally having one or more atoms or groups selected from group Z" in the compound of the present invention represents a heterocyclic compound residue containing one or more atoms selected from the group consisting of a nitrogen atom, an oxygen atom and a sulfur atom, other than a carbon atom, in the cyclic structure, and at that time, when having two or more atoms or groups selected from group Z, the atoms or groups selected from group Z may be the same or different from each other.

Examples of the "6-membered aromatic heterocyclic group optionally having one or more atoms or groups selected from group Z" include a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "5- or 6-membered aromatic heterocyclic group (wherein the 5- or 6-membered aromatic heterocyclic group may have one or more atoms or groups selected from the group consisting of halogen atoms, C1 to C3 alkyl groups optionally having a halogen atom, and C1 to C3 alkoxy groups optionally having a halogen atom.)" in the compound of the present invention include a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 5-bromo-2-furyl group, a 5-methoxy-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidyl group, a 5-pyrimidyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidyl group, a 3-chloro-5-trifluoromethylpyridin-2-yl group and a 5-trifluoromethylpyridin-2-yl group.

Examples of the "C1 to C6 alkyl group optionally having one or more atoms or groups selected from the group consisting of halogen atoms and cyclopropyl groups (wherein the cyclopropyl group may have one or more halogen atoms or one or more C1 to C3 alkyl groups)" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2,-trifluoroethyl group, a pentafluoroethyl group, a heptafluoroisopropyl group, a cyclopropylmethyl group, a 2-cyclopropylethyl group, a 1-cyclopropylethyl group, and a 1-methylcyclopropylmethyl group.

Examples of the "C1 to C6 alkoxy groups optionally having one or more halogen atoms" in the compound of the present invention include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

Examples of the "C2 to C6 alkenyloxy groups optionally having one or more halogen atoms" in the compound of the present invention include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

Examples of the "C2 to C6 alkynyloxy groups optionally having one or more halogen atoms" in the compound of the present invention include a propargyloxy group, a 2-butynyloxy group, a 3-butynyloxy group, a 2-pentynyloxy group, a 2-hexynyloxy group, and a 4,4,4-trifluoro-2-butynyloxy group.

Examples of the "C1 to C6 alkylsulfanyl groups optionally having one or more halogen atoms" in the compound of the present invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

Examples of the "C1 to C6 alkylsulfinyl groups optionally having one or more halogen atoms" in the compound of the present invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the "C1 to C6 alkylsulfonyl groups optionally having one or more halogen atoms" in the compound of the present invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the "C2 to C6 alkylcarbonyl groups optionally having one or more halogen atoms" in the compound of the present invention include an acetyl group, a propionyl group, a butyryl group, a pentanoyl group, a hexanoyl group, and a trifluoroacetyl group.

Examples of the "C2 to C6 alkoxycarbonyl groups optionally having one or more halogen atoms" in the compound of the present invention include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethoxycarbonyl group.

Examples of the "C1 to C6 alkylamino groups optionally having one or more halogen atoms" in the compound of the present invention include a methylamino group, an ethylamino group, a 2,2,2-trifluoroethylamino group, a propylamino group, an isopropylamino group, and a butylamino group.

Examples of the "C2 to C8 dialkylamino groups optionally having one or more halogen atoms" in the compound of the present invention include a dimethylamino group, a diethylamino group, a bis(2,2,2-trifluoroethyl)amino group, and a dipropylamino group.

Examples of the "C3 to C6 cycloalkyl groups optionally having one or more halogen atoms" in the compound of the present invention include a cyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C3 to C6 cycloalkyl groups optionally having one or more halogen atoms or one or more C1 to C3 alkyl groups" in the compound of the present invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C4 to C9 cyclopropylalkyl groups (wherein the cyclopropyl group optionally has one or more halogen atoms or one or more C1 to C3 alkyl groups)" in the compound of the present invention include a cyclopropylmethyl group, a 2-cyclopropylethyl group, and a 1-cyclopropylethyl group.

Examples of the "C1 to C6 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C2 to C6 alkenyl group optionally having one or more halogen atoms" in the compound of the present invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C2 to C6 alkynyl group optionally having one or more halogen atoms" in the compound of the present invention include an ethynyl group, a propargyl group, a 2-butynyl group, a 3-butynyl group, a 1-pentynyl group, a 1-hexynyl group, and a 4,4,4-trifluoro-2-butynyl group.

Examples of the "C3 to C6 alkenyl group optionally having one or more halogen atoms" in the compound of the present invention include a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C3 to C6 alkynyl group optionally having one or more halogen atoms" in the compound of the present invention include a propargyl group, a 2-butynyl group, a 3-butynyl group, a 1-pentynyl group, a 1-hexynyl group, and a 4,4,4-trifluoro-2-butynyl group.

Examples of the "C1 to C3 alkyl group optionally having a C1 to C3 alkoxy group optionally having one or more halogen atoms" in the compound of the present invention include a methoxymethyl group, an ethoxymethyl group, a 1-(methoxy)ethyl group, a 2-(methoxy)ethyl group, a 1-(ethoxy)ethyl group, a 2-(ethoxy)ethyl group, and the like.

Examples of the "pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom.)" in the compound of the present invention include a 2-pyridyl group, a 3-pyridyl group, a 4-pyridyl group, a 5-trifluoromethyl-2-pyridyl group, and a 3-chloro-5-trifluoromethyl-2-pyridyl group.

Examples of the "pyrimidinyl group (wherein the pyrimidinyl group optionally has one or more atoms or substituents selected from the group consisting of halogen atoms, C1 to C3 alkyl groups optionally having a halogen atom, and C1 to C3 alkoxy groups optionally having a halogen atom.)" in the compound of the present invention include a 2-pyrimidinyl group, a 4-pyrimidinyl group, a 5-pyrimidinyl group, and a 2-chloro-4-pyrimidinyl group.

Examples of the compound of the present invention include the following compounds.

In the formula (1), compounds wherein J is J1;
In the formula (1), compounds wherein J is J2;
In the formula (1), compounds wherein J is J3;
In the formula (1), compounds wherein J is J4;
In the formula (1), compounds wherein J is J5;
In the formula (1), compounds wherein J is J6;
In the formula (1), compounds wherein $A^1$ is $CR^7$;
In the formula (1), compounds wherein $A^1$ is a nitrogen atom;
In the formula (1), compounds wherein $A^2$ is $CR^8$;
In the formula (1), compounds wherein $A^2$ is a nitrogen atom;
In the formula (1), compounds wherein $A^3$ is $CR^9$;
In the formula (1), compounds wherein $A^3$ is a nitrogen atom;
In the formula (1), compounds wherein $A^4$ is $CR^{10}$;
In the formula (1), compounds wherein $A^4$ is a nitrogen atom;
In the formula (1), compounds wherein $A^2$ is $CR^8$, $A^3$ is $CR^9$, and $A^4$ is $CR^{10}$;
In the formula (1), compounds wherein $A^2$ is $CR^8$, $A^3$ is $CR^9$, and $A^4$ is a nitrogen atom;
In the formula (1), compounds wherein $A^2$ is a nitrogen atom, $A^3$ is $CR^9$, and $A^4$ is $CR^{10}$;
In the formula (1), compounds wherein $A^2$ is a nitrogen atom, $A^3$ is $CR^9$, and $A^4$ is a nitrogen atom;
In the formula (1), compounds wherein $A^2$ is a nitrogen atom, $A^3$ is a nitrogen atom, and $A^4$ is $CR^{10}$;
In the formula (1), compounds wherein J is J1, $A^5$ is $CR^{11}$ (especially, CH), and $A^6$ is $CR^{12}$ (especially, CH);

In the formula (1), compounds wherein J is J1, $A^5$ is $CR^{11}$ (especially, CH), and $A^6$ is a nitrogen atom;

In the formula (1), compounds wherein J is J1, $A^5$ is a nitrogen atom, and $A^6$ is $CR^{12}$ (especially, CH);

In the formula (1), compounds wherein J is J2 or J3, and $B^2$ is CR14;

In the formula (1), compounds wherein J is J2 or J3, $B^1$ is a nitrogen atom, and $B^2$ is $CR^{14}$;

In the formula (1), compounds wherein J is J2 or J3, $B^1$ is a nitrogen atom, $B^2$ is $CR^{14}$, and $B^3$ is $NR^{15}$;

In the formula (1), compounds wherein J is J4, and $B^3$ is $NR^{15}$;

In the formula (1), compounds wherein J is J4, $B^1$ is $CR^{13}$, $B^2$ is a nitrogen atom, and $B^3$ is $NR^{15}$;

In the formula (1), compounds wherein J is J4, $B^1$ is a nitrogen atom, $B^2$ is $CR^{14}$, and $B^3$ is $NR^5$;

In the formula (1), compounds wherein J is J5 or J6, $B^4$ is $CR^{16}$ (especially, CH), $B^5$ is $CR^{17}$, and $B^6$ is a nitrogen atom;

The compounds wherein

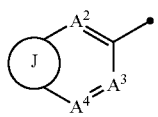

in the formula (1) is any of the following J1-1 to J1-5:

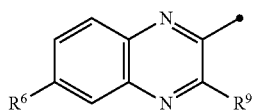
J1-1

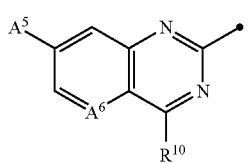
J1-2

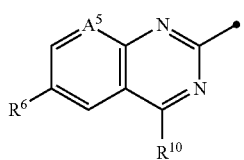
J1-3

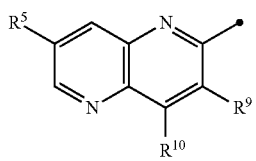
J1-4

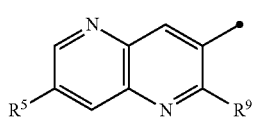
J1-5 wherein symbols represent the same meaning as in the formula (1).

The compounds wherein

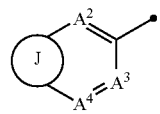

in the formula (1) is any of the following J2-1 to J3-1:

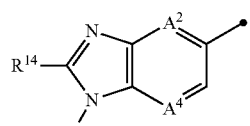
J2-1

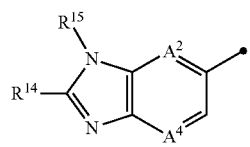
J3-1 wherein symbols represent the same meaning as in the formula (1).

The compounds wherein

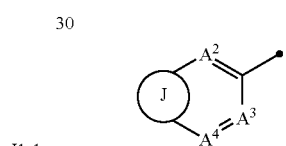

in the formula (1) is any of the following J5-1 to J6-1:

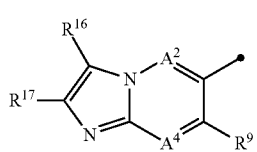
J5-1

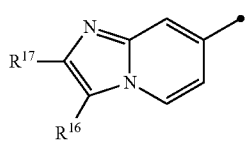
J6-1 wherein symbols represent the same meaning as in the formula (1).

In the formula (1), compounds wherein $R^1$ is a C1 to C6 chain hydrocarbon group optionally having one or more atoms or groups selected from group X;

In the formula (1), compounds wherein $R^1$ is a C1 to C6 alkyl group optionally having one or more atoms or groups selected from halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms;

In the formula (1), compounds wherein $R^1$ is a C1 to C6 alkyl group optionally having one or more atoms or groups selected from halogen atoms and cyclopropyl groups (wherein the cyclopropyl group optionally has one or more halogen atoms or one or more C1 to C3 alkyl groups);

In the formula (1), compounds wherein $R^1$ is a C1 to C6 alkyl group, a C1 to C6 haloalkyl group, or a C4 to C9 cyclopropylalkyl group (wherein the cyclopropyl group optionally has one or more halogen atoms or one or more C1 to C3 alkyl groups);

In the formula (1), compounds wherein $R^1$ is a C2 to C6 alkyl group, a C1 to C6 haloalkyl group, or a C4 to C9 cyclopropylalkyl group (wherein the cyclopropyl group optionally has one or more halogen atoms or one or more C1 to C3 alkyl groups);

In the formula (1), compounds wherein $R^1$ is a C3 to C6 alicyclic hydrocarbon group optionally having one or more atoms or groups selected from group Y;

In the formula (1), a C3 to C6 cycloalkyl group optionally having one or more halogen atoms or one or more C1 to C3 alkyl groups;

In the formula (1), compounds wherein $R^1$ is a methyl group, an ethyl group, a propyl group, an isopropyl group, a trifluoromethyl group, a 2,2,2-trifluoroethyl group, a cyclopropylmethyl group, a cyclopropyl group, a 2-methylcyclopropyl group, or a 2,2-difluorocyclopropyl group.

In the formula (1), compounds wherein $R^1$ is an ethyl group, a cyclopropylmethyl group, or a cyclopropyl group;

In the formula (1), compounds wherein $R^1$ is an ethyl group;

In the formula (1), compounds wherein $A^1$ is $CR^7$, $R^2$ and $R^7$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{19}$, $-S(O)_mR^{19}$, $-SF_5$, a cyano group, a nitro group, a halogen atom or a hydrogen atom, and $R^4$ is a C1 to C6 chain hydrocarbon group optionally having one or more atoms or groups selected from group W, a phenyl group optionally having one or more atoms or groups selected from group Z, a 5- or 6-membered heterocyclic group optionally having one or more atoms or groups selected from group Z, $-OR^{19}$, $-S(O)_mR^{19}$, $-SF_5$, a cyano group, a nitro group, a halogen atom or a hydrogen atom;

In the formula (1), compounds wherein $A^1$ is $CR^7$, and $R^2$, $R^4$ and $R^7$ are the same or different and are a C1 to C6 alkyl group optionally having one or more halogen atoms, $-OR^{19}$ (wherein $R^{19}$ is a C1 to C6 alkyl group optionally having one or more halogen atoms), $-S(O)_mR^{19}$ (wherein $R^{19}$ is a C1 to C6 alkyl group optionally having one or more halogen atoms), a halogen atom, or a hydrogen atom;

In the formula (1), compounds wherein $A^1$ is $CR^7$, and $R^2$, $R^4$ and $R^7$ are the same or different and are a halogen atom or a hydrogen atom;

In the formula (1), compounds wherein $A^1$ is $CR^7$, and $R^2$, $R^4$ and $R^7$ are all a hydrogen atom;

In the formula (1), compounds wherein $A^1$ is a nitrogen atom, $R^2$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{19}$, $-S(O)_mR^{19}$, $-SF_5$, a cyano group, a nitro group, a halogen atom or a hydrogen atom, and $R^4$ is a C1 to C6 chain hydrocarbon group optionally having one or more atoms or groups selected from group W, a phenyl group optionally having one or more atoms or groups selected from group Z, a 5- or 6-membered heterocyclic group optionally having one or more atoms or groups selected from group Z, $-OR^{19}$, $-S(O)_mR^{19}$, $-SF_5$, a cyano group, a nitro group, a halogen atom or a hydrogen atom;

In the formula (1), compounds wherein $A^1$ is a nitrogen atom, and $R^2$ and $R^4$ are the same or different and are a C1 to C6 alkyl group optionally having one or more halogen atoms, $-OR^{19}$ (wherein $R^{19}$ is a C1 to C6 alkyl group optionally having one or more halogen atoms), $-S(O)_mR^{19}$ (wherein $R^{19}$ is a C1 to C6 alkyl group optionally having one or more halogen atoms), a halogen atom, or a hydrogen atom;

In the formula (1), compounds wherein $A^1$ is a nitrogen atom, and $R^2$ and $R^4$ are the same or different and are a halogen atom or a hydrogen atom;

In the formula (1), compounds wherein $A^1$ is a nitrogen atom, and $R^2$ and $R^4$ are both a hydrogen atom;

In the formula (1), compounds wherein $R^3$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{19}$, $-S(O)_mR^{19}$, $-SF_5$, a cyano group, a nitro group, a halogen atom, or a hydrogen atom;

In the formula (1), compounds wherein $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered aromatic heterocyclic group (wherein the 5- or 6-membered aromatic heterocyclic group optionally has one or more atoms or substituents selected from the group consisting of halogen atoms, C1 to C3 alkyl groups optionally having a halogen atom and C1 to C3 alkoxy groups optionally having a halogen atom), $-OR^{19}$ (wherein $R^{19}$ is a C1 to C6 alkyl group optionally having one or more halogen atoms), $-S(O)_mR^{19}$ (wherein $R^{19}$ is a C1 to C6 alkyl group optionally having one or more halogen atoms), a cyano group, a nitro group, a halogen atom, or a hydrogen atom;

In the formula (1), compounds wherein $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom), a pyrimidyl group (wherein the pyrimidyl group optionally has one or more atoms or substituents selected from the group consisting of halogen atoms, C1 to C3 alkyl groups optionally having a halogen atom, and C1 to C3 alkoxy groups optionally having a halogen atom), $-OR^{19}$ (wherein $R^{19}$ is a C1 to C6 alkyl group optionally having one or more halogen atoms), $-S(O)_mR^{19}$ (wherein $R^{19}$ is a C1 to C6 alkyl group optionally having one or more halogen atoms), a halogen atom, or a hydrogen atom;

In the formula (1), compounds wherein $R^3$ is a C1 to C6 alkyl group optionally having one or more halogen atoms, $-OR^{19}$ (wherein $R^{19}$ is a C1 to C6 alkyl group optionally having one or more halogen atoms), $-S(O)_mR^{19}$ (wherein $R^{19}$ is a C1 to C6 alkyl group optionally having one or more halogen atoms), a halogen atom, or a hydrogen atom;

In the formula (1), compounds wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)$ $CF_2CF_3$, —$S(O)_2CF_2CF_3$, a 2-pyridyl group, a 5-trifluoromethyl-2-pyridyl group, a 2-pyrimidyl group, a fluorine atom, a chlorine atom, a bromine atom, an iodine atom, or a hydrogen atom;

In the formula (1), compounds wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)$ $CF_2CF_3$, —$S(O)_2CF_2CF_3$, a fluorine atom, a chlorine atom, a bromine atom, an iodine atom, or a hydrogen atom;

In the formula (1), compounds wherein $R^3$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —$CF_2CF_3$, —$CF_2CF_2CF_3$, —$CF(CF_3)_2$, —$CF_2CF_2CF_2CF_3$, —$OCF_3$, —$OCF_2CF_3$, —$SCF_3$, —$S(O)CF_3$, —$S(O)_2CF_3$, —$SCF_2CF_3$, —$S(O)$ $CF_2CF_3$, —$S(O)_2CF_2CF_3$, a fluorine atom, a chlorine atom, a bromine atom, or an iodine atom;

In the formula (1), compounds wherein J is J1, and $R^5$ and $R^6$ are the same or different and are a C1 to C6 chain hydrocarbon group optionally having one or more atoms or groups selected from group X, —$OR^{21}$, —$S(O)_mR^{21}$, —$SF_5$, a halogen atom, or a hydrogen atom;

In the formula (1), compounds wherein J is J1, and $R^5$ and $R^6$ are the same or different and are a C1 to C6 alkyl group optionally having one or more halogen atoms, —$OR^{21}$ (wherein $R^{21}$ is a C1 to C6 alkyl group optionally having one or more halogen atoms), —$S(O)_mR^{21}$ (wherein $R^{21}$ is a C1 to C6 alkyl group optionally having one or more halogen atoms), —$SF_5$, a halogen atom, or a hydrogen atom;

In the formula (1), compounds wherein J is J1, one of $R^5$ and $R^6$ is a C1 to C6 chain hydrocarbon group optionally having one or more atoms or groups selected from group X, —$OR^{21}$, —$S(O)_mR^{21}$, —$SF_5$ or a halogen atom, and the other is a halogen atom or a hydrogen atom;

In the formula (1), compounds wherein J is J1, one of $R^5$ and $R^6$ is a C1 to C6 alkyl group optionally having one or more halogen atoms, —$OR^{21}$ (wherein $R^{21}$ is a C1 to C6 alkyl group optionally having one or more halogen atoms), —$S(O)_mR^{21}$ (wherein $R^{21}$ is a C1 to C6 alkyl group optionally having one or more halogen atoms), —$SF_5$ or a halogen atom, and the other is a halogen atom or a hydrogen atom;

In the formula (1), compounds wherein J is J1, one of $R^5$ and $R^6$ is a C1 to C6 haloalkyl group, —$OR^{21}$ (wherein $R^{21}$ is a C1 to C6 haloalkyl group), —$S(O)_mR^{21}$ (wherein $R^{21}$ is a C1 to C6 haloalkyl group), —$SF_5$ or a halogen atom, and the other is a halogen atom or a hydrogen atom;

In the formula (1), compounds wherein J is J1, one of $R^5$ and $R^6$ is a C1 to C6 haloalkyl group, —$OR^{21}$ (wherein $R^{21}$ is a C1 to C6 haloalkyl group), —$S(O)_mR^{21}$ (wherein $R^{21}$ is a C1 to C6 haloalkyl group) or —$SF_5$, and the other is a halogen atom or a hydrogen atom;

In the formula (1), compounds wherein J is J1, one of $R^5$ and $R^6$ is a C1 to C6 haloalkyl group, —$OR^{21}$ (wherein $R^{21}$ is a C1 to C6 haloalkyl group), —$S(O)_mR^{21}$ (wherein $R^{21}$ is a C1 to C6 haloalkyl group) or a halogen atom, and the other is a halogen atom or a hydrogen atom;

In the formula (1), compounds wherein J is J1, one of $R^5$ and $R^6$ is a C1 to C6 haloalkyl group, —$OR^{21}$ (wherein $R^{21}$ is a C1 to C6 haloalkyl group) or —$S(O)_mR^{21}$ (wherein $R^{21}$ is a C1 to C6 haloalkyl group), and the other is a halogen atom or a hydrogen atom;

In the formula (1), compounds wherein J is J1, one of $R^5$ and $R^6$ is a C1 to C6 perfluoroalkyl group, —$OR^{21}$ (wherein $R^{21}$ is a C1 to C6 perfluoroalkyl group) or —$S(O)_mR^{21}$ (wherein $R^{21}$ is a C1 to C6 perfluoroalkyl group), and the other is a halogen atom or a hydrogen atom;

In the formula (1), compounds wherein J is J1, one of $R^5$ and $R^6$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)$ $CF_3$, —$S(O)_2CF_3$, —$SCF_2CF_3$, —$S(O)$ $CF_2CF_3$, —$S(O)_2CF_2CF_3$, —$SF_5$, a fluorine atom, a chlorine atom, a bromine atom or an iodine atom, and the other is a halogen atom or a hydrogen atom;

In the formula (1), compounds wherein J is J1, one of $R^5$ and $R^6$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, —$SF_5$, a fluorine atom, a chlorine atom, a bromine atom or an iodine atom, and the other is a hydrogen atom;

In the formula (1), compounds wherein $A^2$ is a nitrogen atom or $CR^8$, and $R^8$ is a C1 to C6 chain hydrocarbon group optionally having one or more atoms or groups selected from group X, —$OR^{23}$, —$S(O)_mR^{24}$, —$NR^{24}R^{25}$, a halogen atom or a hydrogen atom;

In the formula (1), compounds wherein $A^2$ is a nitrogen atom or $CR^8$, and $R^8$ is a C1 to C6 alkyl group optionally having one or more halogen atoms, —$OR^{23}$ (wherein $R^{23}$ is a C1 to C6 alkyl group optionally having one or more halogen atoms), —$S(O)_mR^{24}$ (wherein $R^{24}$ is a C1 to C6 alkyl group optionally having one or more halogen atoms), —$NR^{24}R^{25}$ (wherein $R^{24}$ and $R^{25}$ are the same or different and are a C1 to C6 alkyl group optionally having one or more halogen atoms or a hydrogen atom), a halogen atom or a hydrogen atom;

In the formula (1), compounds wherein $A^2$ is a nitrogen atom or $CR^8$, and $R^8$ is a C1 to C3 alkyl group or a hydrogen atom;

In the formula (1), compounds wherein $A^3$ is a nitrogen atom or $CR^9$, and $R^9$ is a C1 to C6 chain hydrocarbon group optionally having one or more atoms or groups selected from group X, —$OR^{23}$, —$S(O)_mR^{24}$, —$NR^{24}R^{25}$, a halogen atom or a hydrogen atom;

In the formula (1), compounds wherein $A^3$ is a nitrogen atom or $CR^9$, and $R^9$ is a C1 to C6 alkyl group optionally having one or more halogen atoms, —$OR^{23}$ (wherein $R^{23}$ is a C1 to C6 alkyl group optionally having one or more halogen atoms), —$S(O)_mR^{24}$ (wherein $R^{24}$ is a C1 to C6 alkyl group optionally having one or more halogen atoms), —$NR^{24}R^{25}$ (wherein $R^{24}$ and R are the same or different and are a C1 to C6 alkyl group optionally having one or more halogen atoms or a hydrogen atom), a halogen atom or a hydrogen atom;

In the formula (1), compounds wherein $A^3$ is a nitrogen atom or $CR^9$, and $R^9$ is a C1 to C3 alkyl group, a halogen atom or a hydrogen atom;

In the formula (1), compounds wherein $A^3$ is a nitrogen atom or $CR^9$, and $R^9$ is a hydrogen atom;

In the formula (1), compounds wherein $A^4$ is a nitrogen atom or $CR^{10}$, and $R^{10}$ is a C1 to C6 chain hydrocarbon group optionally having one or more atoms or groups selected from group X, —$OR^{23}$, —$S(O)_mR^{24}$, —$NR^{24}R^{25}$, a halogen atom or a hydrogen atom;

In the formula (1), compounds wherein $A^4$ is a nitrogen atom or $CR^{10}$, and $R^{10}$ is a C1 to C6 alkyl group optionally having one or more halogen atoms, —$OR^{23}$ (wherein $R^{23}$ is a C1 to C6 alkyl group optionally having one or more halogen atoms), —$S(O)_mR^{24}$ (wherein $R^{24}$ is a C1 to C6 alkyl group optionally having one or more halogen atoms), $-NR^{24}R^{25}$ (wherein $R^{24}$ and R are the same or different and are a C1 to C6 alkyl group optionally having one or more halogen atoms or a hydrogen atom), a halogen atom or a hydrogen atom;

In the formula (1), compounds wherein $A^4$ is a nitrogen atom or $CR^{10}$, and $R^{10}$ is a C1 to C3 alkyl group, $-NR^{24}R^{25}$ (wherein $R^{24}$ and $R^{25}$ are the same or different and are a C1 to C6 alkyl group or a hydrogen atom), a halogen atom or a hydrogen atom;

In the formula (1), compounds wherein $A^4$ is $CR^{10}$, and $R^{10}$ is a hydrogen atom;

In the formula (1), compounds wherein J is J1, $A^5$ is a nitrogen atom or $CR^{11}$, and $R^{11}$ is a C1 to C6 chain hydrocarbon group optionally having one or more halogen atoms, $-OR^{21}$, $-S(O)_mR^{21}$, a halogen atom or a hydrogen atom;

In the formula (1), compounds wherein J is J1, $A^5$ is a nitrogen atom or $CR^{11}$, and $R^{11}$ is a C1 to C6 alkyl group optionally having one or more halogen atoms, $-OR^{21}$ (wherein $R^{21}$ is a C1 to C6 alkyl group optionally having one or more halogen atoms), $-S(O)_mR^{21}$ (wherein $R^{21}$ is a C1 to C6 alkyl group optionally having one or more halogen atoms), a halogen atom or a hydrogen atom;

In the formula (1), compounds wherein J is J1, $A^5$ is a nitrogen atom or $CR^{11}$, and $R^{11}$ is a halogen atom or a hydrogen atom;

In the formula (1), compounds wherein J is J1, $A^5$ is a nitrogen atom or $CR^{11}$, and $R^{11}$ is a hydrogen atom;

In the formula (1), compounds wherein J is J1, $A^6$ is a nitrogen atom or $CR^{12}$, and $R^{12}$ is a C1 to C6 chain hydrocarbon group optionally having one or more halogen atoms, $-OR^{21}$, $-S(O)_mR^{21}$, a halogen atom or a hydrogen atom;

In the formula (1), compounds wherein J is J1, $A^6$ is a nitrogen atom or $CR^{12}$, and $R^{12}$ is a C1 to C6 alkyl group optionally having one or more halogen atoms, $-OR^{21}$ (wherein $R^{21}$ is a C1 to C6 alkyl group optionally having one or more halogen atoms), $-S(O)_mR^{21}$ (wherein $R^{21}$ is a C1 to C6 alkyl group optionally having one or more halogen atoms), a halogen atom or a hydrogen atom;

In the formula (1), compounds wherein J is J1, $A^6$ is a nitrogen atom or $CR^{12}$, and $R^{12}$ is a halogen atom or a hydrogen atom;

In the formula (1), compounds wherein J is J1, $A^6$ is a nitrogen atom or $CR^{12}$, and $R^{12}$ is a hydrogen atom;

In the formula (1), compounds wherein J is J2 or J3, $B^1$ is a nitrogen atom or $CR^{13}$, $B^2$ is $CR^{14}$, $R^{13}$ is a C1 to C6 chain hydrocarbon group optionally having one or more atoms or groups selected from group X, $-OR^{26}$, $-S(O)_mR^6$, a halogen atom or a hydrogen atom, and $R^{14}$ is a C1 to C6 chain hydrocarbon group optionally having one or more atoms or groups selected from group X, $-OR^{21}$, $-S(O)_mR$, $-SF_5$ or a halogen atom;

In the formula (1), compounds wherein J is J2 or J3, $B^1$ is a nitrogen atom or $CR^{13}$, $B^2$ is $CR^{14}$, $R^{13}$ is a C1 to C6 alkyl group optionally having one or more halogen atoms, $-OR^{26}$ (wherein $R^{26}$ is a C1 to C6 alkyl group optionally having one or more halogen atoms), $-S(O)_mR^{26}$ (wherein $R^{26}$ is a C1 to C6 alkyl group optionally having one or more halogen atoms), a halogen atom or a hydrogen atom, and $R^{14}$ is a C1 to C6 alkyl group optionally having one or more halogen atoms, $-OR^{26}$ (wherein $R^{26}$ is a C1 to C6 alkyl group optionally having one or more halogen atoms), $-S(O)_mR^{26}$ (wherein $R^{26}$ is a C1 to C6 alkyl group optionally having one or more halogen atoms), $-SF_5$ or a halogen atom;

In the formula (1), compounds wherein J is J2 or J3, $B^1$ is a nitrogen atom or $CR^{13}$, $B^2$ is $CR^{14}$, $R^{13}$ is a halogen atom or a hydrogen atom, and $R^{14}$ is a C1 to C6 alkyl group optionally having one or more halogen atoms, $-OR^{26}$ (wherein $R^{26}$ is a C1 to C6 alkyl group optionally having one or more halogen atoms), $-S(O)_mR^{26}$ (wherein $R^{26}$ is a C1 to C6 alkyl group optionally having one or more halogen atoms), $-SF_5$ or a halogen atom; In the formula (1), compounds wherein J is J2 or J3, $B^1$ is a nitrogen atom or $CR^{13}$, $B^2$ is $CR^{14}$, $R^{13}$ is a halogen atom or a hydrogen atom, and $R^{14}$ is a C1 to C6 haloalkyl group, $-OR^{26}$ (wherein $R^{26}$ is a C1 to C6 haloalkyl group) or $-S(O)_mR^{26}$ (wherein $R^{26}$ is a C1 to C6 haloalkyl group);

In the formula (1), compounds wherein J is J2 or J3, $B^1$ is a nitrogen atom or $CR^{13}$, $B^2$ is $CR^{14}$, $R^{13}$ is a halogen atom or a hydrogen atom, and $R^{14}$ is a trifluoromethyl group, $-CF_2CF_3$, $-CF_2CF_2CF_3$, $-CF(CF_3)_2$, $-OCF_3$, $-OCF_2CF_3$, $-SCF_3$, $-S(O)CF_3$, $-S(O)_2CF_3$, $-SCF_2CF_3$, $-S(O)CF_2CF_3$, $-S(O)_2CF_2CF_3$, $-SF_5$, a fluorine atom, a chlorine atom, a bromine atom or an iodine atom;

In the formula (1), compounds wherein J is J2 or J3, $B^1$ is a nitrogen atom or $CR^{13}$, $B^2$ is $CR^{14}$, $R^{13}$ is a hydrogen atom, and $R^{14}$ is a trifluoromethyl group, $-CF_2CF_3$, $-CF_2CF_2CF_3$, $-CF(CF_3)_2$, $-OCF_3$, $-OCF_2CF_3$, $-SCF_3$, $-S(O)CF_3$, $-S(O)_2CF_3$, $-SCF_2CF_3$, $-S(O)CF_2CF_3$, $-S(O)_2CF_2CF_3$, $-SF_5$, a fluorine atom, a chlorine atom, a bromine atom or an iodine atom;

In the formula (1), compounds wherein J is J2 or J3, $B^2$ is $CR^{14}$, $B^3$ is $NR^{15}$, and $R^5$ is a C1 to C6 chain hydrocarbon group optionally having one or more atoms or groups selected from group X or a C3 to C6 alicyclic hydrocarbon group optionally having one or more atoms or groups selected from group Y;

In the formula (1), compounds wherein J is J2 or J3, $B^2$ is $CR^{14}$, $B^3$ is $NR^{15}$, and $R^{15}$ is a C1 to C6 alkyl group optionally having one or more halogen atoms, a C3 to C6 alkenyl group optionally having one or more halogen atoms, a C3 to C6 alkynyl group optionally having one or more halogen atoms, a C1 to C6 alkyl group having a C1 to C3 alkoxy optionally having one or more halogen atoms or a C3 to C6 cycloalkyl group optionally having one or more halogen atoms or one or more C1 to C3 alkyl groups;

In the formula (1), compounds wherein J is J2 or J3, $B^2$ is $CR^{14}$, $B^3$ is $NR^{15}$, and $R^{15}$ is a methyl group, an ethyl group, a propyl group, an allyl group, a propargyl group, a hydrogen atom, a methoxymethyl group, an ethoxymethyl group, a 1-(methoxy)ethyl group or a 1-(ethoxy)ethyl group;

In the formula (1), compounds wherein J is J2 or J3, $B^2$ is $CR^{14}$, $B^3$ is $NR^{15}$, and $R^{15}$ is a methyl group, a propargyl group, a hydrogen atom, a methoxymethyl group or an ethoxymethyl group;

In the formula (1), compounds wherein J is J2 or J3, $B^2$ is $CR^{14}$, $B^3$ is $NR^{15}$, and $R^{15}$ is a methyl group;

In the formula (1), compounds wherein J is J5 or J6, $B^4$ is $CR^{16}$, $B^5$ is $CR^{17}$, $B^6$ is a nitrogen atom, $R^{16}$ is a C1 to C6 alkyl group optionally having one or more halogen atoms, $-OR^{26}$ (wherein $R^{26}$ is a C1 to C6 alkyl group optionally having one or more halogen atoms), $-S(O)_mR^{26}$ (wherein $R^{21}$ is a C1 to C6 alkyl group optionally having one or more halogen atoms), a halogen atom or a hydrogen atom, and $R^{17}$ is a C1 to C6 chain hydrocarbon group optionally having one or more atoms or groups selected from group X, $-OR^{26}$, $-S(O)_mR^{26}$, $-SF_5$ or a halogen atom;

In the formula (1), compounds wherein J is J5 or J6, $B^4$ is $CR^{16}$, $B^5$ is $CR^{17}$, $B^6$ is a nitrogen atom, $R^{16}$ is a C1 to C6 alkyl group optionally having one or more halogen atoms, a halogen atom or a hydrogen atom, and $R^{17}$ is a C1 to C6 alkyl group optionally having one or more halogen atoms, $-OR^{26}$ (wherein $R^{26}$ is a C1 to C6 alkyl group optionally having one or more halogen atoms), $-S(O)_mR^{26}$ (wherein $R^{26}$ is a C1 to C6 alkyl group optionally having one or more halogen atoms), $-SF_5$ or a halogen atom;

In the formula (1), compounds wherein J is J5 or J6, $B^4$ is $CR^{16}$, $B^5$ is $CR^{17}$, $B^6$ is a nitrogen atom, $R^{16}$ is a halogen atom or a hydrogen atom, and $R^{17}$ is a C1 to C6 haloalkyl group, $-OR^{26}$ (wherein $R^{26}$ is a C1 to C6 haloalkyl group), $-S(O)_mR^{26}$ (wherein $R^{26}$ is a C1 to C6 haloalkyl group), $-SF_5$ or a halogen atom;

In the formula (1), compounds wherein J is J5 or J6, $B^4$ is $CR^{16}$, $B^5$ is $CR^{17}$, $B^6$ is a nitrogen atom, $R^{16}$ is a halogen atom or a hydrogen atom, and $R^{17}$ is a C1 to C6 perfluoroalkyl group, $-OR^{26}$ (wherein $R^{26}$ is a C1 to C6 perfluoroalkyl group) or $-S(O)_mR^{26}$ (wherein $R^{26}$ is a C1 to C6 perfluoroalkyl group);

In the formula (1), compounds wherein J is J5 or J6, $B^4$ is $CR^{16}$, $B^5$ is $CR^{17}$, $B^6$ is a nitrogen atom, $R^{16}$ is a halogen atom or a hydrogen atom, and $R^{17}$ is a trifluoromethyl group, $-CF_2CF_3$, $-CF_2CF_2CF_3$, $-CF(CF_3)_2$, $-OCF_3$, $-OCF_2CF_3$, $-SCF_3$, $-S(O)CF_3$, $-S(O)_2CF_3$, $-SCF_2CF_3$, $-S(O)CF_2CF_3$, $-S(O)_2CF_2CF_3$, $SF_5$, a fluorine atom, a chlorine atom, a bromine atom or an iodine atom;

In the formula (1), compounds wherein J is J5 or J6, $B^4$ is $CR^{16}$, $B^5$ is $CR^{17}$, $B^6$ is a nitrogen atom, $R^{16}$ is a hydrogen atom, and $R^{17}$ is a trifluoromethyl group, $CF_2CF_3$, $-CF_2CF_2CF_3$, $-CF(CF_3)_2$, $-OCF_3$, $-OCF_2CF_3$, $-SCF_3$, $-S(O)CF_3$, $-S(O)_2CF_3$, $-SCF_2CF_3$, $-S(O)CF_2CF_3$, $-S(O)_2CF_2CF_3$, $SF_5$, a fluorine atom or an iodine atom;

In the formula (1), compounds wherein n is 0;
In the formula (1), compounds wherein n is 1; and
In the formula (1), compounds wherein n is 2.

Examples of the compound of the present invention include the following compounds.

Embodiment 1

In the formula (1), compounds wherein

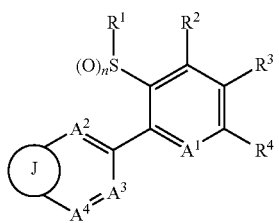

$A^1$ is a nitrogen atom or CH,
$R^2$ and $R^4$ are a hydrogen atom, and
partial structure:

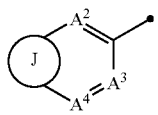

is the following J1-1 to J1-5, J2-1, J3-1, J5-1 or J6-1;

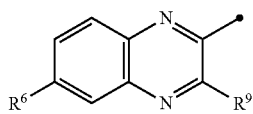
J1-1

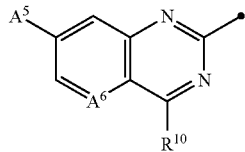
J1-2

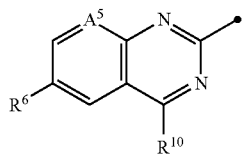
J1-3

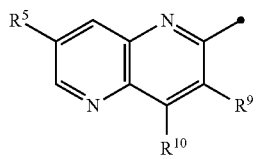
J1-4

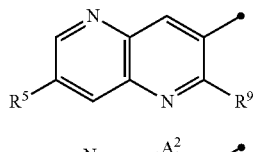
J1-5

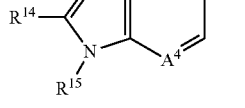
J2-1

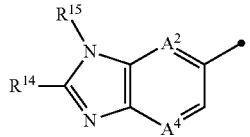
J3-1

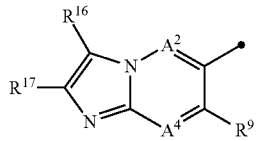
J5-1

J6-1 wherein symbols represent the same meaning as in the formula (1).

Embodiment 2

In the formula (1), compounds wherein
$A^1$ is a nitrogen atom or CH,
$R^1$ is a C1 to C3 alkyl group, a C1 to C3 haloalkyl group, a C4 to C6 cyclopropylalkyl group or a C3 to C6 cycloalkyl group,
$R^2$ and $R^4$ are a hydrogen atom,
$R^3$ is a C1 to C3 alkyl group, a C1 to C3 haloalkyl group (especially, a C1 to C3 perfluoroalkyl group), $-OR^{19}$ (wherein $R^{19}$ is a C1 to C3 haloalkyl group, especially a C1 to C3 perfluoroalkyl group such as $-CF_3$ or $-CF_2CF_3$), $-S(O)_mR^{19}$ (wherein $R^{19}$ is a C1 to C3 haloalkyl group, especially a C1 to C3 perfluoroalkyl group such as —CF₃ or —CF₂CF₃, and m is 0, 1 or 2), a halogen atom or a hydrogen atom, and partial structure:

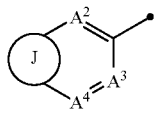

is the following J1-1 to J1-5, J2-1, J3-1, J5-1 or J6-1;

J1-1
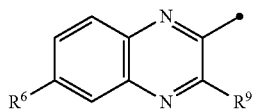

J1-2
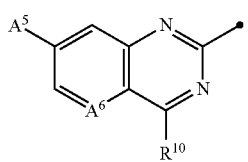

J1-3
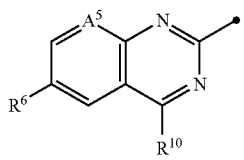

J1-4
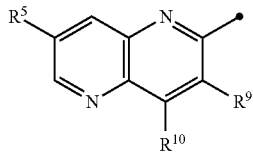

J1-5
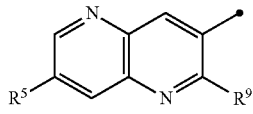

J2-1
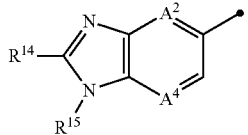

J3-1
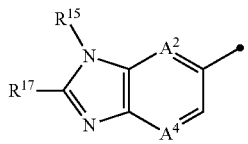

J5-1
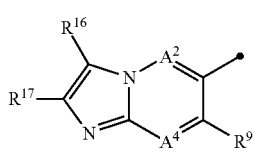

J6-1
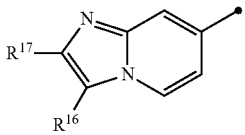

wherein
$A^2$ is a nitrogen atom, CH or CCH₃,
$A^4$ is a nitrogen atom or CH,
$A^5$ is a nitrogen atom or CH,
$A^6$ is a nitrogen atom or CH,
$R^5$ is a C1 to C3 haloalkyl group (especially, a C1 to C3 perfluoroalkyl group), —OR²¹ (wherein $R^{21}$ is a C1 to C3 haloalkyl group, especially a C1 to C3 perfluoroalkyl group such as —CF₃ or —CF₂CF₃), —S(O)ₘR²¹ (wherein $R^{21}$ is a C1 to C3 haloalkyl group, especially a C1 to C3 perfluoroalkyl group such as —CF₃ or —CF₂CF₃, and m is 0, 1 or 2) or a halogen atom,
$R^6$ is a C1 to C3 haloalkyl group (especially, a C1 to C3 perfluoroalkyl group), —OR²¹ (wherein $R^{21}$ is a C1 to C3 haloalkyl group, especially a C1 to C3 perfluoroalkyl group such as —CF₃ or —CF₂CF₃), —S(O)ₘR²¹ (wherein $R^{21}$ is a C1 to C3 haloalkyl group, especially a C1 to C3 perfluoroalkyl group such as —CF₃ or —CF₂CF₃, and m is 0, 1 or 2) or a halogen atom,
$R^9$ is a C1 to C3 alkyl group, a halogen atom or a hydrogen atom,
$R^{10}$ is a C1 to C3 alkyl group, NR²⁴R²⁵ (wherein $R^{24}$ and $R^{25}$ are the same or different, and are a C1 to C3 alkyl group or a hydrogen atom), a halogen atom or a hydrogen atom,
$R^{14}$ is a C1 to C3 haloalkyl group (especially, a C1 to C3 perfluoroalkyl group), —OR²⁶ (wherein $R^{26}$ is a C1 to C3 haloalkyl group, especially a C1 to C3 perfluoroalkyl group such as —CF₃ or —CF₂CF₃), —S(O)R²⁶ (wherein $R^{26}$ is a C1 to C3 haloalkyl group, especially a C1 to C3 perfluoroalkyl group such as —CF₃ or —CF₂CF₃, and m is 0, 1 or 2) or a halogen atom,
$R^{15}$ is a C1 to C3 alkyl group or a hydrogen atom,
$R^{16}$ is a halogen atom or a hydrogen atom,
$R^{17}$ is a C1 to C3 haloalkyl group (especially, a C1 to C3 perfluoroalkyl group), —OR²⁶ (wherein $R^{26}$ is a C1 to C3 haloalkyl group, especially a C1 to C3 perfluoroalkyl group such as —CF₃ or —CF₂CF₃), —S(O)ₘR²⁶ (wherein $R^{26}$ is a C1 to C3 haloalkyl group, especially a C1 to C3 perfluoroalkyl group such as —CF₃ or —CF₂CF₃, and m is 0, 1 or 2) or a hydrogen atom, Embodiment 3

Examples of the compound of the present invention include the following compounds.
In the formula (1), compounds wherein
$A^1$ is CH,
$R^1$ is a C1 to C3 alkyl group (especially, an ethyl group),
$R^2$ and $R^4$ are a hydrogen atom,
$R^3$ is a halogen atom or a hydrogen atom, and
partial structure:

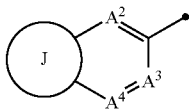

is the following J1-1 to J1-3, J2-1, J3-1, J5-1 or J6-1:

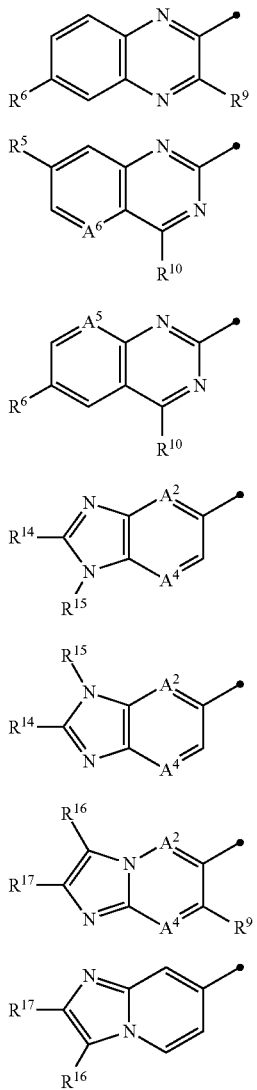

wherein $A^2$ is a nitrogen atom, CH or CCH$_3$, $A^4$ is a nitrogen atom or CH (wherein $A^2$ and $A^4$ are not a nitrogen atom at the same time), $A^5$ is a nitrogen atom, $A^6$ is a nitrogen atom or CH, $R^5$ is a C1 to C3 haloalkyl group (especially, a C1 to C3 perfluoroalkyl group), $R^6$ is a C1 to C3 haloalkyl group (especially, a C1 to C3 perfluoroalkyl group), $R^9$ is a C1 to C3 alkyl group (especially, a methyl group) or a hydrogen atom, $R^{10}$ is a C1 to C3 alkyl group (especially, a methyl group), an amino group optionally having one C1 to C3 alkyl group, a halogen atom or a hydrogen atom, $R^{14}$ is a C1 to C3 haloalkyl group (especially, a C1 to C3 perfluoroalkyl group), $R^{15}$ is a C1 to C3 alkyl group (especially, a methyl group), $R^{16}$ is a hydrogen atom, and $R^{17}$ is a C1 to C3 haloalkyl group (especially, a C1 to C3 perfluoroalkyl group).

Embodiment 3-1

In Embodiment 3, compounds wherein the partial structure is J1-1.

Embodiment 3-2

In Embodiment 3, compounds wherein the partial structure is J1-2.

Embodiment 3-3

In Embodiment 3, compounds wherein the partial structure is J1-3.

Embodiment 3-3-1

In Embodiment 3-3, compounds wherein $R^{10}$ is a C1 to C3 alkyl group (especially, a methyl group), an amino group, or a halogen atom (especially, a chlorine atom).

Embodiment 3-5

In Embodiment 3, compounds wherein the partial structure is J3-1.

Embodiment 3-6

In Embodiment 3, compounds wherein the partial structure is J5-1.

Embodiment 3-7

In Embodiment 3, compounds wherein the partial structure is J6-1.

Embodiment 4

In the formula (1), compounds wherein
$A^1$ is CH,
$R^1$ is an ethyl group,
$R^2$ and $R^4$ are a hydrogen atom,
$R^3$ is a chlorine atom or a hydrogen atom, and partial structure:

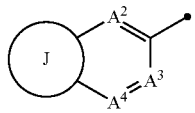

is the following J1-1 to J1-3, J2-1, J3-1, J5-1 or J6-1:

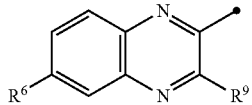

-continued

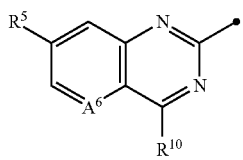
J1-2

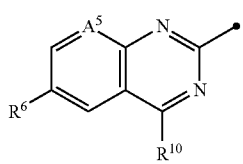
J1-3

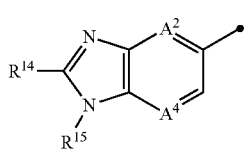
J2-1

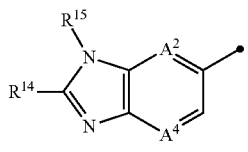
J3-1

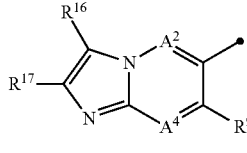
J5-1

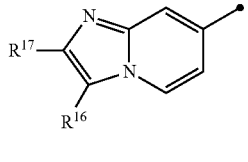
J6-1 wherein
A² is a nitrogen atom, CH or CCH₃,
A⁴ is a nitrogen atom or CH (wherein A² and A⁴ are not a nitrogen atom at the same time),
A⁵ is a nitrogen atom,
A⁶ is a nitrogen atom or CH,
R⁵ is a trifluoromethyl group,
R⁶ is a trifluoromethyl group,
R⁹ is a methyl group or a hydrogen atom,
R¹⁰ is a methyl group, an amino group, a methylamino group, an ethylamino group, a propylamino group, a chlorine atom, a bromine atom or a hydrogen atom,
R¹⁴ is a trifluoromethyl group,
R¹⁵ is a methyl group,
R¹⁶ is a hydrogen atom, and
R¹⁷ is a trifluoromethyl group or a pentafluoroethyl group.

Embodiment 4-1

In Embodiment 4, compounds wherein the partial structure is J1-1.

Embodiment 4-2

In Embodiment 4, compounds wherein the partial structure is J1-2.

Embodiment 4-3

In Embodiment 4, compounds wherein the partial structure is J1-3.

Embodiment 4-3-1

In Embodiment 4-3, compounds wherein R¹⁰ is a methyl group, an amino group, or a chlorine atom.

Embodiment 4-4

In Embodiment 4, compounds wherein the partial structure is J2-1.

Embodiment 4-5

In Embodiment 4, compounds wherein the partial structure is J3-1.

Embodiment 4-6

In Embodiment 4, compounds wherein the partial structure is J5-1.

Embodiment 4-7

In Embodiment 4, compounds wherein the partial structure is J6-1.

Embodiment 5

In the formula (1), compounds wherein
A¹ is CH,
R¹ is a C1 to C3 alkyl group (especially, an ethyl group),
R² and R⁴ are a hydrogen atom,
R³ is a halogen atom or a hydrogen atom, and partial structure:

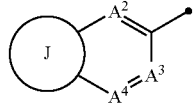

is the following J1-1 to J1-2, J2-1, J5-1, or J6-1:

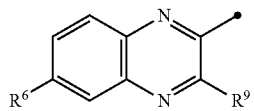
J1-1

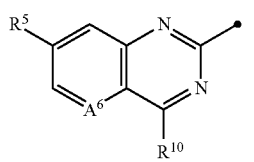
J1-2

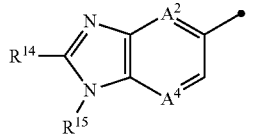
J2-1

-continued

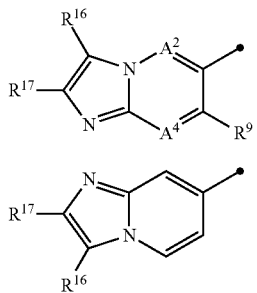

wherein
A² is a nitrogen atom, CH or CCH₃,
A⁴ is a nitrogen atom or CH (wherein A² and A⁴ are not a nitrogen atom at the same time),
A⁵ is a nitrogen atom,
A⁶ is a nitrogen atom or CH,
$R^5$ is a C1 to C3 haloalkyl group (especially, a C1 to C3 perfluoroalkyl group),
$R^6$ is a C1 to C3 haloalkyl group (especially, a C1 to C3 perfluoroalkyl group),
$R^9$ is a methyl group or a hydrogen atom,
$R^{10}$ is a C1 to C3 alkyl group (especially, a methyl group), an amino group having one C1 to C3 alkyl group, a halogen atom or a hydrogen atom,
$R^{14}$ is a C1 to C3 haloalkyl group (especially, a C1 to C3 perfluoroalkyl group),
$R^{15}$ is a C1 to C3 alkyl group (especially, a methyl group),
$R^{16}$ is a hydrogen atom, and
$R^{17}$ is a C1 to C3 haloalkyl group (especially, a C1 to C3 perfluoroalkyl group).

Embodiment 5-1

In Embodiment 5, compounds wherein the partial structure is J1-1.

Embodiment 5-2

In Embodiment 5, compounds wherein the partial structure is J1-2.

Embodiment 5-3

In Embodiment 5, compounds wherein the partial structure is J2-1.

Embodiment 5-4

In Embodiment 5, compounds wherein the partial structure is J5-1.

Embodiment 5-5

In Embodiment 5, compounds wherein the partial structure is J6-1.

Embodiment 6

In the formula (1), compounds wherein
A¹ is CH,
$R^1$ is an ethyl group,
$R^2$ and $R^4$ are a hydrogen atom,
$R^3$ is a chlorine atom or a hydrogen atom, and partial structure:

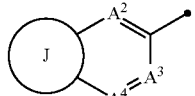

is the following J1-1 to J1-2, J2-1, J5-1, or J6-1:

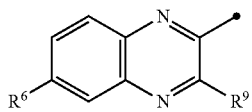

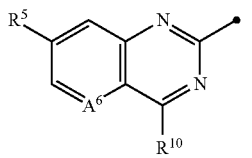

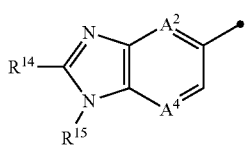

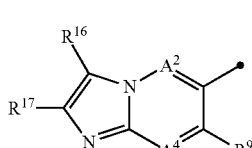

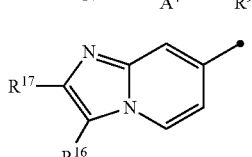

wherein
A² is a nitrogen atom, CH or CCH₃,
A⁴ is a nitrogen atom or CH (wherein A² and A⁴ are not a nitrogen atom at the same time),
A⁵ is a nitrogen atom,
A⁶ is a nitrogen atom or CH,
$R^5$ is a trifluoromethyl group,
$R^6$ is a trifluoromethyl group,
$R^9$ is a methyl group or a hydrogen atom,
$R^{10}$ is a methyl group, an amino group, an ethylamino group, a propylamino group or a hydrogen atom,
$R^{14}$ is a trifluoromethyl group,
$R^{15}$ is a methyl group,
$R^{16}$ is a hydrogen atom, and
$R^{17}$ is a trifluoromethyl group or a pentafluoroethyl group.

Embodiment 6-1

In Embodiment 6, compounds wherein the partial structure is J1-1.

Embodiment 6-2

In Embodiment 6, compounds wherein the partial structure is J1-2.

Embodiment 6-3

In Embodiment 6, compounds wherein the partial structure is J2-1.

Embodiment 6-4

In Embodiment 6, compounds wherein the partial structure is J5-1.

Embodiment 6-5

In Embodiment 6, compounds wherein the partial structure is J6-1.

Next, the method for producing the compound of the present invention will be described.

The compound of the present invention and an intermediate compound can be produced, for example, according to the following (Production Method 1) to (Production Method 11).

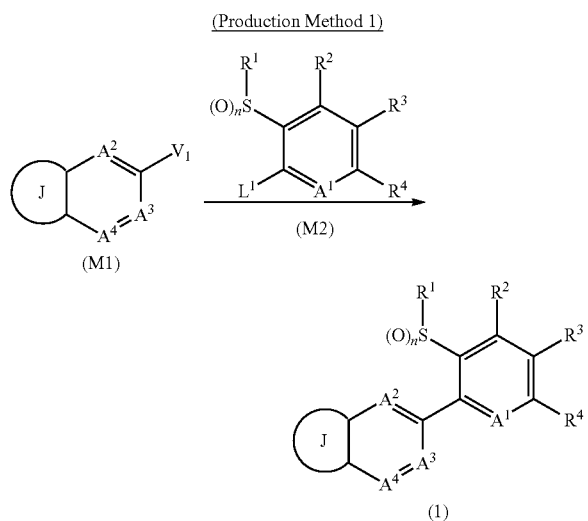

(Production Method 1)

The compound of the present invention (1) can be produced by reacting the intermediate compound (M1) with the intermediate compound (M2), in the presence of a catalyst and a base;
wherein $L^1$ represents a $B(OH)_2$ group or a $B(OR^f)_2$ group (wherein two $R^f$s combine to form a $—C(CH_3)_2C(CH_3)_2—$ group), $V^1$ represents a chlorine atom, a bromine atom or an iodide atom, and other symbols represent the same meaning as in the formula (1).

The reaction is usually carried out in the presence of a solvent.

Examples of the solvent include ethers such as tetrahydrofuran (hereinafter, referred to as THF), 1,2-dimethoxyethane (hereinafter, referred to as DME) a tert-butyl methyl ether and 1,4-dioxane, aromatic hydrocarbons such as toluene and xylene, aprotic polar solvents such as N,N-dimethylformamide (hereinafter, referred to as DMF), water, and mixtures thereof.

Examples of the catalyst include palladium catalysts such as tetrakis(triphenylphosphine)palladium, [1,1'-bis(diphenylphosphino)ferrocene]dichloropalladium complex with methylene chloride, and tris(dibenzylideneacetone)dipalladium(0).

The reaction can be also carried out by adding a ligand as necessary. Examples of the ligand include tricyclohexylphosphine and X-Phos(2-dicyclohexylphosphino-2',4',6'-triisopropylbiphenyl).

Examples of the base include inorganic bases such as sodium hydroxide, potassium hydroxide, potassium carbonate, cesium carbonate, potassium tert-butoxide and potassium phosphate, and organic bases such as sodium acetate and potassium acetate.

In the reaction, the intermediate compound (M2) is usually used in a ratio of 1 to 2 mol, the catalyst is usually used in a ratio of 0.0001 to 0.1 mol, the ligand is usually used in a ratio of 0.0002 to 0.2 mol, and the base is usually used in a ratio of 1 to 10 mol, based on 1 mol of the intermediate compound (M1).

The reaction temperature is usually within the range of 50 to 150° C. The reaction time is usually within the range of 0.1 to 24 hours.

After completion of the reaction, the compound of the present invention (1) can be isolated by subjecting it to normal post-process operations. The isolated compound of the present invention (1) also can be further purified by recrystallization, chromatography, or the like.

(Production Method 2)

The compound of the present invention (P1) in which J is J1, $A^2$ and $A^3$ are a nitrogen atom, and $A^4$ is $CR^{10'}$ (wherein $R^{10'}$ is a chlorine atom or a bromine atom) in the formula (1), and the compound of the present invention (P2) in which J is J1, $A^2$ and $A^3$ are a nitrogen atom, and $A^4$ is $CR^{10}$ in the formula (1) can be produced according to the following scheme:

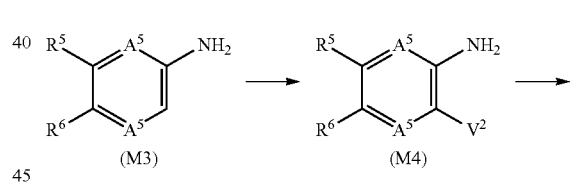

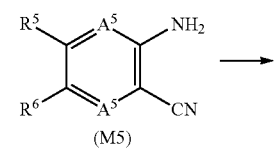

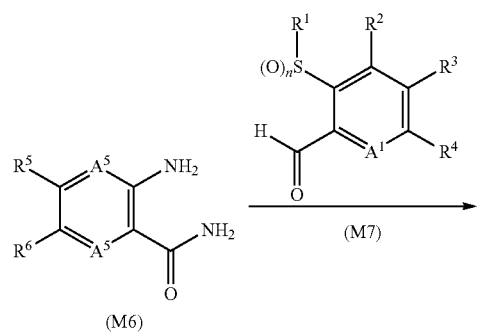

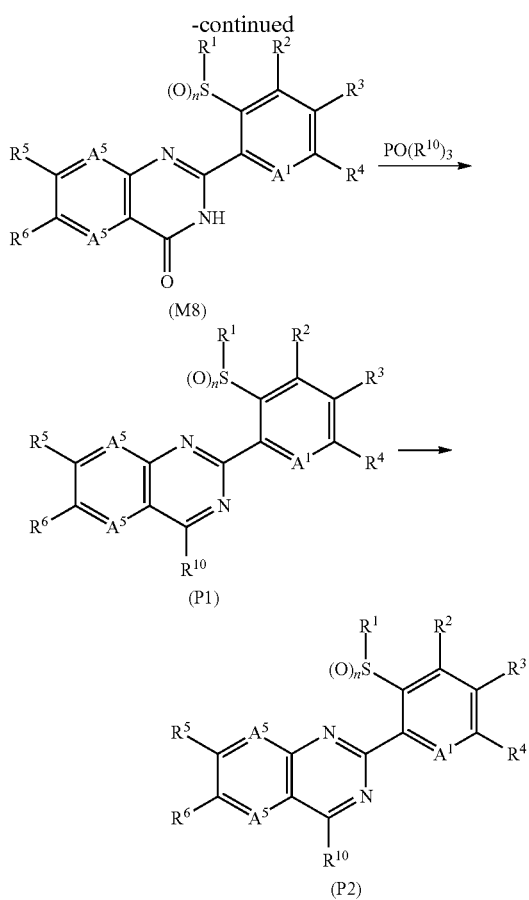

wherein $R^{10'}$ represents a chlorine atom or a bromine atom, $V^2$ represents a chlorine atom, a bromine atom or an iodine atom, and other symbols represent the same meaning as in the formula (1).

The intermediate compound (M4) can be produced by reacting the compound (M3) with a halogenating agent.

The reaction is usually carried out in the presence of a solvent.

Examples of the solvent include aliphatic halogenated hydrocarbons such as dichloromethane and chloroform, aromatic hydrocarbons such as toluene and xylene, ethers such as diethyl ether, THF, DME, tert-butyl methyl ether and 1,4-dioxane, aprotic polar solvents such as DMF, N-methyl pyrrolidone (hereinafter, referred to as NMP), 1,3-dimethyl-2-imidazolidinone (hereinafter, referred to as DMI), and dimethyl sulfoxide (hereinafter, referred to as DMSO), and mixtures thereof.

Examples of the halogenating agent include chlorine, bromine, iodine, N-chlorosuccinimide, N-bromosuccinimide, and N-iodosuccinimide.

In the reaction, the halogenating agent is usually used in a ratio of 1 to 2 mol, based on 1 mol of the compound (M3).

The reaction temperature is usually within the range of 0 to 150° C. The reaction time is usually within the range of 0.1 to 24 hours.

After completion of the reaction, the intermediate compound (M4) can be isolated by subjecting it to normal post-process operations. The isolated intermediate compound (M4) also can be further purified by chromatography, recrystallization, or the like.

The intermediate compound (M5) can be produced by reacting the intermediate compound (M4) with zinc cyanide, in the presence of a catalyst.

The reaction is usually carried out in the presence of a solvent.

Examples of the solvent used in the reaction include ethers such as THF, DME, tert-butyl methyl ether and 1,4-dioxane, aromatic hydrocarbons such as toluene and xylene, aprotic polar solvents such as DMF and NMP, and mixtures thereof.

Examples of the catalyst used in the reaction include palladium catalysts such as tetrakis(triphenylphosphine)palladium, and tris(dibenzylideneacetone)dipalladium(0).

The reaction can be also carried out by adding a ligand as necessary. Examples of the ligand include 1,1'-bis(diphenylphosphino)ferrocene.

In the reaction, zinc cyanide is usually used in a ratio of 1 to 2 mol, the catalyst is usually used in a ratio of 0.0001 to 0.1 mol, and the ligand is usually used in a ratio of 0.0002 to 0.2 mol, based on 1 mol of the intermediate compound (M4).

The reaction temperature is usually within the range of 50 to 150° C. The reaction time is usually within the range of 0.1 to 24 hours.

After completion of the reaction, the intermediate compound (M5) can be isolated by subjecting it to normal post-process operation. The intermediate compound (M5) can be also further purified by recrystallization, chromatography, or the like.

The intermediate compound (M6) can be produced by reacting the intermediate compound (M5) with hydrogen peroxide, in the presence of a base.

The reaction is usually carried out in the presence of a solvent.

Examples of the solvent include alcohols such as methanol and ethanol, DMSO, water, and mixtures thereof.

Examples of the base include alkali metal carbonates such as sodium carbonate and potassium carbonate, and alkali metal hydroxides such as sodium hydroxide and potassium hydroxide.

In the reaction, hydrogen peroxide is usually used in a ratio of 1 mol to an excess amount, and the base is usually used in a ratio of 1 mol to an excess amount, based on 1 mol of the intermediate compound (M5).

The reaction temperature is usually within the range of −10 to 100° C. The reaction time is usually within the range of 0.1 to 12 hours.

After completion of the reaction, the intermediate compound (M6) can be isolated by subjecting it to normal post-process operation. The isolated intermediate compound (M6) also can be further purified by chromatography, recrystallization, or the like.

The intermediate compound (M8) can be produced by condensing the intermediate compound (M6) and the compound (M7), in the presence of a sulfite.

The reaction is usually carried out in the presence of a solvent. Examples of the solvent include alcohols such as methanol and ethanol, ethers such as 1,4-dioxane, dimethyl ether, THF and tert-butyl methyl ether, aromatic hydrocarbons such as toluene, benzene and xylene, nitriles such as acetonitrile, aprotic polar solvents such as DMF, N,N-dimethylacetamide (hereinafter, referred to as DMA), and DMSO, water, and mixtures thereof.

Examples of the sulfite include sodium bisulfite and sodium disulfite.

The reaction can be also carried out by adding an acid, as necessary. Examples of the acid include sulfonic acids such as p-toluenesulfonic acid, carboxylic acids such as acetic acid, and polyphosphoric acid.

The reaction can be also carried out by adding an oxidizing agent, as necessary. Examples of the oxidizing agent include oxygen, copper(II) chloride, 2,3-dichloro-5,6-dicyano-p-benzoquinone, and potassium permanganate.

In the reaction, the compound (M7) is usually used in a ratio of 1 to 2 mol, the acid is usually used in a ratio of 0.1 to 2 mol, the sulfite is usually used in a ratio of 1 to 3 mol, and the oxidizing agent is usually used in a ratio of 1 to 3 mol, based on 1 mol of the intermediate compound (M6).

The reaction temperature is usually within the range of 0 to 200° C. The reaction time is usually within the range of 0.1 to 24 hours.

After completion of the reaction, the intermediate compound (M8) can be isolated by subjecting it to normal post-process operation. The isolated intermediate compound (M8) can be also further purified by recrystallization, chromatography, or the like.

The compound of the present invention (P1) can be produced by reacting the intermediate compound (M8) with phosphorus oxychloride or phosphorus oxybromide.

The reaction is usually carried out in the presence or absence of a solvent.

Examples of the solvent include nitriles such as acetonitrile and propionitrile, aromatic hydrocarbons such as toluene and xylene, and mixtures thereof.

The reaction can be also carried out by adding a base, as necessary. Examples of the base include tertiary amines such as triethylamine and N,N-diisopropylethylamine, and nitrogen-containing aromatic compounds such as pyridine.

In the reaction, phosphorus oxychloride or phosphorus oxybromide is usually used in a ratio of 1 to 3 mol, and the base is usually used in a ratio of 1 to 2 mol, based on 1 mol of the intermediate compound (M8).

The reaction temperature is usually within the range of 50 to 120° C. The reaction time is usually within the range of 0.1 to 24 hours.

After completion of the reaction, the compound of the present invention (P1) can be isolated by subjecting it to normal post-process operations. The isolated compound of the present invention (P1) also can be further purified by recrystallization, chromatography, or the like.

The compound of the present invention (P2) can be produced by reacting the compound of the present invention (P1) with an organic boron compound, an organic zinc compound, an organic silicon compound, an organic tin compound, alcohol, thiol, amine, or the like.

The reaction is usually carried out in the presence of a solvent.

Examples of the solvent include aliphatic halogenated hydrocarbons such as dichloromethane and chloroform, aromatic hydrocarbons such as toluene and xylene, ethers such as diethyl ether, THF, DME, tert-butyl methyl ether and 1,4-dioxane, aprotic polar solvents such as DMF, NMP, DMI and DMSO, water, and mixtures thereof.

The reaction can be also carried out by adding a catalyst, as necessary. Examples of the catalyst include palladium catalysts such as tetrakis(triphenylphosphine)palladium, [1,1'-bis(diphenylphosphino)ferrocene]dichloropalladium complex with methylene chloride, tris(dibenzylideneacetone)dipalladium(0) and palladium acetate, and copper catalysts such as copper(I) bromide and copper(I) iodide.

The reaction can be also carried out by adding a ligand as necessary. Examples of the ligand include tricyclohexylphosphine and X-Phos(2-dicyclohexylphosphino-2',4',6'-triisopropylbiphenyl).

The reaction can be also carried out by adding a base, as necessary. Examples of the base include inorganic bases such as sodium hydroxide, potassium hydroxide, potassium carbonate, cesium carbonate, potassium tert-butoxide and potassium phosphate, organic bases such as sodium acetate and potassium acetate, and tertiary amines such as triethylamine and N,N-diisopropylethylamine.

In the reaction, the organic boron compound, the organic zinc compound, the organic silicon compound, the organic tin compound, alcohol, thiol, amine or the like is usually used in a ratio of 1 to 3 mol, the catalyst is usually used in a ratio of 0.0001 to 1 mol, the ligand is usually used in a ratio of 0.0002 to 1 mol, and the base is usually used in a ratio of 1 to 10 mol, based on 1 mol of the compound of the present invention (P1).

The reaction temperature is usually within the range of 50 to 200° C. The reaction time is usually within the range of 0.1 to 24 hours.

After completion of the reaction, the compound of the present invention (P2) can be isolated by subjecting it to normal post-process operations. The isolated compound of the present invention (P2) also can be further purified by recrystallization, chromatography, or the like.

(Production Method 3)

The compound of the present invention (P3) in which J is J1, J2 or J3, $A^2$ is a nitrogen atom, $A^3$ is $CR^9$, and $A^4$ is $CR^{10}$ in the formula (1) can be produced by reacting the compound (M9) with the compound (M10), in the presence of a base:

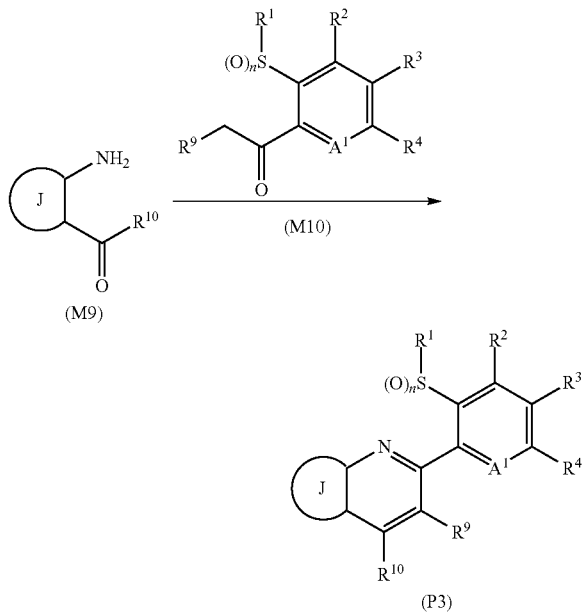

wherein symbols represent the same meaning as in the formula (1).

The reaction is usually carried out in the presence of a solvent.

Examples of the solvent include alcohols such as methanol and ethanol, water, and mixtures thereof.

Examples of the base include alkali metal hydroxides such as potassium hydroxide and sodium hydroxide, and metal alkoxides such as sodium ethoxide.

In the reaction, the compound (M10) is usually used in a ratio of 1 to 2 mol, and the base is usually used in a ratio of 1 to 10 mol, based on 1 mol of the compound (M9).

The reaction temperature is usually within the range of 50 to 100° C. The reaction time is usually within the range of 0.1 to 24 hours.

After completion of the reaction, the compound of the present invention (P3) can be isolated by subjecting it to normal post-process operations. The isolated compound of the present invention (P3) also can be further purified by recrystallization, chromatography, or the like.

(Production Method 4)

The compound of the present invention (P4) in which J is J1, J2 or J3, $A^2$ is CH, $A^3$ is $CR^{9'}$ (wherein $R^{9'}$ is a chlorine atom or a bromine atom), and $A^4$ is a nitrogen atom in the formula (1), and the compound of the present invention (P5) in which J is J1, J2 or J3, $A^2$ is CH, $A^3$ is $CR^9$, and $A^4$ is a nitrogen atom in the formula (1) can be produced according to the following scheme:

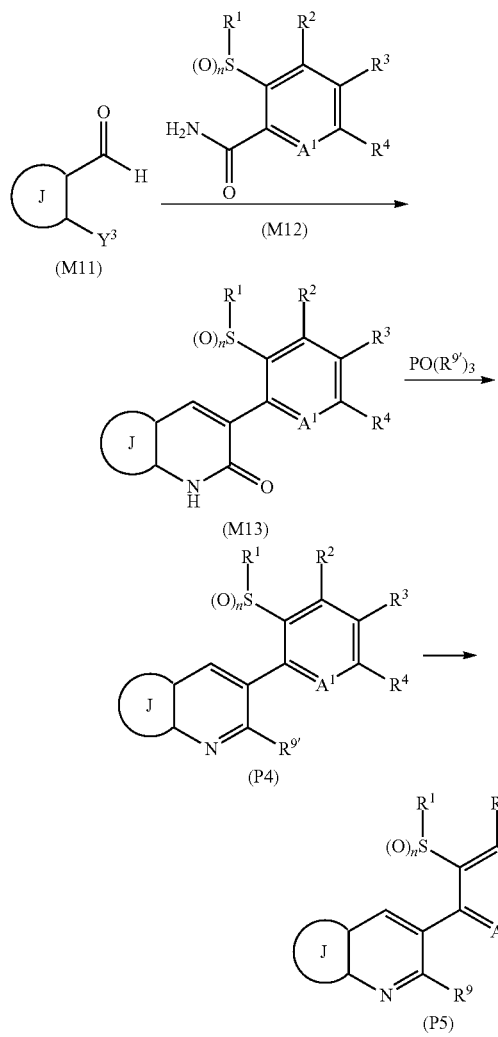

wherein $R^{9'}$ represents a chlorine atom or a bromine atom, $V^3$ represents a bromine atom or an iodine atom, and other symbols represent the same meaning as in the formula (1).

The intermediate compound (13) can be produced by reacting the compound (M11) with the compound (M12), in the presence of a catalyst and a base.

The reaction is usually carried out in the presence of a solvent.

Examples of the solvent used in the reaction include aromatic hydrocarbons such as toluene and xylene, aprotic polar solvents such as DMF, and mixtures thereof.

Examples of the catalyst used in the reaction include palladium catalysts such as tris(dibenzylideneacetone)dipalladium(0).

The reaction can be also carried out by adding a ligand as necessary. Examples of the ligand include Xantphos and X-Phos(2-dicyclohexylphosphino-2',4',6'-triisopropylbiphenyl).

Examples of the base used in the reaction include inorganic bases such as potassium carbonate, cesium carbonate, potassium tert-butoxide and potassium phosphate.

In the reaction, the compound (M12) is usually used in a ratio of 1 to 2 mol, the catalyst is usually used in a ratio of 0.0001 to 0.1 mol, the ligand is usually used in a ratio of 0.0002 to 0.2 mol, and the base is usually used in a ratio of 1 to 10 mol, based on 1 mol of the compound (M11).

The reaction temperature is usually within the range of 50 to 150° C. The reaction time is usually within the range of 0.1 to 24 hours.

After completion of the reaction, the intermediate compound (M13) can be isolated by subjecting it to normal post-process operation. The isolated compound of the present invention (M13) also can be further purified by recrystallization, chromatography, or the like.

The compound of the present invention (P4) can be produced, using the intermediate compound (M13) in place of the intermediate compound (M8), in accordance with the method of Production Method 2.

The compound of the present invention (P5) can be produced, using the compound of the present invention (P4) in place of the compound of the present invention (P1), in accordance with the method of Production Method 2.

(Production Method 5)

The compound of the present invention (P6) in which J is J5, $B^4$ is $CR^{16}$, $B^5$ is $CR^{17}$, and $B^6$ is a nitrogen atom in the formula (1) can be produced according to the following scheme:

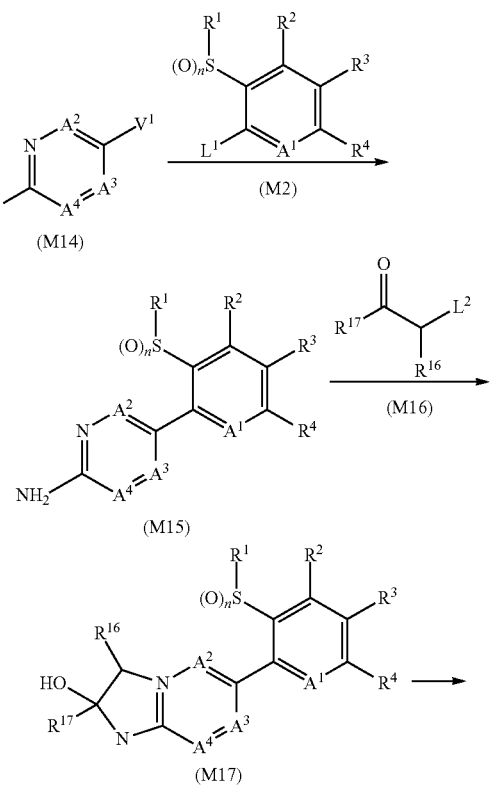

-continued

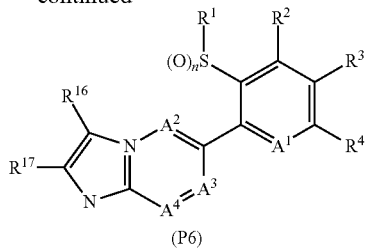

(P6)

wherein $L^1$ represents a $B(OH)_2$ group or a $B(OR^f)_2$ group (wherein two $R^f$s combine to form a —$C(CH_3)_2C(CH_3)_2$— group), $V^1$ represents a chlorine atom, a bromine atom or an iodide atom, $L^2$ represents a chlorine atom or a bromine atom, and other symbols represent the same meaning as in the formula (1).

The intermediate compound (M15) can be produced, using the compound (M14) in place of the intermediate compound (M1), in accordance with the method of Production Method 1.

Also, the intermediate compound (M17) can be produced by reacting the intermediate compound (M15) with the compound (M16).

The reaction is usually carried out in the presence or absence of a solvent.

Examples of the solvent include ethers such as THF, DME, tert-butyl methyl ether and 1,4-dioxane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, and mixtures thereof.

The reaction can be also carried out by adding a base, as necessary.

Examples of the base include alkali metal carbonates such as sodium carbonate and potassium carbonate, and alkali metal bicarbonates such as sodium bicarbonate.

In the reaction, the compound (M16) is usually used in a ratio of 1 to 3 mol, and the base is usually used in a ratio of 1 to 3 mol, based on 1 mol of the intermediate compound (M15).

The reaction temperature in the reaction is usually within the range of 20 to 200° C. The reaction time is usually within the range of 0.1 to 24 hours.

After completion of the reaction, the intermediate compound (M17) can be isolated by subjecting it to normal post-process operation. The isolated intermediate compound (M17) can be also further purified by recrystallization, chromatography, or the like. Alternatively, the intermediate compound (M17) can be also used in the next reaction as it is without isolation and purification.

The compound of the present invention (P6) can be produced by subjecting the intermediate compound (M17) to a dehydration reaction.

The reaction is usually carried out in the presence or absence of a solvent.

Examples of the solvent include ethers such as THF, DME, tert-butyl methyl ether and 1,4-dioxane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, and mixtures thereof.

The reaction temperature is usually within the range of 50 to 200° C. The reaction time in the reaction is usually within the range of 0.1 to 24 hours.

After completion of the reaction, the compound of the present invention (P6) can be isolated by subjecting it to normal post-process operations. The isolated intermediate compound, the compound of the present invention (P6) also can be further purified by recrystallization, chromatography, or the like.

(Production Method 6)

The compound of the present invention (P7) in which J is J6, $B^4$ is $CR^{16}$, $B^5$ is $CR^{17}$, and $B^6$ is a nitrogen atom in the formula (1) can be produced according to the following scheme:

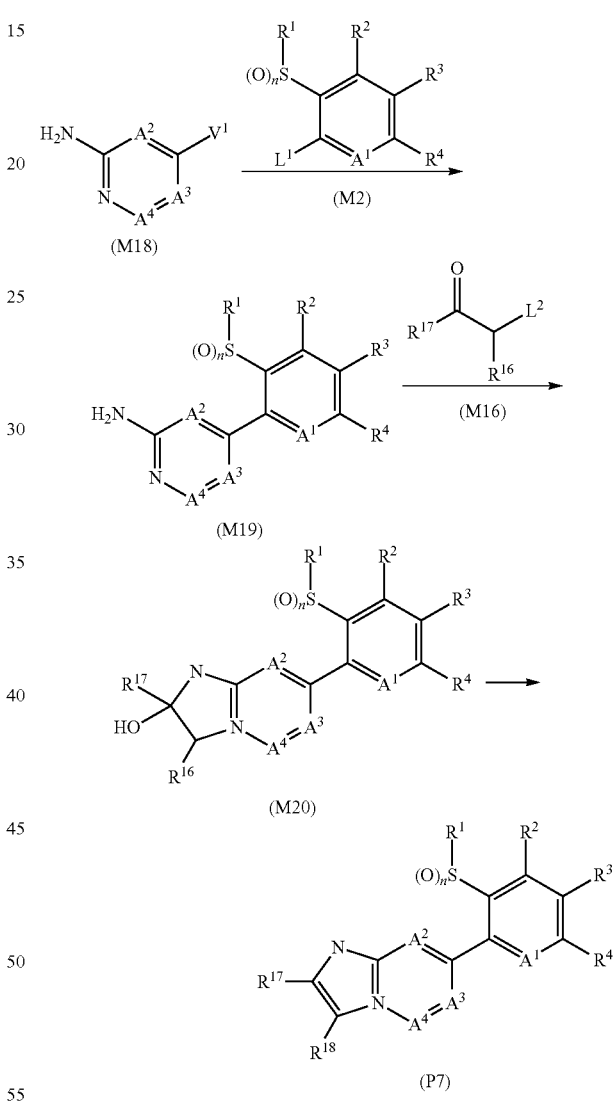

wherein $L^1$ represents a $B(OH)_2$ group or a $B(OR^f)_2$ group (wherein two $R^f$s combine to form a —$C(CH_3)_2C(CH_3)_2$— group), $V^1$ represents a chlorine atom, a bromine atom or an iodide atom, $L^2$ represents a chlorine atom or a bromine atom, and other symbols represent the same meaning as in the formula (1).

The intermediate compound (M19) can be produced, using the compound (M18) in place of the intermediate compound (M1), in accordance with the method of Production Method 1.

The intermediate compound (M20) can be produced, using the intermediate compound (M19) in place of the intermediate compound (M15), in accordance with the method of Production Method 5.

The compound of the present invention (P7) can be produced, using the intermediate compound (M20) in place of the intermediate compound (M17), in accordance with the method of Production Method 5.

(Production Method 7)

The intermediate compound (M2) can be produced according to the following scheme:

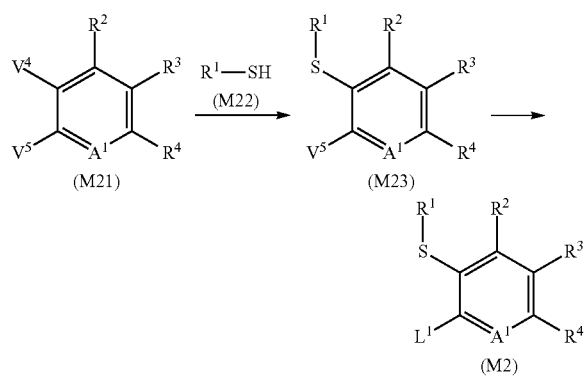

wherein $L^1$ represents a $B(OH)_2$ group or a $B(OR^f)_2$ group (wherein two $R^f$s combine to form a $-C(CH_3)_2C(CH_3)_2-$ group), $V^4$ represents a fluorine atom, a chlorine atom or a bromine atom, $V^5$ represents a bromine atom or an iodine atom, and other symbols represent the same meaning as in the formula (1).

The intermediate compound (M23) can be produced by reacting the compound (M21) with the compound (M22), in the presence of a base.

The reaction is usually carried out in the presence of a solvent.

Examples of the solvent used in the reaction include ethers such as THF, DME, tert-butyl methyl ether and 1,4-dioxane, alcohols such as methanol and ethanol, aromatic hydrocarbons such as toluene and xylene, nitriles such as acetonitrile, aprotic polar solvents such as DMF, NMP, DMI and DMSO, water, and mixtures thereof.

Examples of the base used in the reaction include hydrides of alkali metals or alkaline earth metals such as sodium hydride, potassium hydride and calcium hydride, inorganic bases such as sodium carbonate and potassium carbonate, or organic bases such as triethylamine. In the reaction, the compound (M22) is usually used in a ratio of 0.8 to 1.2 mol, and the base is usually used in a ratio of 0.8 to 1.2 mol, based on 1 mol of the compound (M21).

The reaction temperature is usually within the range of 0 to 100° C. The reaction time is usually within the range of 0.1 to 24 hours.

After completion of the reaction, the intermediate compound (M23) can be isolated by subjecting it to normal post-process operation. The intermediate compound (M23) also can be further purified by chromatography, recrystallization, or the like.

In the reaction, $V^4$ is preferably a fluorine atom or a chlorine atom.

The intermediate compound (M2) can be produced by reacting a reaction intermediate produced after reacting the intermediate compound (M23) with an alkyl lithium compound, with isopropoxyboronic acid pinacol ester, or reacting the produced reaction intermediate with trialkyl borate, and then hydrolyzing the reaction mixture.

The reaction is usually carried out in the presence of a solvent.

Examples of the solvent include ethers such as diethyl ether, THF, DME, t-butyl methyl ether and 1,4-dioxane, aromatic hydrocarbons such as toluene and xylene, and mixtures thereof.

Examples of the alkyl lithium compound used in the reaction include n-, sec- or tert-butyl lithium.

Examples of the trialkyl borate used in the reaction include trimethyl borate, triethyl borate, and triisopropyl borate.

In the reaction, the alkyl lithium compound is usually used in a ratio of 1 mol, based on 1 mol of the intermediate compound (M23), but the ratio can be appropriately changed.

In the reaction, isopropoxyboronic acid pinacol ester or trialkyl borate is usually used in a ratio of 1 mol, based on 1 mol of the intermediate compound (M23), but the ratio can be appropriately changed.

The reaction temperature in the reaction of the intermediate compound (M23) with the alkyl lithium compound is usually within the range of −78 to 20° C. The reaction time is usually within the range of 0.1 to 12 hours.

The reaction temperature in the reaction of the reaction intermediate with isopropoxyboronic acid pinacol ester or trialkyl borate is usually within the range of −78 to 40° C. The reaction time is usually within the range of 0.1 to 24 hours.

After completion of the reaction, the intermediate compound (M2) can be isolated by subjecting it to normal post-process operations. The isolated intermediate compound (M2) can be also further purified by recrystallization, chromatography, or the like.

The intermediate compound (M2) in which L is a $B(OR^f)_2$ group (wherein two $R^f$s combine to form a $-C(CH_3)_2C(CH_3)_2-$ group) can be produced by reacting the intermediate compound (M23) with bis(pinacolato)diboron, in the presence of a catalyst and a base.

The reaction is usually carried out in the presence of a solvent.

Examples of the solvent include ethers such as THF, DME, tert-butyl methyl ether and 1,4-dioxane, aromatic hydrocarbons such as toluene and xylene, and mixtures thereof.

Examples of the catalyst include palladium catalysts such as tetrakis(triphenylphosphine)palladium, [1,1'-bis(diphenylphosphino)ferrocene]dichloropalladium complex with methylene chloride, and tris(dibenzylideneacetone)dipalladium(0).

The reaction can be also carried out by adding a ligand as necessary. Examples of the ligand include tricyclohexylphosphine.

Examples of the base used in the reaction include potassium acetate.

In the reaction, bis(pinacolato)diboron is usually used in a ratio of 1 to 2 mol, the catalyst is usually used in a ratio of 0.0001 to 0.1 mol, the ligand is usually used in a ratio of 0.0002 to 0.2 mol, and the base is usually used in a ratio of 1 to 5 mol, based on 1 mol of the intermediate compound (M23).

The reaction temperature is usually within the range of 50 to 120° C. The reaction time is usually within the range of 0.1 to 24 hours.

After completion of the reaction, the intermediate compound (M2) can be isolated by subjecting it to normal post-process operations. The isolated intermediate compound (M2) can be also further purified by recrystallization, chromatography, or the like.

(Production Method 8)

The intermediate compounds (M1-1) and (M1-2) can be produced according to the following scheme:

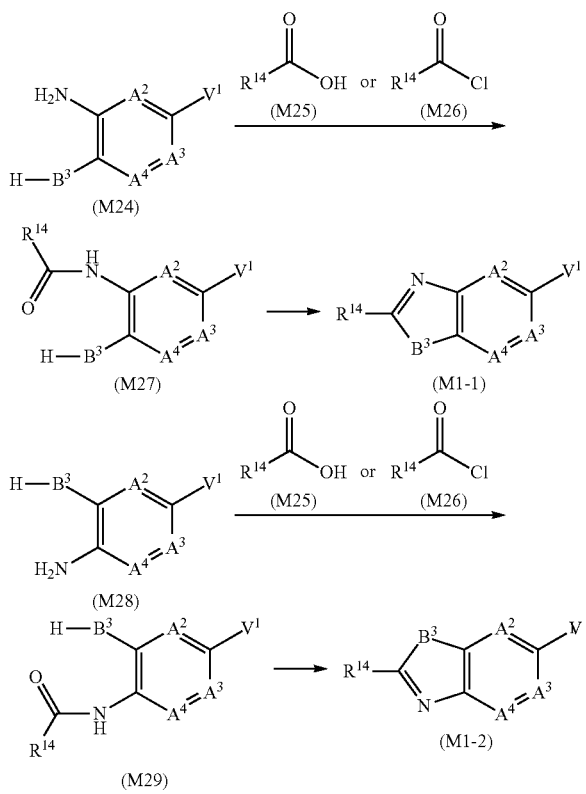

wherein $V^1$ represents a chlorine atom, a bromine atom or an iodine atom, and other symbols represent the same meaning as in the formula (1).

The intermediate compound (M27) can be produced by reacting the compound (M24) with the compound (M25), in the presence of a condensing agent.

The reaction is usually carried out in the presence of a solvent. Examples of the solvent used in the reaction include ethers such as 1,4-dioxane, diethyl ether, tetrahydrofuran (hereinafter, referred to as THF) and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

Examples of the condensing agent used in the reaction include carbodiimides such as 1-ethyl-3-(3-dimethylaminopropyl) carbodiimide hydrochloride (hereinafter, referred to as EDCI hydrochloride) and 1,3-dicyclohexylcarbodiimide and benzotriazol-1-yloxy-tris(dimethylamino)phosphonium hexafluorophosphate.

The reaction can be also carried out by adding a catalyst, as necessary. Examples of the catalyst include 1-hydroxybenzotriazole.

In the reaction, the compound (M25) is usually used in a ratio of 1 to 3 mol, the condensing agent is usually used in a ratio of 1 to 5 mol, and the catalyst is usually used in a ratio of 0.01 to 1 mol, based on 1 mol of the compound (M24).

The reaction temperature is usually within the range of 0 to 120° C. The reaction time is usually within the range of 0.1 to 24 hours.

After completion of the reaction, the intermediate compound (M27) can be isolated by subjecting it to normal post-process operations. The isolated intermediate compound (M27) also can be further purified by recrystallization, chromatography, or the like. Alternatively, the intermediate compound (M27) can be also used in the next reaction as it is without isolation and purification.

Also, the intermediate compound (M27) can be produced by reacting the compound (M24) with the compound (M26).

The reaction is usually carried out in the presence of a solvent.

Examples of the solvent include ethers such as THF, DME, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, and mixtures thereof.

The reaction can be also carried out by adding a base, as necessary. The base includes alkali metal carbonates such as sodium carbonate and potassium carbonate, tertiary amines such as triethylamine and N,N-diisopropylethylamine, and nitrogen-containing aromatic compounds such as pyridine.

In the reaction, the compound (M26) is usually used in a ratio of 1 to 3 mol, and the base is usually used in a ratio of 1 to 5 mol, based on 1 mol of the compound (M24).

The reaction temperature is usually within the range of −20 to 100° C. The reaction time is usually within the range of 0.1 to 24 hours.

After completion of the reaction, the intermediate compound (M27) can be isolated by subjecting it to normal post-process operations. The isolated intermediate compound (M27) also can be further purified by recrystallization, chromatography, or the like. Alternatively, the intermediate compound (M27) can be also used in the next reaction as it is without isolation and purification.

The intermediate compound (M1-1) can be produced by intramolecular condensation of the intermediate compound (M27).

The reaction is usually carried out in the presence of a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

The reaction can use a condensing agent, an acid, a base or a chlorinating agent, as necessary.

Examples of the condensing agent used in the reaction include a mixture of acetic anhydride, trifluoroacetic anhydride, EDCI hydrochloride, a mixture of triphenylphosphine, a base and carbon tetrachloride or carbon tetrabromide, and a mixture of triphenylphosphine and azodiesters such as diethyl azodicarboxylate.

Examples of the acid include sulfonic acids such as p-toluenesulfonic acid, carboxylic acids such as acetic acid, polyphosphoric acid, and the like.

Examples of the base include nitrogen-containing heterocyclic compounds such as pyridine, picoline, 2,6-lutidine, 1,8-diazabicyclo[5.4.0]-7-undecene and 1,5-diazabicyclo[4.3.0]-5-nonene, tertiary amines such as triethylamine and N,N-diisopropylethylamine, and inorganic bases such as tripotassium phosphate, potassium carbonate and sodium hydride.

Examples of the chlorinating agent used in the reaction include phosphorus oxychloride and the like.

In the reaction, when a condensing agent is used, the condensing agent is usually used in a ratio of 1 to 5 mol, when an acid is used, the acid is usually used in a ratio of 0.1 to 5 mol, when a base is used, the base is usually used in a ratio of 1 to 5 mol, and when a chlorinating agent is used, the chlorinating agent is usually used in a ratio of 1 to 5 mol, based on 1 mol of the intermediate compound (M27).

The reaction temperature is usually within the range of 0 to 200° C. The reaction time is usually within the range of 0.1 to 24 hours.

After completion of the reaction, the intermediate compound (M1-1) can be isolated by subjecting it to normal post-process operation. The isolated intermediate compound (M1-1) also can be further purified by recrystallization, chromatography, or the like.

The intermediate compound (M29) can be produced, using the compound (M28) in place of the compound (M24), in accordance with the method of Production Method 8.

The intermediate compound (M1-2) can be produced, using the compound (M29) in place of the compound (M27), in accordance with the method of Production Method 8.

(Production Method 9)

The intermediate compounds (M1-3) and (M1-4) can be produced according to the following scheme:

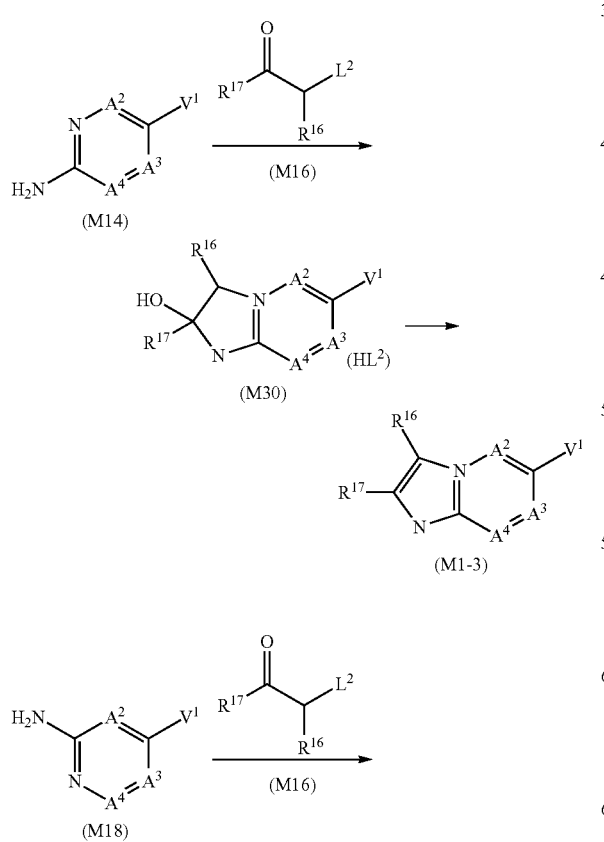

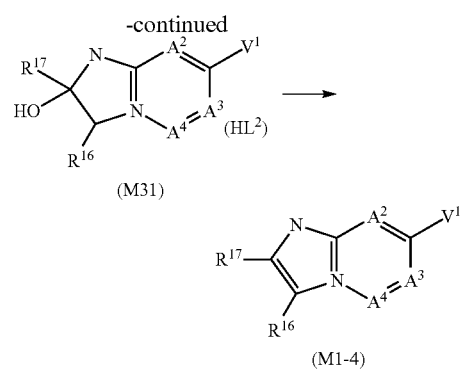

wherein $L^2$ represents a chlorine atom or a bromine atom, $V^1$ represents a chlorine atom, a bromine atom or an iodine atom, and other symbols represent the same meaning as in the formula (1).

The intermediate compound (M30) can be produced, using the compound (M14) in place of the intermediate compound (M15), in accordance with the method of Production Method 5. When a base is not used for the reaction and purification, the intermediate compound (M30) can be obtained as a hydrochloride or hydrobromide.

The intermediate compound (M1-3) can be produced, using the intermediate compound (M30) in place of the intermediate compound (M17), in accordance with the method of Production Method 5.

The intermediate compound (M31) can be produced, using the compound (M18) in place of the intermediate compound (M15), in accordance with the method of Production Method 5. When a base is not used for the reaction and purification, the intermediate compound (M31) can be obtained as a hydrochloride or hydrobromide.

The intermediate compound (M1-4) can be produced, using the intermediate compound (M31) in place of the intermediate compound (M17), in accordance with the method of Production Method 5.

The compound of the present invention in which n is 1 or 2 in the formula (1) can be produced by oxidizing the compound of the present invention in which n is 0:

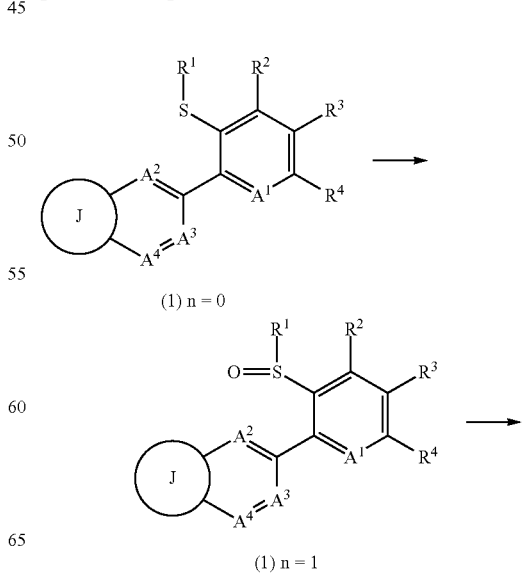

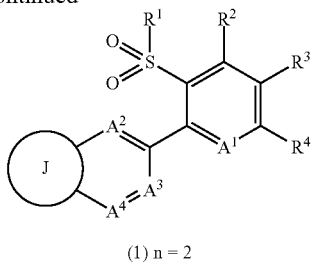

(1) n = 2 wherein symbols represent the same meaning as in the formula (1).

The compound of the present invention (1-n1) in which n is 1 in the formula (1) can be produced by oxidizing the compound of the present invention (1-n0) in which n is 0 with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperbenzoic acid. In the reaction, the oxidizing agent is usually used in a ratio of 1 to 3 mol, based on 1 mol of 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of −20 to 80° C. The reaction time is usually within the range of 0.1 to 12 hours.

After completion of the reaction, the compound of the present invention (1-n1) can be isolated by subjecting it to normal post-process operations. The isolated compound of the present invention (1-n1) also can be further purified by chromatography, recrystallization, or the like.

The compound of the present invention (1-n2) in which n is 2 in the formula (1) can be produced by oxidizing the compound of the present invention (1-n1) in which n is 1 with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 1 to 4 mol, based on 1 mol of the compound of the present invention (1-n1). Preferably, the oxidizing agent is used in a ratio of 1 to 2 mol, based on 1 mol of the compound of the present invention (1-n1).

The reaction temperature is usually within the range of −20 to 120° C. The reaction time is usually within the range of 0.1 to 12 hours.

After completion of the reaction, the compound of the present invention (1-n2) can be isolated by subjecting it to normal post-process operations. The compound of the present invention (1-n2) also can be further purified by chromatography, recrystallization, or the like.

The compound of the present invention (1-n2) in which n is 2 in the formula (1) can be produced by a one step reaction (one pot) by oxidizing the compound of the present invention (1-n0) in which n is 0 with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 2 to 5 mol, based on 1 mol of the compound of the present invention (1-n0). Preferably, the oxidizing agent is used in a ratio of 2 to 3 mol, based on 1 mol of the compound of the present invention (1-n0).

The reaction temperature is usually within the range of 0 to 120° C. The reaction time is usually within the range of 0.1 to 12 hours.

After completion of the reaction, the compound of the present invention (1-n2) can be isolated by subjecting it to normal post-process operations. The isolated compound of the present invention (1-n2) also can be further purified by chromatography, recrystallization, or the like.

(Production Method 11)

Among the compounds of the present invention and the above-described intermediate compounds, a compound having a nitrogen-containing heterocyclic group having a lone pair of electrons on the nitrogen atom is reacted with an oxidizing agent, whereby an N-oxide in which the nitrogen atom is oxidized can be manufactured in some cases.

Examples of the nitrogen-containing heterocyclic group include a pyridine ring, and condensed rings containing a pyridine ring.

The reaction can be carried out by a known method, and is carried out using an oxidizing agent such as m-chloroperbenzoic acid or hydrogen peroxide, in a solvent, for example, a halogenated hydrocarbon such as dichloromethane, chloroform or chlorobenzene, an alcohol such as methanol or ethanol, acetic acid, water, and mixtures thereof.

Next, specific examples of the compound of the present invention are shown below.

In formula (A):

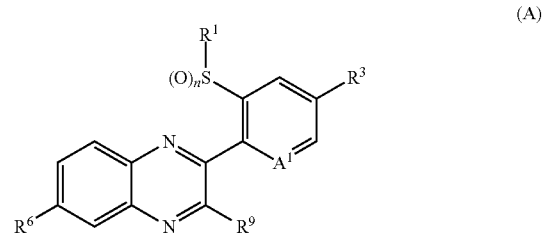

(A)

wherein symbols represent the same meaning as in the formula (1), the compounds of the present invention wherein $R^6$ is a trifluoromethyl group, $R^9$ is a hydrogen atom, and $R^1$, $R^3$, $A^1$ and n are the combinations shown in [Table 1] to [Table 16].

TABLE 1

| $R^1$ | $R^3$ | $A^1$ | n |
|---|---|---|---|
| Me | H | N | 0 |
| Me | H | N | 1 |

TABLE 1-continued

| $R^1$ | $R^3$ | $A^1$ | n |
|---|---|---|---|
| Me | H | N | 2 |
| Me | F | N | 0 |
| Me | F | N | 1 |
| Me | F | N | 2 |
| Me | Cl | N | 0 |
| Me | Cl | N | 1 |
| Me | Cl | N | 2 |
| Me | Br | N | 0 |
| Me | Br | N | 1 |
| Me | Br | N | 2 |
| Me | $CF_3$ | N | 0 |
| Me | $CF_3$ | N | 1 |
| Me | $CF_3$ | N | 2 |
| Me | $CF_2CF_3$ | N | 0 |
| Me | $CF_2CF_3$ | N | 1 |
| Me | $CF_2CF_3$ | N | 2 |
| Me | $OCF_3$ | N | 0 |
| Me | $OCF_3$ | N | 1 |
| Me | $OCF_3$ | N | 2 |
| Me | $SCF_3$ | N | 0 |
| Me | $SCF_3$ | N | 1 |
| Me | $SCF_3$ | N | 2 |
| Me | $S(O)CF_3$ | N | 0 |
| Me | $S(O)CF_3$ | N | 1 |
| Me | $S(O)CF_3$ | N | 2 |
| Me | $S(O)_2CF_3$ | N | 0 |
| Me | $S(O)_2CF_3$ | N | 1 |
| Me | $S(O)_2CF_3$ | N | 2 |

TABLE 2

| $R^1$ | $R^3$ | $A^1$ | n |
|---|---|---|---|
| Et | H | N | 0 |
| Et | H | N | 1 |
| Et | H | N | 2 |
| Et | F | N | 0 |
| Et | F | N | 1 |
| Et | F | N | 2 |
| Et | Cl | N | 0 |
| Et | Cl | N | 1 |
| Et | Cl | N | 2 |
| Et | Br | N | 0 |
| Et | Br | N | 1 |
| Et | Br | N | 2 |
| Et | $CF_3$ | N | 0 |
| Et | $CF_3$ | N | 1 |
| Et | $CF_3$ | N | 2 |
| Et | $CF_2CF_3$ | N | 0 |
| Et | $CF_2CF_3$ | N | 1 |
| Et | $CF_2CF_3$ | N | 2 |
| Et | $OCF_3$ | N | 0 |
| Et | $OCF_3$ | N | 1 |
| Et | $OCF_3$ | N | 2 |
| Et | $SCF_3$ | N | 0 |
| Et | $SCF_3$ | N | 1 |
| Et | $SCF_3$ | N | 2 |
| Et | $S(O)CF_3$ | N | 0 |
| Et | $S(O)CF_3$ | N | 1 |
| Et | $S(O)CF_3$ | N | 2 |
| Et | $S(O)_2CF_3$ | N | 0 |
| Et | $S(O)_2CF_3$ | N | 1 |
| Et | $S(O)_2CF_3$ | N | 2 |

TABLE 3

| $R^1$ | $R^3$ | $A^1$ | n |
|---|---|---|---|
| Pr | H | N | 0 |
| Pr | H | N | 1 |
| Pr | H | N | 2 |
| Pr | F | N | 0 |
| Pr | F | N | 1 |

TABLE 3-continued

| $R^1$ | $R^3$ | $A^1$ | n |
|---|---|---|---|
| Pr | F | N | 2 |
| Pr | Cl | N | 0 |
| Pr | Cl | N | 1 |
| Pr | Cl | N | 2 |
| Pr | Br | N | 0 |
| Pr | Br | N | 1 |
| Pr | Br | N | 2 |
| Pr | $CF_3$ | N | 0 |
| Pr | $CF_3$ | N | 1 |
| Pr | $CF_3$ | N | 2 |
| Pr | $CF_2CF_3$ | N | 0 |
| Pr | $CF_2CF_3$ | N | 1 |
| Pr | $CF_2CF_3$ | N | 2 |
| Pr | $OCF_3$ | N | 0 |
| Pr | $OCF_3$ | N | 1 |
| Pr | $OCF_3$ | N | 2 |
| Pr | $SCF_3$ | N | 0 |
| Pr | $SCF_3$ | N | 1 |
| Pr | $SCF_3$ | N | 2 |
| Pr | $S(O)CF_3$ | N | 0 |
| Pr | $S(O)CF_3$ | N | 1 |
| Pr | $S(O)CF_3$ | N | 2 |
| Pr | $S(O)_2CF_3$ | N | 0 |
| Pr | $S(O)_2CF_3$ | N | 1 |
| Pr | $S(O)_2CF_3$ | N | 2 |

TABLE 4

| $R^1$ | $R^3$ | $A^1$ | n |
|---|---|---|---|
| iPr | H | N | 0 |
| iPr | H | N | 1 |
| iPr | H | N | 2 |
| iPr | F | N | 0 |
| iPr | F | N | 1 |
| iPr | F | N | 2 |
| iPr | Cl | N | 0 |
| iPr | Cl | N | 1 |
| iPr | Cl | N | 2 |
| iPr | Br | N | 0 |
| iPr | Br | N | 1 |
| iPr | Br | N | 2 |
| iPr | $CF_3$ | N | 0 |
| iPr | $CF_3$ | N | 1 |
| iPr | $CF_3$ | N | 2 |
| iPr | $CF_2CF_3$ | N | 0 |
| iPr | $CF_2CF_3$ | N | 1 |
| iPr | $CF_2CF_3$ | N | 2 |
| iPr | $OCF_3$ | N | 0 |
| iPr | $OCF_3$ | N | 1 |
| iPr | $OCF_3$ | N | 2 |
| iPr | $SCF_3$ | N | 0 |
| iPr | $SCF_3$ | N | 1 |
| iPr | $SCF_3$ | N | 2 |
| iPr | $S(O)CF_3$ | N | 0 |
| iPr | $S(O)CF_3$ | N | 1 |
| iPr | $S(O)CF_3$ | N | 2 |
| iPr | $S(O)_2CF_3$ | N | 0 |
| iPr | $S(O)_2CF_3$ | N | 1 |
| iPr | $S(O)_2CF_3$ | N | 2 |

TABLE 5

| $R^1$ | $R^3$ | $A^1$ | n |
|---|---|---|---|
| cyPr | H | N | 0 |
| cyPr | H | N | 1 |
| cyPr | H | N | 2 |
| cyPr | F | N | 0 |
| cyPr | F | N | 1 |
| cyPr | F | N | 2 |
| cyPr | Cl | N | 0 |
| cyPr | Cl | N | 1 |

TABLE 5-continued

| R¹ | R³ | A¹ | n |
|---|---|---|---|
| cyPr | Cl | N | 2 |
| cyPr | Br | N | 0 |
| cyPr | Br | N | 1 |
| cyPr | Br | N | 2 |
| cyPr | CF₃ | N | 0 |
| cyPr | CF₃ | N | 1 |
| cyPr | CF₃ | N | 2 |
| cyPr | CF₂CF₃ | N | 0 |
| cyPr | CF₂CF₃ | N | 1 |
| cyPr | CF₂CF₃ | N | 2 |
| cyPr | OCF₃ | N | 0 |
| cyPr | OCF₃ | N | 1 |
| cyPr | OCF₃ | N | 2 |
| cyPr | SCF₃ | N | 0 |
| cyPr | SCF₃ | N | 1 |
| cyPr | SCF₃ | N | 2 |
| cyPr | S(O)CF₃ | N | 0 |
| cyPr | S(O)CF₃ | N | 1 |
| cyPr | S(O)CF₃ | N | 2 |
| cyPr | S(O)₂CF₃ | N | 0 |
| cyPr | S(O)₂CF₃ | N | 1 |
| cyPr | S(O)₂CF₃ | N | 2 |

TABLE 6

| R¹ | R³ | A¹ | n |
|---|---|---|---|
| CH₂cyPr | H | N | 0 |
| CH₂cyPr | H | N | 1 |
| CH₂cyPr | H | N | 2 |
| CH₂cyPr | F | N | 0 |
| CH₂cyPr | F | N | 1 |
| CH₂cyPr | F | N | 2 |
| CH₂cyPr | Cl | N | 0 |
| CH₂cyPr | Cl | N | 1 |
| CH₂cyPr | Cl | N | 2 |
| CH₂cyPr | Br | N | 0 |
| CH₂cyPr | Br | N | 1 |
| CH₂cyPr | Br | N | 2 |
| CH₂cyPr | CF₃ | N | 0 |
| CH₂cyPr | CF₃ | N | 1 |
| CH₂cyPr | CF₃ | N | 2 |
| CH₂cyPr | CF₂CF₃ | N | 0 |
| CH₂cyPr | CF₂CF₃ | N | 1 |
| CH₂cyPr | CF₂CF₃ | N | 2 |
| CH₂cyPr | OCF₃ | N | 0 |
| CH₂cyPr | OCF₃ | N | 1 |
| CH₂cyPr | OCF₃ | N | 2 |
| CH₂cyPr | SCF₃ | N | 0 |
| CH₂cyPr | SCF₃ | N | 1 |
| CH₂cyPr | SCF₃ | N | 2 |
| CH₂cyPr | S(O)CF₃ | N | 0 |
| CH₂cyPr | S(O)CF₃ | N | 1 |
| CH₂cyPr | S(O)CF₃ | N | 2 |
| CH₂cyPr | S(O)₂CF₃ | N | 0 |
| CH₂cyPr | S(O)₂CF₃ | N | 1 |
| CH₂cyPr | S(O)₂CF₃ | N | 2 |

TABLE 7

| R¹ | R³ | A¹ | n |
|---|---|---|---|
| CF₃ | H | N | 0 |
| CF₃ | H | N | 1 |
| CF₃ | H | N | 2 |
| CF₃ | F | N | 0 |
| CF₃ | F | N | 1 |
| CF₃ | F | N | 2 |
| CF₃ | Cl | N | 0 |
| CF₃ | Cl | N | 1 |
| CF₃ | Cl | N | 2 |
| CF₃ | Br | N | 0 |
| CF₃ | Br | N | 1 |

TABLE 7-continued

| R¹ | R³ | A¹ | n |
|---|---|---|---|
| CF₃ | Br | N | 2 |
| CF₃ | CF₃ | N | 0 |
| CF₃ | CF₃ | N | 1 |
| CF₃ | CF₃ | N | 2 |
| CF₃ | CF₂CF₃ | N | 0 |
| CF₃ | CF₂CF₃ | N | 1 |
| CF₃ | CF₂CF₃ | N | 2 |
| CF₃ | OCF₃ | N | 0 |
| CF₃ | OCF₃ | N | 1 |
| CF₃ | OCF₃ | N | 2 |
| CF₃ | SCF₃ | N | 0 |
| CF₃ | SCF₃ | N | 1 |
| CF₃ | SCF₃ | N | 2 |
| CF₃ | S(O)CF₃ | N | 0 |
| CF₃ | S(O)CF₃ | N | 1 |
| CF₃ | S(O)CF₃ | N | 2 |
| CF₃ | S(O)₂CF₃ | N | 0 |
| CF₃ | S(O)₂CF₃ | N | 1 |
| CF₃ | S(O)₂CF₃ | N | 2 |

TABLE 8

| R¹ | R³ | A¹ | n |
|---|---|---|---|
| CH₂CF₃ | H | N | 0 |
| CH₂CF₃ | H | N | 1 |
| CH₂CF₃ | H | N | 2 |
| CH₂CF₃ | F | N | 0 |
| CH₂CF₃ | F | N | 1 |
| CH₂CF₃ | F | N | 2 |
| CH₂CF₃ | Cl | N | 0 |
| CH₂CF₃ | Cl | N | 1 |
| CH₂CF₃ | Cl | N | 2 |
| CH₂CF₃ | Br | N | 0 |
| CH₂CF₃ | Br | N | 1 |
| CH₂CF₃ | Br | N | 2 |
| CH₂CF₃ | CF₃ | N | 0 |
| CH₂CF₃ | CF₃ | N | 1 |
| CH₂CF₃ | CF₃ | N | 2 |
| CH₂CF₃ | CF₂CF₃ | N | 0 |
| CH₂CF₃ | CF₂CF₃ | N | 1 |
| CH₂CF₃ | CF₂CF₃ | N | 2 |
| CH₂CF₃ | OCF₃ | N | 0 |
| CH₂CF₃ | OCF₃ | N | 1 |
| CH₂CF₃ | OCF₃ | N | 2 |
| CH₂CF₃ | SCF₃ | N | 0 |
| CH₂CF₃ | SCF₃ | N | 1 |
| CH₂CF₃ | SCF₃ | N | 2 |
| CH₂CF₃ | S(O)CF₃ | N | 0 |
| CH₂CF₃ | S(O)CF₃ | N | 1 |
| CH₂CF₃ | S(O)CF₃ | N | 2 |
| CH₂CF₃ | S(O)₂CF₃ | N | 0 |
| CH₂CF₃ | S(O)₂CF₃ | N | 1 |
| CH₂CF₃ | S(O)₂CF₃ | N | 2 |

TABLE 9

| R¹ | R³ | A¹ | n |
|---|---|---|---|
| Me | H | CH | 0 |
| Me | H | CH | 1 |
| Me | H | CH | 2 |
| Me | F | CH | 0 |
| Me | F | CH | 1 |
| Me | F | CH | 2 |
| Me | Cl | CH | 0 |
| Me | Cl | CH | 1 |
| Me | Cl | CH | 2 |
| Me | Br | CH | 0 |
| Me | Br | CH | 1 |
| Me | Br | CH | 2 |
| Me | CF₃ | CH | 0 |
| Me | CF₃ | CH | 1 |

TABLE 9-continued

| R¹ | R³ | A¹ | n |
|---|---|---|---|
| Me | CF₃ | CH | 2 |
| Me | CF₂CF₃ | CH | 0 |
| Me | CF₂CF₃ | CH | 1 |
| Me | CF₂CF₃ | CH | 2 |
| Me | OCF₃ | CH | 0 |
| Me | OCF₃ | CH | 1 |
| Me | OCF3 | CH | 2 |
| Me | SCF₃ | CH | 0 |
| Me | SCF₃ | CH | 1 |
| Me | SCF₃ | CH | 2 |
| Me | S(O)CF₃ | CH | 0 |
| Me | S(O)CF₃ | CH | 1 |
| Me | S(O)CF₃ | CH | 2 |
| Me | S(O)₂CF₃ | CH | 0 |
| Me | S(O)₂CF₃ | CH | 1 |
| Me | S(O)₂CF₃ | CH | 2 |

TABLE 10

| R¹ | R³ | A¹ | n |
|---|---|---|---|
| Et | H | CH | 0 |
| Et | H | CH | 1 |
| Et | H | CH | 2 |
| Et | F | CH | 0 |
| Et | F | CH | 1 |
| Et | F | CH | 2 |
| Et | Cl | CH | 0 |
| Et | Cl | CH | 1 |
| Et | Cl | CH | 2 |
| Et | Br | CH | 0 |
| Et | Br | CH | 1 |
| Et | Br | CH | 2 |
| Et | CF₃ | CH | 0 |
| Et | CF₃ | CH | 1 |
| Et | CF₃ | CH | 2 |
| Et | CF₂CF₃ | CH | 0 |
| Et | CF₂CF₃ | CH | 1 |
| Et | CF₂CF₃ | CH | 2 |
| Et | OCF₃ | CH | 0 |
| Et | OCF₃ | CH | 1 |
| Et | OCF₃ | CH | 2 |
| Et | SCF₃ | CH | 0 |
| Et | SCF₃ | CH | 1 |
| Et | SCF₃ | CH | 2 |
| Et | S(O)CF₃ | CH | 0 |
| Et | S(O)CF₃ | CH | 1 |
| Et | S(O)CF₃ | CH | 2 |
| Et | S(O)₂CF₃ | CH | 0 |
| Et | S(O)₂CF₃ | CH | 1 |
| Et | S(O)₂CF₃ | CH | 2 |

TABLE 11

| R¹ | R³ | A¹ | n |
|---|---|---|---|
| Pr | H | CH | 0 |
| Pr | H | CH | 1 |
| Pr | H | CH | 2 |
| Pr | F | CH | 0 |
| Pr | F | CH | 1 |
| Pr | F | CH | 2 |
| Pr | Cl | CH | 0 |
| Pr | Cl | CH | 1 |
| Pr | Cl | CH | 2 |
| Pr | Br | CH | 0 |
| Pr | Br | CH | 1 |
| Pr | Br | CH | 2 |
| Pr | CF₃ | CH | 0 |
| Pr | CF₃ | CH | 1 |
| Pr | CF₃ | CH | 2 |
| Pr | CF₂CF₃ | CH | 0 |
| Pr | CF₂CF₃ | CH | 1 |

TABLE 11-continued

| R¹ | R³ | A¹ | n |
|---|---|---|---|
| Pr | CF₂CF₃ | CH | 2 |
| Pr | OCF₃ | CH | 0 |
| Pr | OCF₃ | CH | 1 |
| Pr | OCF₃ | CH | 2 |
| Pr | SCF₃ | CH | 0 |
| Pr | SCF₃ | CH | 1 |
| Pr | SCF₃ | CH | 2 |
| Pr | S(O)CF₃ | CH | 0 |
| Pr | S(O)CF₃ | CH | 1 |
| Pr | S(O)CF₃ | CH | 2 |
| Pr | S(O)₂CF₃ | CH | 0 |
| Pr | S(O)₂CF₃ | CH | 1 |
| Pr | S(O)₂CF₃ | CH | 2 |

TABLE 12

| R¹ | R³ | A¹ | n |
|---|---|---|---|
| iPr | H | CH | 0 |
| iPr | H | CH | 1 |
| iPr | H | CH | 2 |
| iPr | F | CH | 0 |
| iPr | F | CH | 1 |
| iPr | F | CH | 2 |
| iPr | Cl | CH | 0 |
| iPr | Cl | CH | 1 |
| iPr | Cl | CH | 2 |
| iPr | Br | CH | 0 |
| iPr | Br | CH | 1 |
| iPr | Br | CH | 2 |
| iPr | CF₃ | CH | 0 |
| iPr | CF₃ | CH | 1 |
| iPr | CF₃ | CH | 2 |
| iPr | CF₂CF₃ | CH | 0 |
| iPr | CF₂CF₃ | CH | 1 |
| iPr | CF₂CF₃ | CH | 2 |
| iPr | OCF₃ | CH | 0 |
| iPr | OCF₃ | CH | 1 |
| iPr | OCF₃ | CH | 2 |
| iPr | SCF₃ | CH | 0 |
| iPr | SCF₃ | CH | 1 |
| iPr | SCF₃ | CH | 2 |
| iPr | S(O)CF₃ | CH | 0 |
| iPr | S(O)CF₃ | CH | 1 |
| iPr | S(O)CF₃ | CH | 2 |
| iPr | S(O)₂CF₃ | CH | 0 |
| iPr | S(O)₂CF₃ | CH | 1 |
| iPr | S(O)₂CF₃ | CH | 2 |

TABLE 13

| R¹ | R³ | A¹ | n |
|---|---|---|---|
| cyPr | H | CH | 0 |
| cyPr | H | CH | 1 |
| cyPr | H | CH | 2 |
| cyPr | F | CH | 0 |
| cyPr | F | CH | 1 |
| cyPr | F | CH | 2 |
| cyPr | Cl | CH | 0 |
| cyPr | Cl | CH | 1 |
| cyPr | Cl | CH | 2 |
| cyPr | Br | CH | 0 |
| cyPr | Br | CH | 1 |
| cyPr | Br | CH | 2 |
| cyPr | CF₃ | CH | 0 |
| cyPr | CF₃ | CH | 1 |
| cyPr | CF₃ | CH | 2 |
| cyPr | CF₂CF₃ | CH | 0 |
| cyPr | CF₂CF₃ | CH | 1 |
| cyPr | CF₂CF₃ | CH | 2 |
| cyPr | OCF₃ | CH | 0 |
| cyPr | OCF₃ | CH | 1 |

TABLE 13-continued

| R¹ | R³ | A¹ | n |
|---|---|---|---|
| cyPr | OCF₃ | CH | 2 |
| cyPr | SCF₃ | CH | 0 |
| cyPr | SCF₃ | CH | 1 |
| cyPr | SCF₃ | CH | 2 |
| cyPr | S(O)CF₃ | CH | 0 |
| cyPr | S(O)CF₃ | CH | 1 |
| cyPr | S(O)CF₃ | CH | 2 |
| cyPr | S(O)₂CF₃ | CH | 0 |
| cyPr | S(O)₂CF₃ | CH | 1 |
| cyPr | S(O)₂CF₃ | CH | 2 |

TABLE 14

| R¹ | R³ | A¹ | n |
|---|---|---|---|
| CH₂cyPr | H | CH | 0 |
| CH₂cyPr | H | CH | 1 |
| CH₂cyPr | H | CH | 2 |
| CH₂cyPr | F | CH | 0 |
| CH₂cyPr | F | CH | 1 |
| CH₂cyPr | F | CH | 2 |
| CH₂cyPr | Cl | CH | 0 |
| CH₂cyPr | Cl | CH | 1 |
| CH₂cyPr | Cl | CH | 2 |
| CH₂cyPr | Br | CH | 0 |
| CH₂cyPr | Br | CH | 1 |
| CH₂cyPr | Br | CH | 2 |
| CH₂cyPr | CF₃ | CH | 0 |
| CH₂cyPr | CF₃ | CH | 1 |
| CH₂cyPr | CF₃ | CH | 2 |
| CH₂cyPr | CF₂CF₃ | CH | 0 |
| CH₂cyPr | CF₂CF₃ | CH | 1 |
| CH₂cyPr | CF₂CF₃ | CH | 2 |
| CH₂cyPr | OCF₃ | CH | 0 |
| CH₂cyPr | OCF₃ | CH | 1 |
| CH₂cyPr | OCF₃ | CH | 2 |
| CH₂cyPr | SCF₃ | CH | 0 |
| CH₂cyPr | SCF₃ | CH | 1 |
| CH₂cyPr | SCF₃ | CH | 2 |
| CH₂cyPr | S(O)CF₃ | CH | 0 |
| CH₂cyPr | S(O)CF₃ | CH | 1 |
| CH₂cyPr | S(O)CF₃ | CH | 2 |
| CH₂cyPr | S(O)₂CF₃ | CH | 0 |
| CH₂cyPr | S(O)₂CF₃ | CH | 1 |
| CH₂cyPr | S(O)₂CF₃ | CH | 2 |

TABLE 15

| R¹ | R³ | A¹ | n |
|---|---|---|---|
| CF₃ | H | CH | 0 |
| CF₃ | H | CH | 1 |
| CF₃ | H | CH | 2 |
| CF₃ | F | CH | 0 |
| CF₃ | F | CH | 1 |
| CF₃ | F | CH | 2 |
| CF₃ | Cl | CH | 0 |
| CF₃ | Cl | CH | 1 |
| CF₃ | Cl | CH | 2 |
| CF₃ | Br | CH | 0 |
| CF₃ | Br | CH | 1 |
| CF₃ | Br | CH | 2 |
| CF₃ | CF₃ | CH | 0 |
| CF₃ | CF₃ | CH | 1 |
| CF₃ | CF₃ | CH | 2 |
| CF₃ | CF₂CF₃ | CH | 0 |
| CF₃ | CF₂CF₃ | CH | 1 |
| CF₃ | CF₂CF₃ | CH | 2 |
| CF₃ | OCF₃ | CH | 0 |
| CF₃ | OCF₃ | CH | 1 |
| CF₃ | OCF₃ | CH | 2 |
| CF₃ | SCF₃ | CH | 0 |
| CF₃ | SCF₃ | CH | 1 |

TABLE 15-continued

| R¹ | R³ | A¹ | n |
|---|---|---|---|
| CF₃ | SCF₃ | CH | 2 |
| CF₃ | S(O)CF₃ | CH | 0 |
| CF₃ | S(O)CF₃ | CH | 1 |
| CF₃ | S(O)CF₃ | CH | 2 |
| CF₃ | S(O)₂CF₃ | CH | 0 |
| CF₃ | S(O)₂CF₃ | CH | 1 |
| CF₃ | S(O)₂CF₃ | CH | 2 |

TABLE 16

| R¹ | R³ | A¹ | n |
|---|---|---|---|
| CH₂CF₃ | H | CH | 0 |
| CH₂CF₃ | H | CH | 1 |
| CH₂CF₃ | H | CH | 2 |
| CH₂CF₃ | F | CH | 0 |
| CH₂CF₃ | F | CH | 1 |
| CH₂CF₃ | F | CH | 2 |
| CH₂CF₃ | Cl | CH | 0 |
| CH₂CF₃ | Cl | CH | 1 |
| CH₂CF₃ | Cl | CH | 2 |
| CH₂CF₃ | Br | CH | 0 |
| CH₂CF₃ | Br | CH | 1 |
| CH₂CF₃ | Br | CH | 2 |
| CH₂CF₃ | CF₃ | CH | 0 |
| CH₂CF₃ | CF₃ | CH | 1 |
| CH₂CF₃ | CF₃ | CH | 2 |
| CH₂CF₃ | CF₂CF₃ | CH | 0 |
| CH₂CF₃ | CF₂CF₃ | CH | 1 |
| CH₂CF₃ | CF₂CF₃ | CH | 2 |
| CH₂CF₃ | OCF₃ | CH | 0 |
| CH₂CF₃ | OCF₃ | CH | 1 |
| CH₂CF₃ | OCF₃ | CH | 2 |
| CH₂CF₃ | SCF₃ | CH | 0 |
| CH₂CF₃ | SCF₃ | CH | 1 |
| CH₂CF₃ | SCF₃ | CH | 2 |
| CH₂CF₃ | S(O)CF₃ | CH | 0 |
| CH₂CF₃ | S(O)CF₃ | CH | 1 |
| CH₂CF₃ | S(O)CF₃ | CH | 2 |
| CH₂CF₃ | S(O)₂CF₃ | CH | 0 |
| CH₂CF₃ | S(O)₂CF₃ | CH | 1 |
| CH₂CF₃ | S(O)₂CF₃ | CH | 2 |

(In [Table 1] to [Table 16] above, Me represents a methyl group, Et represents an ethyl group, Pr represents a n-propyl group, iPr represents an isopropyl group, and cyPr represents a cyclopropyl group)

In the formula (A), compounds wherein $R^6$ is a pentafluoroethyl group, $R^9$ is a hydrogen atom, and $R^1$, $R^3$, $A^1$ and n are the combinations shown in [Table 1] to [Table 16].

In the formula (A), compounds wherein $R^6$ is a heptafluoroisopropyl group, $R^9$ is a hydrogen atom, and $R^1$, $R^3$, $A^1$ and n are the combinations shown in [Table 1] to [Table 16]

In the formula (A), compounds wherein $R^6$ is a trifluoromethoxy group, $R^9$ is a hydrogen atom, and $R^1$, $R^3$, $A^1$ and n are the combinations shown in [Table 1] to [Table 16].

In the formula (A), compounds wherein $R^6$ is a trifluoromethylsulfanyl group, $R^9$ is a hydrogen atom, and $R^1$, $R^3$, $A^1$ and n are the combinations shown in [Table 1] to [Table 16].

In the formula (A), compounds wherein $R^6$ is a trifluoromethylsulfinyl group, $R^9$ is a hydrogen atom, and $R^1$, $R^3$, $A^1$ and n are the combinations shown in [Table 1] to [Table 16].

In the formula (A), compounds wherein $R^6$ is a trifluoromethylsulfonyl group, $R^9$ is a hydrogen atom, and $R^1$, $R^3$, $A^1$ and n are the combinations shown in [Table 1] to [Table 16].

In the formula (A), compounds wherein $R^6$ is a trifluoromethyl group, $R^9$ is a methyl group, and $R^1$, $R^3$, $A^1$ and n are the combinations shown in [Table 1] to [Table 16].

In the formula (A), compounds wherein $R^6$ is a pentafluoroethyl group, $R^9$ is a methyl group, and $R^1$, $R^3$, $A^1$ and n are the combinations shown in [Table 1] to [Table 16].

In the formula (A), compounds wherein $R^6$ is a heptafluoroisopropyl group, $R^9$ is a methyl group, and $R^1$, $R^3$, $A^1$ and n are the combinations shown in [Table 1] to [Table 16]

In the formula (A), compounds wherein $R^6$ is a trifluoromethoxy group, $R^9$ is a methyl group, and $R^1$, $R^3$, $A^1$ and n are the combinations shown in [Table 1] to [Table 16].

In the formula (A), compounds wherein $R^6$ is a trifluoromethylsulfanyl group, $R^9$ is a methyl group, and $R^1$, $R^3$, $A^1$ and n are the combinations shown in [Table 1] to [Table 16].

In the formula (A), compounds wherein $R^6$ is a trifluoromethylsulfinyl group, $R^9$ is a methyl group, and $R^1$, $R^3$, $A^1$ and n are the combinations shown in [Table 1] to [Table 16].

In the formula (A), compounds wherein $R^6$ is a trifluoromethylsulfonyl group, $R^9$ is a methyl group, and $R^1$, $R^3$, $A^1$ and n are the combinations shown in [Table 1] to [Table 16].

In formula (B-1):

(B-1)

wherein symbols represent the same meaning as in the formula (1), compounds wherein $R^5$ is a trifluoromethyl group, $R^{10}$ is a hydrogen atom, and $R^1$, $R^3$, $A^1$ and n are the combinations shown in [Table 1] to [Table 16].

In the formula (B-1), compounds wherein $R^5$ is a pentafluoroethyl group, $R^{10}$ is a hydrogen atom, and $R^1$, $R^3$, $A^1$ and n are the combinations shown in [Table 1] to [Table 16].

In the formula (B-1), compounds wherein $R^5$ is a heptafluoroisopropyl group, $R^{10}$ is a hydrogen atom, and $R^1$, $R^3$, $A^1$ and n are the combinations shown in [Table 1] to [Table 16].

In the formula (B-1), compounds wherein $R^5$ is a trifluoromethoxy group, $R^{10}$ is a hydrogen atom, and $R^1$, $R^3$, $A^1$ and n are the combinations shown in [Table 1] to [Table 16].

In the formula (B-1), compounds wherein $R^5$ is a trifluoromethylsulfanyl group, $R^{10}$ is a hydrogen atom, and $R^1$, $R^3$, $A^1$ and n are the combinations shown in [Table 1] to [Table 16].

In the formula (B-1), compounds wherein $R^5$ is a trifluoromethylsulfinyl group, $R^{10}$ is a hydrogen atom, and $R^1$, $R^3$, $A^1$ and n are the combinations shown in [Table 1] to [Table 16].

In the formula (B-1), compounds wherein $R^5$ is a trifluoromethylsulfonyl group, $R^{10}$ is a hydrogen atom, and $R^1$, $R^3$, $A^1$ and n are the combinations shown in [Table 1] to [Table 16].

In the formula (B-1), compounds wherein $R^5$ is a trifluoromethyl group, $R^{10}$ is a chlorine atom, and $R^1$, $R^3$, $A^1$ and n are the combinations shown in [Table 1] to [Table 16].

In the formula (B-1), compounds wherein $R^5$ is a pentafluoroethyl group, $R^{10}$ is a chlorine atom, and $R^1$, $R^3$, $A^1$ and n are the combinations shown in [Table 1] to [Table 16].

In the formula (B-1), compounds wherein $R^5$ is a heptafluoroisopropyl group, $R^{10}$ is a chlorine atom, and $R^1$, $R^3$, $A^1$ and n are the combinations shown in [Table 1] to [Table 16]

In the formula (B-1), compounds wherein $R^5$ is a trifluoromethoxy group, $R^{10}$ is a chlorine atom, and $R^1$, $R^3$, $A^1$ and n are the combinations shown in [Table 1] to [Table 16].

In the formula (B-1), compounds wherein $R^5$ is a trifluoromethylsulfanyl group, $R^{10}$ is a chlorine atom, and $R^1$, $R^3$, $A^1$ and n are the combinations shown in [Table 1] to [Table 16].

In the formula (B-1), compounds wherein $R^5$ is a trifluoromethylsulfinyl group, $R^{10}$ is a chlorine atom, and $R^1$, $R^3$, $A^1$ and n are the combinations shown in [Table 1] to [Table 16].

In the formula (B-1), compounds wherein $R^5$ is a trifluoromethylsulfonyl group, $R^{10}$ is a chlorine atom, and $R^1$, $R^3$, $A^1$ and n are the combinations shown in [Table 1] to [Table 16].

In the formula (B-1), compounds wherein $R^5$ is a trifluoromethyl group, $R^{10}$ is a bromine atom, and $R^1$, $R^3$, $A^1$ and n are the combinations shown in [Table 1] to [Table 16].

In the formula (B-1), compounds wherein $R^5$ is a pentafluoroethyl group, $R^{10}$ is a bromine atom, and $R^1$, $R^3$, $A^1$ and n are the combinations shown in [Table 1] to [Table 16].

In the formula (B-1), compounds wherein $R^5$ is a heptafluoroisopropyl group, $R^{10}$ is a bromine atom, and $R^1$, $R^3$, $A^1$ and n are the combinations shown in [Table 1] to [Table 16].

In the formula (B-1), compounds wherein $R^5$ is a trifluoromethoxy group, $R^{10}$ is a bromine atom, and $R^1$, $R^3$, $A^1$ and n are the combinations shown in [Table 1] to [Table 16].

In the formula (B-1), compounds wherein $R^5$ is a trifluoromethylsulfanyl group, $R^{10}$ is a bromine atom, and $R^1$, $R^3$, $A^1$ and n are the combinations shown in [Table 1] to [Table 16].

In the formula (B-1), compounds wherein $R^5$ is a trifluoromethylsulfinyl group, $R^{10}$ is a bromine atom, and $R^1$, $R^3$, $A^1$ and n are the combinations shown in [Table 1] to [Table 16].

In the formula (B-1), compounds wherein $R^5$ is a trifluoromethylsulfonyl group, $R^{10}$ is a bromine atom, and $R^1$, $R^3$, $A^1$ and n are the combinations shown in [Table 1] to [Table 16].

In the formula (B-1), compounds wherein $R^5$ is a trifluoromethyl group, $R^{10}$ is a methyl group, and $R^1$, $R^3$, $A^1$ and n are the combinations shown in [Table 1] to [Table 16].

In the formula (B-1), compounds wherein $R^5$ is a pentafluoroethyl group, $R^{10}$ is a methyl group, and $R^1$, $R^3$, $A^1$ and n are the combinations shown in [Table 1] to [Table 16].

In the formula (B-1), compounds wherein $R^5$ is a heptafluoroisopropyl group, $R^{10}$ is a methyl group, and $R^1$, $R^3$, $A^1$ and n are the combinations shown in [Table 1] to [Table 16].

In the formula (B-1), compounds wherein $R^5$ is a trifluoromethoxy group, $R^{10}$ is a methyl group, and $R^1$, $R^3$, $A^1$ and n are the combinations shown in [Table 1] to [Table 16].

In the formula (B-1), compounds wherein $R^5$ is a trifluoromethylsulfanyl group, $R^{10}$ is a methyl group, and $R^1$, $R^3$, $A^1$ and n are the combinations shown in [Table 1] to [Table 16].

In the formula (B-1), compounds wherein $R^5$ is a trifluoromethylsulfinyl group, $R^{10}$ is a methyl group, and $R^1$, $R^3$, $A^1$ and n are the combinations shown in [Table 1] to [Table 16].

In the formula (B-1), compounds wherein $R^5$ is a trifluoromethylsulfonyl group, $R^{10}$ is a methyl group, and $R^1$, $R^3$, $A^1$ and n are the combinations shown in [Table 1] to [Table 16].

In formula (B-2):

(B-2)

wherein symbols represent the same meaning as in the formula (1), compounds wherein $R^5$ is a trifluoromethyl group, $R^{10}$ is a hydrogen atom, and $R^1$, $R^3$, $A^1$ and n are the combinations shown in [Table 1] to [Table 16].

In the formula (B-2), compounds wherein $R^5$ is a pentafluoroethyl group, $R^{10}$ is a hydrogen atom, and $R^1$, $R^3$, $A^1$ and n are the combinations shown in [Table 1] to [Table 16].

In the formula (B-2), compounds wherein $R^5$ is a heptafluoroisopropyl group, $R^{10}$ is a hydrogen atom, and $R^1$, $R^3$, $A^1$ and n are the combinations shown in [Table 1] to [Table 16]

In the formula (B-2), compounds wherein $R^5$ is a trifluoromethoxy group, $R^{10}$ is a hydrogen atom, and $R^1$, $R^3$, $A^1$ and n are the combinations shown in [Table 1] to [Table 16].

In the formula (B-2), compounds wherein $R^5$ is a trifluoromethylsulfanyl group, $R^{10}$ is a hydrogen atom, and $R^1$, $R^3$, $A^1$ and n are the combinations shown in [Table 1] to [Table 16].

In the formula (B-2), compounds wherein $R^5$ is a trifluoromethylsulfinyl group, $R^{10}$ is a hydrogen atom, and $R^1$, $R^3$, $A^1$ and n are the combinations shown in [Table 1] to [Table 16].

In the formula (B-2), compounds wherein $R^5$ is a trifluoromethylsulfonyl group, $R^{10}$ is a hydrogen atom, and $R^1$, $R^3$, $A^1$ and n are the combinations shown in [Table 1] to [Table 16].

In the formula (B-2), compounds wherein $R^5$ is a trifluoromethyl group, $R^{10}$ is a chlorine atom, and $R^1$, $R^3$, $A^1$ and n are the combinations shown in [Table 1] to [Table 16].

In the formula (B-2), compounds wherein $R^5$ is a pentafluoroethyl group, $R^{10}$ is a chlorine atom, and $R^1$, $R^3$, $A^1$ and n are the combinations shown in [Table 1] to [Table 16].

In the formula (B-2), compounds wherein $R^5$ is a heptafluoroisopropyl group, $R^{10}$ is a chlorine atom, and $R^1$, $R^3$, $A^1$ and n are the combinations shown in [Table 1] to [Table 16]

In the formula (B-2), compounds wherein $R^5$ is a trifluoromethoxy group, $R^{10}$ is a chlorine atom, and $R^1$, $R^3$, $A^1$ and n are the combinations shown in [Table 1] to [Table 16].

In the formula (B-2), compounds wherein $R^5$ is a trifluoromethylsulfanyl group, $R^{10}$ is a chlorine atom, and $R^1$, $R^3$, $A^1$ and n are the combinations shown in [Table 1] to [Table 16].

In the formula (B-2), compounds wherein $R^5$ is a trifluoromethylsulfinyl group, $R^{10}$ is a chlorine atom, and $R^1$, $R^3$, $A^1$ and n are the combinations shown in [Table 1] to [Table 16].

In the formula (B-2), compounds wherein $R^5$ is a trifluoromethylsulfonyl group, $R^{10}$ is a chlorine atom, and $R^1$, $R^3$, $A^1$ and n are the combinations shown in [Table 1] to [Table 16].

In the formula (B-2), compounds wherein $R^5$ is a trifluoromethyl group, $R^{10}$ is a bromine atom, and $R^1$, $R^3$, $A^1$ and n are the combinations shown in [Table 1] to [Table 16].

In the formula (B-2), compounds wherein $R^5$ is a pentafluoroethyl group, $R^{10}$ is a bromine atom, and $R^1$, $R^3$, $A^1$ and n are the combinations shown in [Table 1] to [Table 16].

In the formula (B-2), compounds wherein $R^5$ is a heptafluoroisopropyl group, $R^{10}$ is a bromine atom, and $R^1$, $R^3$, $A^1$ and n are the combinations shown in [Table 1] to [Table 16].

In the formula (B-2), compounds wherein $R^5$ is a trifluoromethoxy group, $R^{10}$ is a bromine atom, and $R^1$, $R^3$, $A^1$ and n are the combinations shown in [Table 1] to [Table 16].

In the formula (B-2), compounds wherein $R^5$ is a trifluoromethylsulfanyl group, $R^{10}$ is a bromine atom, and $R^1$, $R^3$, $A^1$ and n are the combinations shown in [Table 1] to [Table 16].

In the formula (B-2), compounds wherein $R^5$ is a trifluoromethylsulfinyl group, $R^{10}$ is a bromine atom, and $R^1$, $R^3$, $A^1$ and n are the combinations shown in [Table 1] to [Table 16].

In the formula (B-2), compounds wherein $R^5$ is a trifluoromethylsulfonyl group, $R^{10}$ is a bromine atom, and $R^1$, $R^3$, $A^1$ and n are the combinations shown in [Table 1] to [Table 16].

In the formula (B-2), compounds wherein $R^5$ is a trifluoromethyl group, $R^{10}$ is a methyl group, and $R^1$, $R^3$, $A^1$ and n are the combinations shown in [Table 1] to [Table 16].

In the formula (B-2), compounds wherein $R^5$ is a pentafluoroethyl group, $R^{10}$ is a methyl group, and $R^1$, $R^3$, $A^1$ and n are the combinations shown in [Table 1] to [Table 16].

In the formula (B-2), compounds wherein $R^5$ is a heptafluoroisopropyl group, $R^{10}$ is a methyl group, and $R^1$, $R^3$, $A^1$ and n are the combinations shown in [Table 1] to [Table 16].

In the formula (B-2), compounds wherein $R^5$ is a trifluoromethoxy group, $R^{10}$ is a methyl group, and $R^1$, $R^3$, $A^1$ and n are the combinations shown in [Table 1] to [Table 16].

In the formula (B-2), compounds wherein $R^5$ is a trifluoromethylsulfanyl group, $R^{10}$ is a methyl group, and $R^1$, $R^3$, $A^1$ and n are the combinations shown in [Table 1] to [Table 16].

In the formula (B-2), compounds wherein $R^5$ is a trifluoromethylsulfinyl group, $R^{10}$ is a methyl group, and $R^1$, $R^3$, $A^1$ and n are the combinations shown in [Table 1] to [Table 16].

In the formula (B-2), compounds wherein $R^5$ is a trifluoromethylsulfonyl group, $R^{10}$ is a methyl group, and $R^1$, $R^3$, $A^1$ and n are the combinations shown in [Table 1] to [Table 16].

In formula (C-1):

(C-1)

wherein symbols represent the same meaning as in the formula (1), compounds wherein $R^6$ is a trifluoromethyl group, $R^{10}$ is a hydrogen atom, and $R^1$, $R^3$, $A^1$ and n are the combinations shown in [Table 1] to [Table 16].

In the formula (C-1), compounds wherein $R^6$ is a pentafluoroethyl group, $R^{10}$ is a hydrogen atom, and $R^1$, $R^3$, $A^1$ and n are the combinations shown in [Table 1] to [Table 16].

In the formula (C-1), compounds wherein $R^6$ is a heptafluoroisopropyl group, $R^{10}$ is a hydrogen atom, and $R^1$, $R^3$, $A^1$ and n are the combinations shown in [Table 1] to [Table 16]

In the formula (C-1), compounds wherein $R^6$ is a trifluoromethoxy group, $R^{10}$ is a hydrogen atom, and $R^1$, $R^3$, $A^1$ and n are the combinations shown in [Table 1] to [Table 16].

In the formula (C-1), compounds wherein $R^6$ is a trifluoromethylsulfanyl group, $R^{10}$ is a hydrogen atom, and $R^1$, $R^3$, $A^1$ and n are the combinations shown in [Table 1] to [Table 16].

In the formula (C-1), compounds wherein $R^6$ is a trifluoromethylsulfinyl group, $R^{10}$ is a hydrogen atom, and $R^1$, $R^3$, $A^1$ and n are the combinations shown in [Table 1] to [Table 16].

In the formula (C-1), compounds wherein $R^6$ is a trifluoromethylsulfonyl group, $R^{10}$ is a hydrogen atom, and $R^1$, $R^3$, $A^1$ and n are the combinations shown in [Table 1] to [Table 16].

In the formula (C-1), compounds wherein $R^6$ is a trifluoromethyl group, $R^{10}$ is a chlorine atom, and $R^1$, $R^3$, $A^1$ and n are the combinations shown in [Table 1] to [Table 16].

In the formula (C-1), compounds wherein $R^6$ is a pentafluoroethyl group, $R^{10}$ is a chlorine atom, and $R^1$, $R^3$, $A^1$ and n are the combinations shown in [Table 1] to [Table 16].

In the formula (C-1), compounds wherein $R^6$ is a heptafluoroisopropyl group, $R^{10}$ is a chlorine atom, and $R^1$, $R^3$, $A^1$ and n are the combinations shown in [Table 1] to [Table 16]

In the formula (C-1), compounds wherein $R^6$ is a trifluoromethoxy group, $R^{10}$ is a chlorine atom, and $R^1$, $R^3$, $A^1$ and n are the combinations shown in [Table 1] to [Table 16].

In the formula (C-1), compounds wherein $R^6$ is a trifluoromethylsulfanyl group, $R^{10}$ is a chlorine atom, and $R^1$, $R^3$, $A^1$ and n are the combinations shown in [Table 1] to [Table 16].

In the formula (C-1), compounds wherein $R^6$ is a trifluoromethylsulfinyl group, $R^{10}$ is a chlorine atom, and $R^1$, $R^3$, $A^1$ and n are the combinations shown in [Table 1] to [Table 16].

In the formula (C-1), compounds wherein $R^6$ is a trifluoromethylsulfonyl group, $R^{10}$ is a chlorine atom, and $R^1$, $R^3$, $A^1$ and n are the combinations shown in [Table 1] to [Table 16].

In the formula (C-1), compounds wherein $R^6$ is a trifluoromethyl group, $R^{10}$ is a bromine atom, and $R^1$, $R^3$, $A^1$ and n are the combinations shown in [Table 1] to [Table 16].

In the formula (C-1), compounds wherein $R^6$ is a pentafluoroethyl group, $R^{10}$ is a bromine atom, and $R^1$, $R^3$, $A^1$ and n are the combinations shown in [Table 1] to [Table 16].

In the formula (C-1), compounds wherein $R^6$ is a heptafluoroisopropyl group, $R^{10}$ is a bromine atom, and $R^1$, $R^3$, $A^1$ and n are the combinations shown in [Table 1] to [Table 16]

In the formula (C-1), compounds wherein $R^6$ is a trifluoromethoxy group, $R^{10}$ is a bromine atom, and $R^1$, $R^3$, $A^1$ and n are the combinations shown in [Table 1] to [Table 16].

In the formula (C-1), compounds wherein $R^6$ is a trifluoromethylsulfanyl group, $R^{10}$ is a bromine atom, and $R^1$, $R^3$, $A^1$ and n are the combinations shown in [Table 1] to [Table 16].

In the formula (C-1), compounds wherein $R^6$ is a trifluoromethylsulfinyl group, $R^{10}$ is a bromine atom, and $R^1$, $R^3$, $A^1$ and n are the combinations shown in [Table 1] to [Table 16].

In the formula (C-1), compounds wherein $R^6$ is a trifluoromethylsulfonyl group, $R^{10}$ is a bromine atom, and $R^1$, $R^3$, $A^1$ and n are the combinations shown in [Table 1] to [Table 16].

In the formula (C-1), compounds wherein $R^6$ is a trifluoromethyl group, $R^{10}$ is a methyl group, and $R^1$, $R^3$, $A^1$ and n are the combinations shown in [Table 1] to [Table 16].

In the formula (C-1), compounds wherein $R^6$ is a pentafluoroethyl group, $R^{10}$ is a methyl group, and $R^1$, $R^3$, $A^1$ and n are the combinations shown in [Table 1] to [Table 16].

In the formula (C-1), compounds wherein $R^6$ is a heptafluoroisopropyl group, $R^{10}$ is a methyl group, and $R^1$, $R^3$, $A^1$ and n are the combinations shown in [Table 1] to [Table 16]

In the formula (C-1), compounds wherein $R^6$ is a trifluoromethoxy group, $R^{10}$ is a methyl group, and $R^1$, $R^3$, $A^1$ and n are the combinations shown in [Table 1] to [Table 16].

In the formula (C-1), compounds wherein $R^6$ is a trifluoromethylsulfanyl group, $R^{10}$ is a methyl group, and $R^1$, $R^3$, $A^1$ and n are the combinations shown in [Table 1] to [Table 16].

In the formula (C-1), compounds wherein $R^6$ is a trifluoromethylsulfinyl group, $R^{10}$ is a methyl group, and $R^1$, $R^3$, $A^1$ and n are the combinations shown in [Table 1] to [Table 16].

In the formula (C-1), compounds wherein $R^6$ is a trifluoromethylsulfonyl group, $R^{10}$ is a methyl group, and $R^1$, $R^3$, $A^1$ and n are the combinations shown in [Table 1] to [Table 16].

In formula (C-2):

(C-2)

wherein symbols represent the same meaning as in the formula (1), compounds wherein $R^5$ is a trifluoromethyl group, $R^{10}$ is a hydrogen atom, and $R^1$, $R^3$, $A^1$ and n are the combinations shown in [Table 1] to [Table 16].

In the formula (C-2), compounds wherein $R^6$ is a pentafluoroethyl group, $R^{10}$ is a hydrogen atom, and $R^1$, $R^3$, $A^1$ and n are the combinations shown in [Table 1] to [Table 16].

In the formula (C-2), compounds wherein $R^6$ is a heptafluoroisopropyl group, $R^{10}$ is a hydrogen atom, and $R^1$, $R^3$, $A^1$ and n are the combinations shown in [Table 1] to [Table 16]

In the formula (C-2), compounds wherein $R^6$ is a trifluoromethoxy group, $R^{10}$ is a hydrogen atom, and $R^1$, $R^3$, $A^1$ and n are the combinations shown in [Table 1] to [Table 16].

In the formula (C-2), compounds wherein $R^6$ is a trifluoromethylsulfanyl group, $R^{10}$ is a hydrogen atom, and $R^1$, $R^3$, $A^1$ and n are the combinations shown in [Table 1] to [Table 16].

In the formula (C-2), compounds wherein $R^6$ is a trifluoromethylsulfinyl group, $R^{10}$ is a hydrogen atom, and $R^1$, $R^3$, $A^1$ and n are the combinations shown in [Table 1] to [Table 16].

In the formula (C-2), compounds wherein $R^6$ is a trifluoromethylsulfonyl group, $R^{10}$ is a hydrogen atom, and $R^1$, $R^3$, $A^1$ and n are the combinations shown in [Table 1] to [Table 16].

In the formula (C-2), compounds wherein $R^6$ is a trifluoromethyl group, $R^{10}$ is a chlorine atom, and $R^1$, $R^3$, $A^1$ and n are the combinations shown in [Table 1] to [Table 16].

In the formula (C-2), compounds wherein $R^6$ is a pentafluoroethyl group, $R^{10}$ is a chlorine atom, and $R^1$, $R^3$, $A^1$ and n are the combinations shown in [Table 1] to [Table 16].

In the formula (C-2), compounds wherein $R^6$ is a heptafluoroisopropyl group, $R^{10}$ is a chlorine atom, and $R^1$, $R^3$, $A^1$ and n are the combinations shown in [Table 1] to [Table 16]

In the formula (C-2), compounds wherein $R^6$ is a trifluoromethoxy group, $R^{10}$ is a chlorine atom, and $R^1$, $R^3$, $A^1$ and n are the combinations shown in [Table 1] to [Table 16].

In the formula (C-2), compounds wherein $R^6$ is a trifluoromethylsulfanyl group, $R^{10}$ is a chlorine atom, and $R^1$, $R^3$, $A^1$ and n are the combinations shown in [Table 1] to [Table 16].

In the formula (C-2), compounds wherein $R^6$ is a trifluoromethylsulfinyl group, $R^{10}$ is a chlorine atom, and $R^1$, $R^3$, $A^1$ and n are the combinations shown in [Table 1] to [Table 16].

In the formula (C-2), compounds wherein $R^6$ is a trifluoromethylsulfonyl group, $R^{10}$ is a chlorine atom, and $R^1$, $R^3$, $A^1$ and n are the combinations shown in [Table 1] to [Table 16].

In the formula (C-2), compounds wherein $R^6$ is a trifluoromethyl group, $R^{10}$ is a bromine atom, and $R^1$, $R^3$, $A^1$ and n are the combinations shown in [Table 1] to [Table 16].

In the formula (C-2), compounds wherein $R^6$ is a pentafluoroethyl group, $R^{10}$ is a bromine atom, and $R^1$, $R^3$, $A^1$ and n are the combinations shown in [Table 1] to [Table 16].

In the formula (C-2), compounds wherein $R^6$ is a heptafluoroisopropyl group, $R^{10}$ is a bromine atom, and $R^1$, $R^3$, $A^1$ and n are the combinations shown in [Table 1] to [Table 16]

In the formula (C-2), compounds wherein $R^6$ is a trifluoromethoxy group, $R^{10}$ is a bromine atom, and $R^1$, $R^3$, $A^1$ and n are the combinations shown in [Table 1] to [Table 16].

In the formula (C-2), compounds wherein $R^6$ is a trifluoromethylsulfanyl group, $R^{10}$ is a bromine atom, and $R^1$, $R^3$, $A^1$ and n are the combinations shown in [Table 1] to [Table 16].

In the formula (C-2), compounds wherein $R^6$ is a trifluoromethylsulfinyl group, $R^{10}$ is a bromine atom, and $R^1$, $R^3$, $A^1$ and n are the combinations shown in [Table 1] to [Table 16].

In the formula (C-2), compounds wherein $R^6$ is a trifluoromethylsulfonyl group, $R^{10}$ is a bromine atom, and $R^1$, $R^3$, $A^1$ and n are the combinations shown in [Table 1] to [Table 16].

In the formula (C-2), compounds wherein $R^6$ is a trifluoromethyl group, $R^{10}$ is a methyl group, and $R^1$, $R^3$, $A^1$ and n are the combinations shown in [Table 1] to [Table 16].

In the formula (C-2), compounds wherein $R^6$ is a pentafluoroethyl group, $R^{10}$ is a methyl group, and $R^1$, $R^3$, $A^1$ and n are the combinations shown in [Table 1] to [Table 16].

In the formula (C-2), compounds wherein $R^6$ is a heptafluoroisopropyl group, $R^{10}$ is a methyl group, and $R^1$, $R^3$, $A^1$ and n are the combinations shown in [Table 1] to [Table 16]

In the formula (C-2), compounds wherein $R^6$ is a trifluoromethoxy group, $R^{10}$ is a methyl group, and $R^1$, $R^3$, $A^1$ and n are the combinations shown in [Table 1] to [Table 16].

In the formula (C-2), compounds wherein $R^6$ is a trifluoromethylsulfanyl group, $R^{10}$ is a methyl group, and $R^1$, $R^3$, $A^1$ and n are the combinations shown in [Table 1] to [Table 16].

In the formula (C-2), compounds wherein $R^6$ is a trifluoromethylsulfinyl group, $R^{10}$ is a methyl group, and $R^1$, $R^3$, $A^1$ and n are the combinations shown in [Table 1] to [Table 16].

In the formula (C-2), compounds wherein $R^6$ is a trifluoromethylsulfonyl group, $R^{10}$ is a methyl group, and $R^1$, $R^3$, $A^1$ and n are the combinations shown in [Table 1] to [Table 16].

In formula (D):

(D)

wherein symbols represent the same meaning as in the formula (1), compounds wherein $R^5$ is a trifluoromethyl group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a pentafluoroethyl group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a heptafluoroisopropyl group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a trifluoromethoxy group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a trifluoromethylsulfanyl group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a trifluoromethylsulfinyl group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a trifluoromethylsulfonyl group, $R^9$ and $R^{10}$ are a hydrogen atom, and $R^1$, $R^3$, $A^1$ and n are the combinations shown in [Table 1] to [Table 16].

In the formula (D), compounds wherein $R^5$ is a trifluoromethyl group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a pentafluoroethyl group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a heptafluoroisopropyl group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a trifluoromethoxy group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a trifluoromethylsulfanyl group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a trifluoromethylsulfinyl group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a trifluoromethylsulfonyl group, $R^9$ is a methyl group, $R^{10}$ is a hydrogen atom, and $R^1$, $R^3$, $A^1$ and n are the combinations shown in [Table 1] to [Table 16].

In the formula (D), compounds wherein $R^5$ is a trifluoromethyl group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a pentafluoroethyl group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a heptafluoroisopropyl group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a trifluoromethoxy group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a trifluoromethylsulfanyl group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a trifluoromethylsulfinyl group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a trifluoromethylsulfonyl group, $R^9$ is a hydrogen atom, $R^{10}$ is a methyl group, and $R^1$, $R^3$, $A^1$ and n are the combinations shown in [Table 1] to [Table 16].

In the formula (D), compounds wherein $R^5$ is a trifluoromethyl group, $R^9$ and $R^{10}$ are a methyl group, and $R^1$, $R^3$, $A^1$ and n are the combinations shown in [Table 1] to [Table 16].

In the formula (D), compounds wherein $R^5$ is a pentafluoroethyl group, $R^9$ and $R^{10}$ are a methyl group, and $R^1$, $R^3$, $A^1$ and n are the combinations shown in [Table 1] to [Table 16].

In the formula (D), compounds wherein $R^5$ is a heptafluoroisopropyl group, $R^9$ and $R^{10}$ are a methyl group, and $R^1$, $R^3$, $A^1$ and n are the combinations shown in [Table 1] to [Table 16].

In the formula (D), compounds wherein $R^5$ is a trifluoromethoxy group, $R^9$ and $R^{10}$ are a methyl group, and $R^1$, $R^3$, $A^1$ and n are the combinations shown in [Table 1] to [Table 16].

In the formula (D), compounds wherein $R^5$ is a trifluoromethylsulfanyl group, $R^9$ and $R^{10}$ are a methyl group, and $R^1$, $R^3$, $A^1$ and n are the combinations shown in [Table 1] to [Table 16].

In the formula (D), compounds wherein $R^5$ is a trifluoromethylsulfinyl group, $R^9$ and $R^{10}$ are a methyl group, and $R^1$, $R^3$, $A^1$ and n are the combinations shown in [Table 1] to [Table 16].

In the formula (D), compounds wherein $R^5$ is a trifluoromethylsulfonyl group, $R^9$ and $R^{10}$ are a methyl group, and $R^1$, $R^3$, $A^1$ and n are the combinations shown in [Table 1] to [Table 16].

In formula (E):

$$(E)$$

wherein symbols represent the same meaning as in the formula (1), compounds wherein $R^6$ is a trifluoromethyl group, $R^9$ is a hydrogen atom, and $R^1$, $R^3$, $A^1$ and n are the combinations shown in [Table 1] to [Table 16].

In the formula (E), compounds wherein $R^6$ is a pentafluoroethyl group, $R^9$ is a hydrogen atom, and $R^1$, $R^3$, $A^1$ and n are the combinations shown in [Table 1] to [Table 16].

In the formula (E), compounds wherein $R^6$ is a heptafluoroisopropyl group, $R^9$ is a hydrogen atom, and $R^1$, $R^3$, $A^1$ and n are the combinations shown in [Table 1] to [Table 16].

In the formula (E), compounds wherein $R^6$ is a trifluoromethoxy group, $R^9$ is a hydrogen atom, and $R^1$, $R^3$, $A^1$ and n are the combinations shown in [Table 1] to [Table 16].

In the formula (E), compounds wherein $R^6$ is a trifluoromethylsulfanyl group, $R^9$ is a hydrogen atom, and $R^1$, $R^3$, $A^1$ and n are the combinations shown in [Table 1] to [Table 16].

In the formula (E), compounds wherein $R^6$ is a trifluoromethylsulfinyl group, $R^9$ is a hydrogen atom, and $R^1$, $R^3$, $A^1$ and n are the combinations shown in [Table 1] to [Table 16].

In the formula (E), compounds wherein $R^6$ is a trifluoromethylsulfonyl group, $R^9$ is a hydrogen atom, and $R^1$, $R^3$, $A^1$ and n are the combinations shown in [Table 1] to [Table 16].

In the formula (E), compounds wherein $R^6$ is a trifluoromethyl group, $R^9$ is a chlorine atom, and $R^1$, $R^3$, $A^1$ and n are the combinations shown in [Table 1] to [Table 16].

In the formula (E), compounds wherein $R^6$ is a pentafluoroethyl group, $R^9$ is a chlorine atom, and $R^1$, $R^3$, $A^1$ and n are the combinations shown in [Table 1] to [Table 16].

In the formula (E), compounds wherein $R^6$ is a heptafluoroisopropyl group, $R^9$ is a chlorine atom, and $R^1$, $R^3$, $A^1$ and n are the combinations shown in [Table 1] to [Table 16]

In the formula (E), compounds wherein $R^6$ is a trifluoromethoxy group, $R^9$ is a chlorine atom, and $R^1$, $R^3$, $A^1$ and n are the combinations shown in [Table 1] to [Table 16].

In the formula (E), compounds wherein $R^6$ is a trifluoromethylsulfanyl group, $R^9$ is a chlorine atom, and $R^1$, $R^3$, $A^1$ and n are the combinations shown in [Table 1] to [Table 16].

In the formula (E), compounds wherein $R^6$ is a trifluoromethylsulfinyl group, $R^9$ is a chlorine atom, and $R^1$, $R^3$, $A^1$ and n are the combinations shown in [Table 1] to [Table 16].

In the formula (E), compounds wherein $R^6$ is a trifluoromethylsulfonyl group, $R^9$ is a chlorine atom, and $R^1$, $R^3$, $A^1$ and n are the combinations shown in [Table 1] to [Table 16].

In the formula (E), compounds wherein $R^6$ is a trifluoromethyl group, $R^9$ is a bromine atom, and $R^1$, $R^3$, $A^1$ and n are the combinations shown in [Table 1] to [Table 16].

In the formula (E), compounds wherein $R^6$ is a pentafluoroethyl group, $R^9$ is a bromine atom, and $R^1$, $R^3$, $A^1$ and n are the combinations shown in [Table 1] to [Table 16].

In the formula (E), compounds wherein $R^6$ is a heptafluoroisopropyl group, $R^9$ is a bromine atom, and $R^1$, $R^3$, $A^1$ and n are the combinations shown in [Table 1] to [Table 16].

In the formula (E), compounds wherein $R^6$ is a trifluoromethoxy group, $R^9$ is a bromine atom, and $R^1$, $R^3$, $A^1$ and n are the combinations shown in [Table 1] to [Table 16].

In the formula (E), compounds wherein $R^6$ is a trifluoromethylsulfanyl group, $R^9$ is a bromine atom, and $R^1$, $R^3$, $A^1$ and n are the combinations shown in [Table 1] to [Table 16].

In the formula (E), compounds wherein $R^6$ is a trifluoromethylsulfinyl group, $R^9$ is a bromine atom, and $R^1$, $R^3$, $A^1$ and n are the combinations shown in [Table 1] to [Table 16].

In the formula (E), compounds wherein $R^6$ is a trifluoromethylsulfonyl group, $R^9$ is a bromine atom, and $R^1$, $R^3$, $A^1$ and n are the combinations shown in [Table 1] to [Table 16].

In the formula (E), compounds wherein $R^6$ is a trifluoromethyl group, $R^9$ is a methyl group, and $R^1$, $R^3$, $A^1$ and n are the combinations shown in [Table 1] to [Table 16].

In the formula (E), compounds wherein $R^6$ is a pentafluoroethyl group, $R^9$ is a methyl group, and $R^1$, $R^3$, $A^1$ and n are the combinations shown in [Table 1] to [Table 16].

In the formula (E), compounds wherein $R^6$ is a heptafluoroisopropyl group, $R^9$ is a methyl group, and $R^1$, $R^3$, $A^1$ and n are the combinations shown in [Table 1] to [Table 16]

In the formula (E), compounds wherein $R^6$ is a trifluoromethoxy group, $R^9$ is a methyl group, and $R^1$, $R^3$, $A^1$ and n are the combinations shown in [Table 1] to [Table 16].

In the formula (E), compounds wherein $R^6$ is a trifluoromethylsulfanyl group, $R^9$ is a methyl group, and $R^1$, $R^3$, $A^1$ and n are the combinations shown in [Table 1] to [Table 16].

In the formula (E), compounds wherein $R^6$ is a trifluoromethylsulfinyl group, $R^9$ is a methyl group, and $R^1$, $R^3$, $A^1$ and n are the combinations shown in [Table 1] to [Table 16].

In the formula (E), compounds wherein $R^6$ is a trifluoromethylsulfonyl group, $R^9$ is a methyl group, and $R^1$, $R^3$, $A^1$ and n are the combinations shown in [Table 1] to [Table 16].

In formula (F):

$$(F)$$

[Structure: imidazo[4,5-b]pyridine with N-CH3, R14 at 2-position, connected to pyridine bearing A1 ring with R3 and S(O)n-R1 group]

wherein symbols represent the same meaning as in the formula (1), compounds wherein $R^{14}$ is a trifluoromethyl group, and $R^1$, $R^3$, $A^1$ and n are the combinations shown in [Table 1] to [Table 16].

In the formula (F), compounds wherein $R^6$ is a pentafluoroethyl group, and $R^1$, $R^3$, $A^1$ and n are the combinations shown in [Table 1] to [Table 16].

In the formula (F), compounds wherein $R^6$ is a heptafluoroisopropyl group, and $R^1$, $R^3$, $A^1$ and n are the combinations shown in [Table 1] to [Table 16].

In the formula (F), compounds wherein $R^6$ is a trifluoromethoxy group, and $R^1$, $R^3$, $A^1$ and n are the combinations shown in [Table 1] to [Table 16].

In the formula (F), compounds wherein $R^6$ is a trifluoromethylsulfanyl group, and $R^1$, $R^3$, $A^1$ and n are the combinations shown in [Table 1] to [Table 16].

In the formula (F), compounds wherein $R^6$ is a trifluoromethylsulfinyl group, and $R^1$, $R^3$, $A^1$ and n are the combinations shown in [Table 1] to [Table 16].

In the formula (F), compounds wherein $R^6$ is a trifluoromethylsulfonyl group, and $R^1$, $R^3$, $A^1$ and n are the combinations shown in [Table 1] to [Table 16].

In formula (G):

$$(G)$$

wherein symbols represent the same meaning as in the formula (1), compounds wherein $R^{14}$ is a trifluoromethyl group, and $R^1$, $R^3$, $A^1$ and n are the combinations shown in [Table 1] to [Table 16].

In the formula (G), compounds wherein $R^6$ is a pentafluoroethyl group, and $R^1$, $R^3$, $A^1$ and n are the combinations shown in [Table 1] to [Table 16].

In the formula (G), compounds wherein $R^6$ is a heptafluoroisopropyl group, and $R^1$, $R^3$, $A^1$ and n are the combinations shown in [Table 1] to [Table 16].

In the formula (G), compounds wherein $R^6$ is a trifluoromethoxy group, and $R^1$, $R^3$, $A^1$ and n are the combinations shown in [Table 1] to [Table 16].

In the formula (G), compounds wherein $R^6$ is a trifluoromethylsulfanyl group, and $R^1$, $R^3$, $A^1$ and n are the combinations shown in [Table 1] to [Table 16].

In the formula (G), compounds wherein $R^6$ is a trifluoromethylsulfinyl group, and $R^1$, $R^3$, $A^1$ and n are the combinations shown in [Table 1] to [Table 16].

In the formula (G), compounds wherein $R^6$ is a trifluoromethylsulfonyl group, and $R^1$, $R^3$, $A^1$ and n are the combinations shown in [Table 1] to [Table 16].

In formula (H-1):

$$(H\text{-}1)$$

wherein symbols represent the same meaning as in the formula (1), compounds wherein $R^{17}$ is a trifluoromethyl group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a pentafluoroethyl group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a heptafluoroisopropyl group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethoxy group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethylsulfanyl group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethylsulfinyl group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethylsulfonyl group, $R^8$, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethyl group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a pentafluoroethyl group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a heptafluoroisopropyl group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethoxy group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethylsulfanyl group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethylsulfinyl group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethylsulfonyl group, $R^8$ is a methyl group, $R^9$ and $R^{10}$ are a hydrogen atom, and $R^1$, $R^3$, $A^1$ and n are the combinations shown in [Table 1] to [Table 16].

In the formula (H-1), compounds wherein $R^{17}$ is a trifluoromethyl group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a pentafluoroethyl group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a heptafluoroisopropyl group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a trifluoromethoxy group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a trifluoromethylsulfanyl group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a trifluoromethylsulfinyl group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a trifluoromethylsulfonyl group, $R^8$ and $R^{10}$ are a hydrogen atom, $R^9$ is a methyl group, and $R^1$, $R^3$, $A^1$ and n are the combinations shown in [Table 1] to [Table 16].

In the formula (H-1), compounds wherein $R^{17}$ is a trifluoromethyl group, $R^8$ and $R^9$ are a hydrogen atom, $R^{10}$ is a methyl group, and $R^1$, $R^3$, $A^1$ and n are the combinations shown in [Table 1] to [Table 16].

In the formula (H-1), compounds wherein $R^{17}$ is a pentafluoroethyl group, $R^8$ and $R^9$ are a hydrogen atom, $R^{10}$ is a methyl group, and $R^1$, $R^3$, $A^1$ and n are the combinations shown in [Table 1] to [Table 16].

In the formula (H-1), compounds wherein $R^{17}$ is a heptafluoroisopropyl group, $R^8$ and $R^9$ are a hydrogen atom, $R^{10}$ is a methyl group, and $R^1$, $R^3$, $A^1$ and n are the combinations shown in [Table 1] to [Table 16].

In the formula (H-1), compounds wherein $R^{17}$ is a trifluoromethoxy group, $R^8$ and $R^9$ are a hydrogen atom, $R^{10}$ is a methyl group, and $R^1$, $R^3$, $A^1$ and n are the combinations shown in [Table 1] to [Table 16].

In the formula (H-1), compounds wherein $R^{17}$ is a trifluoromethylsulfanyl group, $R^8$ and $R^9$ are a hydrogen atom, $R^{10}$ is a methyl group, and $R^1$, $R^3$, $A^1$ and n are the combinations shown in [Table 1] to [Table 16].

In the formula (H-1), compounds wherein $R^{17}$ is a trifluoromethylsulfinyl group, $R^8$ and $R^9$ are a hydrogen atom, $R^{10}$ is a methyl group, and $R^1$, $R^3$, $A^1$ and n are the combinations shown in [Table 1] to [Table 16].

In the formula (H-1), compounds wherein $R^{17}$ is a trifluoromethylsulfonyl group, $R^8$ and $R^9$ are a hydrogen atom, $R^{10}$ is a methyl group, and $R^1$, $R^3$, $A^1$ and n are the combinations shown in [Table 1] to [Table 16].

In formula (H-2):

(H-2)

wherein symbols represent the same meaning as in the formula (1), compounds wherein $R^{17}$ is a trifluoromethyl group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a pentafluoroethyl group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a heptafluoroisopropyl group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a trifluoromethoxy group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a trifluoromethylsulfanyl group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a trifluoromethylsulfinyl group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a trifluoromethylsulfonyl group, $A^2$ is a nitrogen atom, $A^4$ is CH, and $R^1$, $R^3$, $A^1$ and n are the combinations shown in [Table 1] to [Table 16].

In the formula (H-2), compounds wherein $R^{17}$ is a trifluoromethyl group, $A^2$ is CH, $A^4$ is a nitrogen atom, and $R^1$, $R^3$, $A^1$ and n are the combinations shown in [Table 1] to [Table 16].

In the formula (H-2), compounds wherein $R^{17}$ is a pentafluoroethyl group, $A^2$ is CH, $A^4$ is a nitrogen atom, and $R^1$, $R^3$, $A^1$ and n are the combinations shown in [Table 1] to [Table 16].

In the formula (H-2), compounds wherein $R^{17}$ is a heptafluoroisopropyl group, $A^2$ is CH, $A^4$ is a nitrogen atom, and $R^1$, $R^3$, $A^1$ and n are the combinations shown in [Table 1] to [Table 16].

In the formula (H-2), compounds wherein $R^{17}$ is a trifluoromethoxy group, $A^2$ is CH, $A^4$ is a nitrogen atom, and $R^1$, $R^3$, $A^1$ and n are the combinations shown in [Table 1] to [Table 16].

In the formula (H-2), compounds wherein $R^{17}$ is a trifluoromethylsulfanyl group, $A^2$ is CH, $A^4$ is a nitrogen atom, and $R^1$, $R^3$, $A^1$ and n are the combinations shown in [Table 1] to [Table 16].

In the formula (H-2), compounds wherein $R^{17}$ is a trifluoromethylsulfinyl group, $A^2$ is CH, $A^4$ is a nitrogen atom, and $R^1$, $R^3$, $A^1$ and n are the combinations shown in [Table 1] to [Table 16].

In the formula (H-2), compounds wherein $R^{17}$ is a trifluoromethylsulfonyl group, $A^2$ is CH, $A^4$ is a nitrogen atom, and $R^1$, $R^3$, $A^1$ and n are the combinations shown in [Table 1] to [Table 16].

In formula (J):

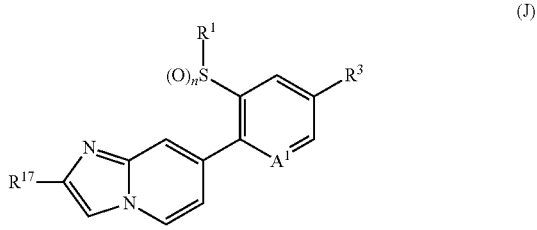

wherein symbols represent the same meaning as in the formula (1), compounds wherein $R^{17}$ is a trifluoromethyl group, and $R^1$, $R^3$, $A^1$ and n are the combinations shown in [Table 1] to [Table 16].

In the formula (J), compounds wherein $R^{17}$ is a pentafluoroethyl group, and $R^1$, $R^3$, $A^1$ and n are the combinations shown in [Table 1] to [Table 16].

In the formula (J), compounds wherein $R^{17}$ is a heptafluoroisopropyl group, and $R^1$, $R^3$, $A^1$ and n are the combinations shown in [Table 1] to [Table 16].

In the formula (J), compounds wherein $R^{17}$ is a trifluoromethoxy group, and $R^1$, $R^3$, $A^1$ and n are the combinations shown in [Table 1] to [Table 16].

In the formula (J), compounds wherein $R^{17}$ is a trifluoromethylsulfanyl group, and $R^1$, $R^3$, $A^1$ and n are the combinations shown in [Table 1] to [Table 16].

In the formula (J), compounds wherein $R^{17}$ is a trifluoromethylsulfinyl group, and $R^1$, $R^3$, $A^1$ and n are the combinations shown in [Table 1] to [Table 16].

In the formula (J), compounds wherein $R^{17}$ is a trifluoromethylsulfonyl group, and $R^1$, $R^3$, $A^1$ and n are the combinations shown in [Table 1] to [Table 16].

Examples of the pest on which the compound of the present invention has an effect include arthropod pests such as pest insects and pest mites and nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., *and Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. *and Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: *Culex* such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, *Stomoxys*, and Stomoxyidae.

Coleoptera: Corn rootworm such as *Diabrotica virgifera virgifera* and *Diabrotica undecimpunctata howardi*, Scarabaeidae such as *Anomala cuprea*, *Anomala rufocuprea*, and *Popillia japonica*, Curculionidae such as *Sitophilus zeamais*, *Lissorhoptrus oryzophilus*, *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, *Epilachna* such as *Epilachna vigintioctopunctata*, Lyctidae such as *Lyctus brunneus* and *Tomicus piniperda*, Bostrychidae, Ptinidae, Cerambycidae such as *Anoplophora malasiaca*, *Agriotes* spp., and *Paederus fuscipes*.

Orthoptera: *Locusta migratoria*, *Gryllotalpa africana*, *Oxya yezoensis*, *Oxya japonica*, and *Grylloidea*.

Siphonaptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophaga: *Dalmalinia ovis*, *Dalmalinia bovis*, *Menopon gallinae*, *Trichodectes canis*, *Felicola subrostrata*, and the like.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, and *Pratylenchus neglectus*.

Blattodea: *Blattella germanica*, *Periplaneta fuliginosa*, *Periplaneta americana*, *Periplaneta brunnea*, and *Blatta orientalis*.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes*

*satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae*, and the like.

Acarina: Tetranychidae such as *Tetranychus urticae, Tetranychus kanzawai, Panonychus citri, Panonychus ulmi*, and *Oligonychus* spp., Eriophyidae such as *Aculops pelekassi, Phyllocoptruta citri, Aculops lycopersici, Calacarus carinatus, Acaphylla theavagrans, Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus, Cheyletus malaccensis, Cheyletus moorei*, and *Cheyletiella yasguri*, Sarcoptidae such as *Octodectes cynotis* and *Sacroptes scabiei*, Demodicidae such as *Demodex canis*, Listrophoridae, Oribatei, Dermanyssidae such as *Ornithonyssus bacoti, Ornithonyssus sylvairum*, and *Dermanyssus gallinae*, Trombiculidae such as *Leptotrombidium akamushi*, Arachnida such as *Chiracanthium japonicum* and *Latrodectus hasseltii*, and the like.

Chilopoda: *Thereuonema hilgendorfi, Scolopendra subspinipes*, and the like.

Diplopoda: *Oxidus gracilis, Nedyopus tambanus*, and the like.

Isopoda: *Armadillidium vulgare*, and the like.

Gastropoda: *Limaxmarginatus, Limax flavus*, and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, granules, wettable powders, flowables, microcapsule formulations, aerosols, smoking agents, poisonous baits, resin formulations, shampoo agents, paste formulations, foam agents, carbon dioxide preparations, tablets, and the like. These formulations may be processed into mosquito repellent coils, electric mosquito repellent mats, mosquito repellent liquid formulations, smoking agents, fumigants, sheet formulations, spot-on agents, or oral treatment agents, and used. The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc), synthetic hydrated silicon oxide, talc, ceramics, other inorganic minerals (sericite, quartz, sulfur, activated carbon, calcium carbonate, hydrated silica, etc), fine powder and granulated substances of chemical fertilizers (ammonium sulfate, ammonium phosphate, ammonium nitrate, urea, ammonium chloride, etc.) and the like, and synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc), ketones (acetone, methyl ethyl ketone, cyclohexanone, etc), aromatic hydrocarbons (toluene, xylene, ethylbenzene, dodecylbenzene, phenylxylylethane, methylnaphthalene, etc), aliphatic hydrocarbons (hexane, cyclohexane, kerosene, light oil, etc), esters (ethyl acetate, butyl acetate, isopropyl myristate, ethyl oleate, diisopropyl adipate, diisobutyl adipate, propylene glycol monomethyl ether acetate, etc), nitriles (acetonitrile, isobutyronitrile, etc), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc), acid amides (DMF, N,N-dimethylacetamide, etc), halogenated hydrocarbons (dichloromethane, trichloroethane, carbon tetrachloride, etc), sulfoxides (DMSO, etc), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc), lignin derivatives, bentonite, synthetic water-soluble polymers (polyvinyl alcohol, polyvinyl pyrrolidone, polyacrylic acid, etc), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc), ester adipates or stearic acid may be added to these base materials as necessary. The resin formulation is obtained by kneading a compound into the base material using an ordinary kneading apparatus, and then molding it by injection molding, extrusion molding, press molding or the like, and can be processed into a plate, film, taped, reticular or string resin formulation by further undergoing molding or cutting step as necessary. These resin formulation is processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant such as cheese flavor, onion flavor and peanut oil or the like are added as necessary.

The method for controlling pests of the present invention is carried out by applying an effective amount of the compound of the present invention to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g per the amount of the compound of the present invention per 10000 m². When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on a pest or a plant such as crops which should be protected from pests, and also may be applied on a soil in order to control a pest that infests in the soil of cultivated land.

Also, the resin formulation processed into a sheet or string can be also applied by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 m² of an area to be treated, in the case of using it on a planar area, and is usually 0.01 to 500 mg in an amount of the compound of the present invention per 1 m³ of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, smoking agents, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention when administered to an animal body is usually within the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc), Cucurbitaceae vegetables (cucumber, pumpkin, zucchini, watermelon, melon, etc), Cruciferae vegetables (Japanese radish, turnip, horseradish, kohlrabi, Chinese cabbage, cabbage, brown mustard, broccoli, cauliflower, etc), Compositae vegetables (burdock, garland chrysanthemum, artichoke, lettuce, etc), Liliaceae vegetables (Welsh onion, onion, garlic, asparagus, etc), Umbelliferae vegetables (carrot, parsley, celery, parsnip, etc), Chenopodiaceae vegetables (spinach, Swiss chard, etc), Labiatae vegetables (Japanese mint, mint, basil, etc), strawberry, sweat potato, yam, aroid, etc.

Fruit trees: pomaceous fruits (apple, common pear, Japanese pear, Chinese quince, quince, etc), stone fleshy fruits (peach, plum, nectarine, Japanese plum, cherry, apricot, prune, etc), citrus plants (Satsuma mandarin, orange, lemon, lime, grapefruits, etc), nuts (chestnut, walnut, hazel nut, almond, pistachio, cashew nut, macadamia nut, etc), berry fruits (blueberry, cranberry, blackberry, raspberry, etc), grape, persimmon, olive, loquat, banana, coffee, date, coconut, oil palm, etc.

Trees other than fruit trees: tea, mulberry, flowering trees and shrubs (azalea, camellia, hydrangea, sasanqua, Illicium religiosum, cherry tree, tulip tree, crape myrtle, fragrant olive, etc), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horsechestnut, etc), sweet viburnum, Podocarpus macrophyllus, Japanese cedar, Japanese cypress, croton, spindle tree, Chainese howthorn, etc.

Lawn: zoysia (Japanese lawn grass, mascarene grass, etc), Bermuda grass (Cynodon dactylon, etc), bent grass (creeping bent grass, Agrostis stolonifera, Agrostis tenuis, etc), bluegrass (Kentucky bluegrass, rough bluegrass, etc), fescue (tall fescue, chewing fescue, creeping fescue, etc), ryegrass (darnel, perennial ryegrass, etc), cocksfoot, timothy grass, etc.

Others: flowers (rose, carnation, chrysanthemum, Eustoma grandiflorum Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc), bio-fuel plants (Jatropha, curcas, safflower, Camelina alyssum, switchgrass, miscanthus, reed canary grass, Arundo donax, kenaf, cassava, willow, algae, etc), foliage plants, etc.

The "crops" also contains genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropylether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogenphosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, and 2,3,5,6-tetrafluoro-4-(methoxymethyl)benzyl(1RS,3RS;1RS,3SR)-2,2-dimethyl-3-(2-methyl-1-propenyl)cyclopropanecarboxylate, 2,3,5,6-tetrafluoro-4-(methoxymethyl)benzyl(EZ)-(1RS,3RS;1RS,3SR)-2,2-dimethyl-3-(2-cyano-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof;

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, compounds represented by the following formula (K):

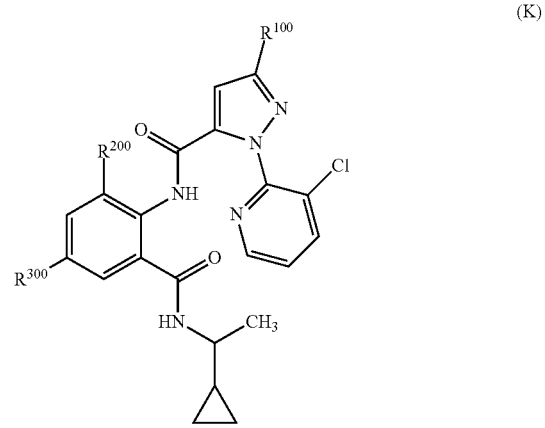

wherein
$R^{100}$ represents chlorine, bromine or a trifluoromethyl group,
$R^{200}$ represents chlorine, bromine or a methyl group, and
$R^{300}$ represents chlorine, bromine or a cyano group, and
compounds represented by the following formula (L):

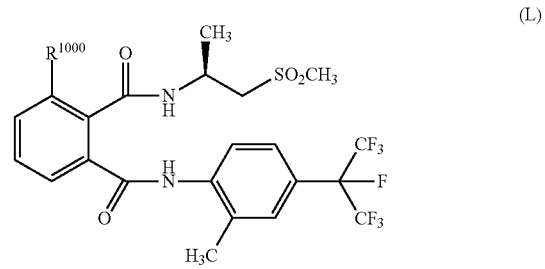

wherein
$R^{1000}$ represents chlorine, bromine or iodine.

Active Ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active Ingredients of Fungicide azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol; Cyclic amine fungicidal compounds such as fenpropimorph, tridemorph, and fenpropidin; Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid;

folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Herbicide (1) Phenoxy Fatty Acid Herbicidal Compounds
2,4-PA, MCP, MCPB, phenothiol, mecoprop, fluroxypyr, triclopyr, clomeprop, and naproanilide.

(2) Benzoate Herbicidal Compounds
2,3,6-TBA, dicamba, clopyralid, picloram, aminopyralid, quinclorac, and quinmerac.

(3) Urea Herbicidal Compounds
diuron, linuron, chlortoluron, isoproturon, fluometuron, isouron, tebuthiuron, methabenzthiazuron, cumyluron, daimuron, and methyl-daimuron.

(4) Triazine Herbicidal Compounds
atrazine, ametoryn, cyanazine, simazine, propazine, simetryn, dimethametryn, prometryn, metribuzin, triaziflam, and indaziflam.

(5) Bipyridinium Herbicidal Compounds
paraquat, and diquat.

(6) Hydroxybenzonitrile Herbicidal Compounds
bromoxynil, and ioxynil.

(7) Dinitroaniline herbicidal compounds
pendimethalin, prodiamine, and trifluralin.

(8) Organophosphorus Herbicidal Compounds
amiprofos-methyl, butamifos, bensulide, piperophos, anilofos, glyphosate, glufosinate, glufosinate-P, and bialaphos.

(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.

(10) Acid Amide Herbicidal Compounds
propanil, propyzamide, bromobutide, and etobenzanid.

(11) Chloroacetanilide Herbicidal Compounds
acetochlor, alachlor, butachlor, dimethenamid, propachlor, metazachlor, metolachlor, pretilachlor, thenylchlor, and pethoxamid.

(12) Diphenyl Ether Herbicidal Compounds
acifluorfen-sodium, bifenox, oxyfluorfen, lactofen, fomesafen, chlomethoxynil, and aclonifen.

(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds
benzofenap, pyrazolate, pyrazoxyfen, topramezone, and pyrasulfotole.

(15) Triketone Herbicidal Compounds
isoxaflutole, benzobicyclon, sulcotrione, mesotrione, tembotrione, and tefuryltrione.

(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.

(17) Trione Oxime Herbicidal Compounds
alloxydim-sodium, sethoxydim, butroxydim, clethodim, cloproxydim, cycloxydim, tepraloxydim, tralkoxydim, and profoxydim.

(18) Sulfonyl Urea Herbicidal Compounds
chlorsulfuron, sulfometuron-methyl, metsulfuron-methyl, chlorimuron-ethyl, tribenuron-methyl, triasulfuron, metsulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds
imazamethabenz-methyl, imazamethapyr, imazamox, imazapyr, imazaquin, and imazethapyr.

(20) Sulfonamide Herbicidal Compounds
flumetsulam, metosulam, diclosulam, florasulam, cloransulam-methyl, penoxsulam, and pyroxsulam.

(21) Pyrimidinyloxybenzoate Herbicidal Compounds
pyrithiobac-sodium, bispyribac-sodium, pyriminobac-methyl, pyribenzoxim, pyriftalid, and pyrimisulfan.

(22) Other Herbicidal Compounds
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Plant Growth Regulator
hymexazol, paclobutrazol, uniconazole-P, inabenfide, prohexadione-calcium, aviglycine, 1-naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride and 4-CPA (4-chlorophenoxyacetic acid).

Active Ingredients of Synergist
piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, CH$_3$I, t-phenylbutenone, diethyl maleate, DIIC, FDMC, ETP, and ETN.

EXAMPLES

Hereinbelow, the present invention will be further described in detail by production examples, reference examples, formulation examples, test examples, and the like. However, the present invention is not limited to these examples.

First, the production examples for the production of the compounds of the present invention are shown below.

Production Example 1 (1)

A mixture of 14.1 g of 1-bromo-2-ethylsulfanylbenzene and 65 mL of THF was cooled to −70° C., and 44.7 ml of n-butyl lithium (1.63M hexane solvent) was added at a rate such that the internal temperature of the mixture was kept at −60° C. or less, and the mixture was stirred at −50° C. for 30 minutes. A mixture of 14 g of isopropoxyboronic acid pinacol ester and 5 mL of THF was added at a rate such that the internal temperature of the mixture was kept at −60° C. or less, and the mixture was heated to the room temperature. Water was added to the reaction mixture, and the mixture was extracted with ethyl acetate. The organic layer was washed with water, then dried over anhydrous sodium sulfate and concentrated under reduced pressure. The resulting residue was applied to a silica gel column chromatography to obtain 7.9 g of 2-ethylsulfanylphenylboronic acid pinacol ester.

2-Ethylsulfanylphenylboronic Acid Pinacol Ester

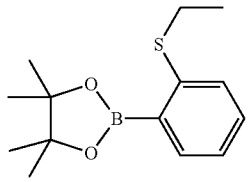 [SMILES: CCSc1ccccc1B1OC(C)(C)C(C)(C)O1]

$^1$H-NMR (CDCl$_3$) δ: 7.63 (1H, dd), 7.33 (1H, td), 7.28-7.25 (1H, m), 7.12 (1H, td), 2.93 (2H, q), 1.38 (12H, s), 1.33 (3H, t).

Production Example 1 (2)

A mixture of 0.52 g of 2-ethylsulfanylphenylboronic acid pinacol ester, 0.46 g of 2-chloro-6-trifluoromethylquinoxaline, 0.02 g of tris(dibenzylideneacetone)dipalladium(0), 0.05 g of 2-dicyclohexylphosphino-2',6'-dimethoxyphenyl, 0.84 g of tripotassium phosphate and 6 ml of 1,4-dioxane was stirred at 70° C. for 2 hours. 0.30 g of tripotassium phosphate was added to the cooled reaction mixture, and the mixture was stirred under heat-reflux for 3 hours. Ethyl acetate and water were added to the cooled reaction mixture, and the mixture was filtered. The filtrate was extracted with ethyl acetate and then dried over anhydrous sodium sulfate. The mixture was concentrated under reduced pressure, and the resulting residue was applied to a silica gel column chromatography to obtain 0.28 g of 2-(2-ethylsulfanylphenyl)-6-trifluoromethylquinoxaline (Compound of Present Invention 1).

Compound of Present Invention 1

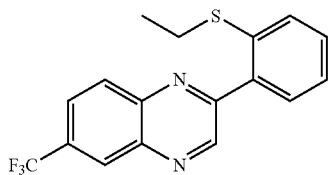 [SMILES: CCSc1ccccc1-c1cnc2cc(C(F)(F)F)ccc2n1]

$^1$H-NMR (CDCl$_3$) δ: 9.28 (1H, s), 8.49 (1H, s), 8.28 (1H, d), 7.96 (1H, dd), 7.64 (1H, dd), 7.57 (1H, dd), 7.49 (1H, td), 7.41 (1H, td), 2.85 (2H, q), 1.22 (3H, t).

Production Example 2

A mixture of 0.52 g of 2-ethylsulfanylphenylboronic acid pinacol ester, 0.40 g of 2-chloro-3-methyl-6-trifluoromethylquinoxaline, 0.02 g of tris(dibenzylideneacetone)dipalladium(0), 0.05 g of 2-dicyclohexylphosphino-2',6'-dimethoxyphenyl, 0.84 g of tripotassium phosphate and 6 ml of 1,4-dioxane was stirred at 70° C. for 2 hours. 0.30 g of tripotassium phosphate was added to the cooled reaction mixture, and the mixture was stirred under heat-reflux for 3 hours. Ethyl acetate and water were added to the cooled reaction mixture, and the mixture was filtered. The filtrate was extracted with ethyl acetate and then dried over anhydrous sodium sulfate. The mixture was concentrated under reduced pressure, and the resulting residue was applied to a silica gel column chromatography to obtain 0.21 g of 2-(2-ethylsulfanylphenyl)-3-methyl-6-trifluoromethylquinoxaline (Compound of Present Invention 2).

Compound of Present Invention 2

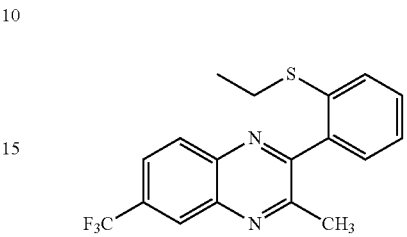

$^1$H-NMR (CDCl$_3$) δ: 8.43 (1H, s), 8.20 (1H, d), 7.94 (1H, dd), 7.55-7.31 (4H, m), 2.82 (2H, q), 2.62 (3H, s), 1.20 (3H, t).

Production Example 3 (1)

A mixture of 1.0 g of 2-amino-4-trifluromethylbenzamide, 813 mg of 2-ethylsulfanylbenzaldehyde, 764 mg of sodium bisulfite and 4 ml of DMA was stirred at 150° C. for 8 hours. A saturated aqueous sodium bicarbonate solution and water were added to the cooled reaction mixture, and the precipitated solid was filtered. The resulting solid was washed with water and n-hexane and then dried to obtain 1.49 g of 2-(2-ethylsulfanylphenyl)-7-trifluoromethyl-3H-quinazolin-4-one.

2-(2-Ethylsulfanylphenyl)-7-trifluoromethyl-3H-quinazolin-4-one

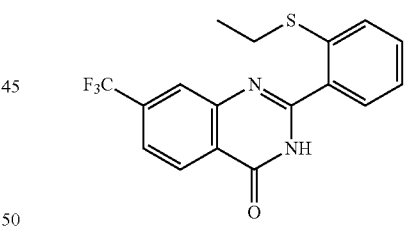

$^1$H-NMR (CDCl$_3$) δ: 10.46 (1H, brs), 8.43 (1H, d), 8.11 (1H, s), 7.91 (1H, dd), 7.72 (1H, dd), 7.54 (1H, dd), 7.50 (1H, td), 7.41 (1H, td), 2.92 (2H, q), 1.28 (3H, t).

Production Example 3 (2)

A mixture of 500 mg of 2-(2-ethylsulfanylphenyl)-7-trifluoromethyl-3H-quinazolin-4-one, 615 mg of phosphorus oxybromide and 2 ml of acetonitrile was refluxed for 4 hours. A saturated aqueous sodium bicarbonate solution was added to the cooled reaction mixture, and the mixture was extracted with ethyl acetate. The organic layer was washed with water and dried over anhydrous magnesium sulfate, and then concentrated under reduced pressure. The resulting residue was applied to a silica gel column chromatography to obtain 149 mg of 4-bromo-2-(2-ethylsulfanylphenyl)-7-trifluoromethylquinazoline (Compound of Present Invention 3).

Compound of Present Invention 3

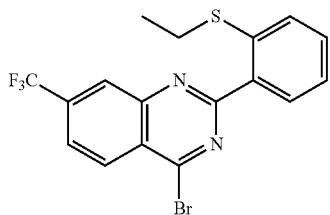

$^1$H-NMR (CDCl$_3$) δ: 8.44 (1H, s), 8.37 (1H, d), 8.22 (1H, dd), 7.88 (1H, dd), 7.48-7.44 (2H, m), 7.31 (1H, td), 3.01 (2H, q), 1.34 (3H, t).

Production Example 4

A mixture of 1.29 g of 2-(2-ethylsulfanylphenyl)-7-trifluoromethyl-3H-quinazolin-4-one, 0.38 ml of phosphorus oxychloride, 523 mg of N,N-diisopropylethylamine and 20 ml of toluene was stirred at 90° C. for 2 hours. A saturated aqueous sodium bicarbonate solution was added to the cooled reaction mixture, and the mixture was extracted with ethyl acetate. The organic layer was washed with water and dried over anhydrous magnesium sulfate, then concentrated under reduced pressure to obtain 1.23 g of 4-chloro-2-(2-ethylsulfanylphenyl)-7-trifluoromethylquinazoline (Compound of Present Invention 4).

Compound of Present Invention 4

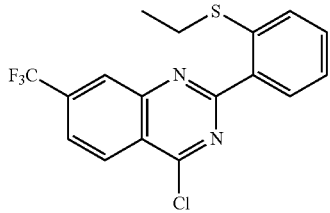 [SMILES: CCSc1ccccc1-c1nc(Cl)c2ccc(C(F)(F)F)cc2n1]

$^1$H-NMR (CDCl$_3$) δ: 8.46 (1H, s), 8.43 (1H, d), 8.20 (1H, d), 7.88 (1H, d), 7.50-7.43 (2H, m), 7.33-7.28 (1H, m), 3.00 (2H, q), 1.34 (3H, t).

Production Example 5

4.5 ml of a 28% aqueous ammonia solution was added to a mixture of 500 mg of 4-chloro-2-(2-ethylsulfanylphenyl)-7-trifluoromethylquinazoline, 8 ml of THF and 5 ml of acetonitrile, and the mixture was stirred at 50° C. for 2 hours. Water was added to the cooled reaction mixture, and the mixture was extracted with t-butyl methyl ether. The organic layer was washed with water and dried over anhydrous magnesium sulfate, and then concentrated under reduced pressure. The resulting residue was applied to a silica gel column chromatography to obtain 396 mg of 4-amino-2-(2-ethylsulfanylphenyl)-7-trifluoromethylquinazoline (Compound of Present Invention 5).

Compound of Present Invention 5

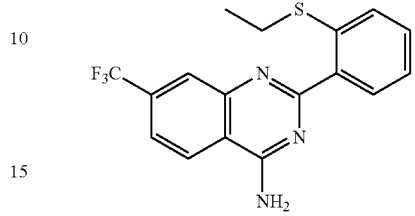

$^1$H-NMR (CDCl$_3$) δ: 8.28 (1H, s), 7.92 (1H, dd), 7.89 (1H, d), 7.68 (1H, dd), 7.44-7.37 (2H, m), 7.28-7.24 (1H, m), 5.81 (2H, brs), 2.95 (2H, q), 1.30 (3H, t).

Production Example 6

0.5 ml of n-propylamine was added to a mixture of 450 mg of 4-chloro-2-(2-ethylsulfanylphenyl)-7-trifluoromethylquinazoline, 3 ml of acetonitrile and 3 ml of THF, and the mixture was stirred at room temperature for 30 minutes. Water was added to the reaction mixture, and the mixture was extracted with ethyl acetate. The organic layer was washed with water and dried over anhydrous magnesium sulfate, and then concentrated under reduced pressure to obtain 495 mg of 2-(2-ethylsulfanylphenyl)-4-propylamino-7-trifluoromethylquinazoline (Compound of Present Invention 8).

Compound of Present Invention 8

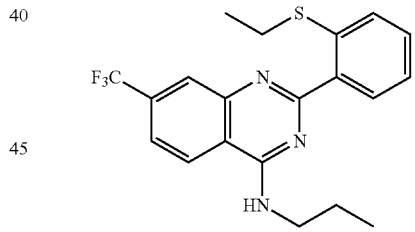

$^1$H-NMR (CDCl$_3$) δ: 8.23 (1H, s), 8.10 (1H, dd), 7.82 (1H, d), 7.62 (1H, dd), 7.44-7.36 (2H, m), 7.28-7.22 (1H, m), 5.82 (1H, brs), 3.82-3.76 (2H, m), 2.96 (2H, q), 1.86-1.75 (2H, m), 1.32 (3H, t), 1.07 (3H, t).

Production Example 7

281 mg of 3-chloroperbenzoic acid (purity of 65% or more) was added to a mixture of 305 mg of 2-(2-ethylsulfanylphenyl)-4-propylamino-7-trifluoromethylquinazoline and 4 ml of chloroform, under ice cooling, and the mixture was stirred at room temperature for 4 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure. The resulting residue was applied to a silica gel column chromatography to obtain 174 mg of 2-(2-ethylsulfinylphenyl)-4-propylamino-7-trifluoromethylquinazoline (Compound of Present Invention 9) and 100 mg of 2-(2-ethylsulfonylphenyl)-4-propylamino-7-trifluoromethylquinazoline (Compound of Present Invention 10).

Compound of Present Invention 9

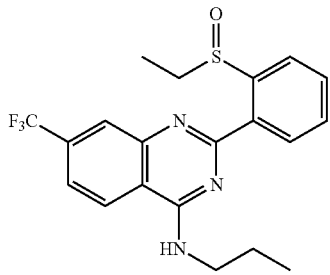 [SMILES: CCCNc1nc(-c2ccccc2S(=O)CC)nc2cc(C(F)(F)F)ccc12]

$^1$H-NMR (CDCl$_3$) δ: 8.63 (1H, dd), 8.31 (1H, dd), 8.09 (1H, s), 7.87 (1H, d), 7.72 (1H, td), 7.67-7.58 (2H, m), 5.99 (1H, brs), 3.90-3.69 (2H, m), 3.58-3.47 (1H, m), 2.94 (1H, d), 1.89-1.79 (2H, m), 1.40 (3H, t), 1.10 (3H, t).

Compound of Present Invention 10

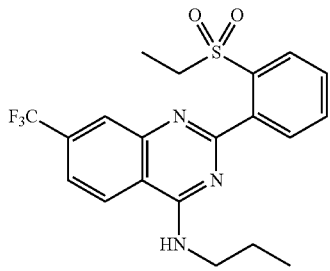 [SMILES: CCCNc1nc(-c2ccccc2S(=O)(=O)CC)nc2cc(C(F)(F)F)ccc12]

$^1$H-NMR (CDCl$_3$) δ: 8.14 (1H, dd), 8.01 (1H, s), 7.83-7.71 (3H, m), 7.67-7.59 (1H, m), 7.55 (1H, dd), 6.08 (1H, brs), 3.91 (2H, q), 3.48-3.40 (2H, m), 1.72-1.59 (2H, m), 1.41 (3H, t), 0.97 (3H, t).

Production Example 8

324 mg of t-butyl nitrite was added to a mixture of 506 mg of 4-amino-2-(2-ethylsulfanylphenyl)-7-trifluoromethylquinazoline and 10 ml of DMF at 100° C., and the mixture was stirred at 100° C. for 45 minutes. Water was added to the cooled reaction mixture, and the mixture was extracted with t-butyl methyl ether. The organic layer was washed with water and dried over anhydrous magnesium sulfate, and then concentrated under reduced pressure. The resulting residue was applied to a silica gel column chromatography to obtain 74 mg of 2-(2-ethylsulfanylphenyl)-7-trifluoromethylquinazoline (Compound of Present Invention 11).

Compound of Present Invention 11

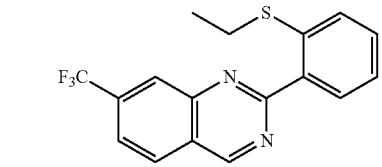 [SMILES: CCSc1ccccc1-c1ncc2ccc(C(F)(F)F)cc2n1]

$^1$H-NMR (CDCl$_3$) δ: 9.60 (1H, s), 8.46 (1H, s), 8.15 (1H, dd), 8.11 (1H, d), 7.84 (1H, dd), 7.50-7.43 (2H, m), 7.32 (1H, td), 2.99 (2H, q), 1.32 (3H, t).

Production Example 9

117 mg of 3-chloroperbenzoic acid (purity of 65% or more) was added to a mixture of 175 mg of 2-(2-ethylsulfanylphenyl)-7-trifluoromethylquinazoline and 3 ml of chloroform, under ice cooling, and the mixture was stirred at room temperature for 6 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure to obtain 87 mg of 2-(2-ethylsulfonylphenyl)-7-trifluoromethylquinazoline (Compound of Present Invention 12).

Compound of Present Invention 12

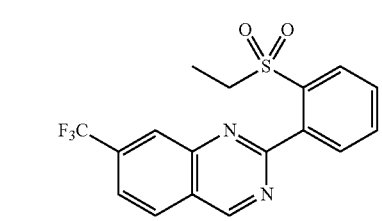 [SMILES: CCS(=O)(=O)c1ccccc1-c1ncc2ccc(C(F)(F)F)cc2n1]

$^1$H-NMR (CDCl$_3$) δ: 9.58 (1H, s), 8.35 (1H, s), 8.20-8.14 (2H, m), 7.95-7.67 (4H, m), 3.84 (2H, q), 1.42 (3H, t).

Production Example 10

2.1 ml of methylmagnesium bromide (a 1 M THF solution) was added to a mixture of 380 mg of 4-chloro-2-(2-ethylsulfanylphenyl)-7-trifluoromethylquinazoline, 72 mg of iron (III) acetylacetonate, 8 ml of THF and 0.8 ml of NMP, and the mixture was stirred at room temperature for 1 hour. Ethyl acetate and water were added to the reaction mixture, and the mixture was filtered. The aqueous layer of the filtrate was extracted with ethyl acetate, combined with the organic layer of the filtrate, sequentially washed with 0.5 N hydrochloric acid, water and saturated aqueous sodium chloride, dried over anhydrous magnesium sulfate, and then concentrated under reduced pressure. The mixture was concentrated under reduced pressure, and the resulting residue was applied to a silica gel column chromatography to obtain 123 mg of 2-(2-ethylsulfanylphenyl)-4-methyl-7-trifluoromethylquinazoline (Compound of Present Invention 13).

Compound of Present Invention 13

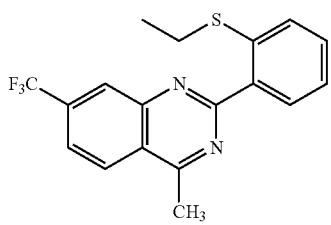 [SMILES: CCSc1ccccc1-c1nc(C)c2ccc(C(F)(F)F)cc2n1]

¹H-NMR (CDCl₃) δ: 8.43 (1H, d), 8.26 (1H, d), 8.10 (1H, dd), 7.80 (1H, dd), 7.47 (1H, dd), 7.44 (1H, td), 7.30 (1H, td), 3.08 (3H, s), 2.98 (2H, q), 1.31 (3H, t).

Production Example 11 (1)

A mixture of 4.0 g of 4-chloro-2-fluorobenzaldehyde, 2.05 ml of ethanethiol, 3.82 g of potassium carbonate and 6 ml of DMF was stirred at room temperature for 6 hours, and was allowed to stand overnight. Water was added to the reaction mixture, and the mixture was extracted with ethyl acetate. The organic layer was washed with water, then dried over anhydrous magnesium sulfate, and concentrated under reduced pressure. The resulting residue was applied to a silica gel column chromatography to obtain 3.57 g of 4-chloro-2-ethylsulfanylbenzaldehyde. 4-Chloro-2-ethylsulfanylbenzaldehyde

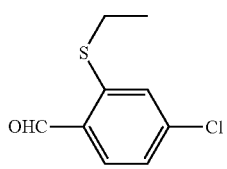

¹H-NMR (CDCl₃) δ: 10.28 (1H, s), 7.76 (1H, d), 7.36 (1H, d), 7.28-7.24 (1H, m), 3.00 (2H, q), 1.40 (3H, t).

Production Example 11 (2)

A mixture of 1.0 g of 2-amino-4-trifluromethylbenzamide, 944 mg of 4-chloro-2-ethylsulfanylbenzaldehyde, 765 mg of sodium bisulfite and 4 ml of DMA was stirred at 150° C. for 15 hours. A saturated aqueous sodium bicarbonate solution and water were added to the cooled reaction mixture, and the precipitated solid was filtered. The resulting solid was washed with water and n-hexane and then dried to obtain 1.46 g of 2-(4-chloro-2-ethylsulfanylphenyl)-7-trifluoromethyl-3H-quinazolin-4-one.

2-(4-Chloro-2-ethylsulfanylphenyl)-7-trifluoromethyl-3H-quinazolin-4-one

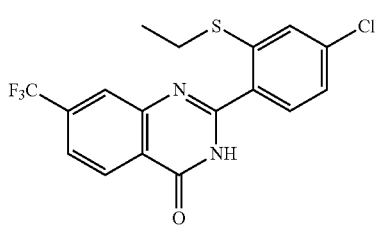 [SMILES: CCSc1cc(Cl)ccc1-c1nc2cc(C(F)(F)F)ccc2c(=O)[nH]1]

¹H-NMR (CDCl₃) δ: 8.43 (1H, d), 8.09 (1H, s), 7.84 (1H, d), 7.73 (H, d), 7.47 (1H, s), 7.36 (1H, d), 2.95 (2H, q), 1.32 (3H, t).

Production Example 11 (3)

A mixture of 1.46 g of 2-(4-chloro-2-ethylsulfanylphenyl)-7-trifluoromethyl-3H-quinazolin-4-one, 0.39 ml of phosphorus oxychloride, 538 mg of N,N-diisopropylethylamine and 20 ml of toluene was stirred at 90° C. for 1 hour. A saturated aqueous sodium bicarbonate solution was added to the cooled reaction mixture, and the mixture was extracted with ethyl acetate. The organic layer was washed with water and dried over anhydrous magnesium sulfate, and then concentrated under reduced pressure to obtain 1.31 g of 4-chloro-2-(4-chloro-2-ethylsulfanylphenyl)-7-trifluoromethylquinazoline (Compound of Present Invention 14).

Compound of Present Invention 14

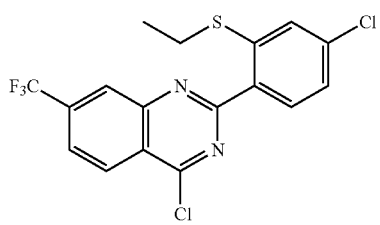 [SMILES: CCSc1cc(Cl)ccc1-c1nc(Cl)c2ccc(C(F)(F)F)cc2n1]

¹H-NMR (CDCl₃) δ: 8.45 (1H, s), 8.42 (1H, d), 8.25 (1H, d), 7.89 (1H, dd), 7.41 (1H, d), 7.29-7.25 (1H, m), 3.01 (2H, q), 1.38 (3H, t).

Production Example 12

1.5 ml of ethylamine (a 70% aqueous solution) was added to a mixture of 600 mg of 4-chloro-2-(4-chloro-2-ethylsulfanylphenyl)-7-trifluoromethylquinazoline and 10 ml of THF, and the mixture was stirred at room temperature for 20 minutes. The reaction mixture was concentrated under reduced pressure, and a saturated aqueous sodium bicarbonate solution was added to the residue, and then the mixture was extracted with ethyl acetate. The organic layer was washed with water and concentrated under reduced pressure to obtain 606 mg of 2-(4-chloro-2-ethylsulfanylphenyl)-4-ethylamino-7-trifluoro methylquinazoline (Compound of Present Invention 15).

Compound of Present Invention 15

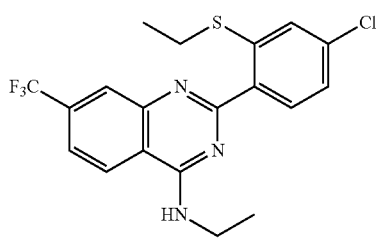 [SMILES: CCNc1nc(-c2ccc(Cl)cc2SCC)nc2cc(C(F)(F)F)ccc12]

¹H-NMR (CDCl₃) δ: 8.21 (1H, s), 8.11 (1H, d), 7.82 (1H, d), 7.63 (1H, dd), 7.35 (1H, d), 7.21 (1H, dd), 5.78 (1H, brs), 3.89-3.81 (2H, m), 2.96 (2H, q), 1.41 (3H, t), 1.35 (3H, t).

Production Example 13

375 mg of 3-chloroperbenzoic acid (purity of 65% or more) was added to a mixture of 306 mg of 2-(4-chloro-2-ethylsulfanylphenyl)-4-ethylamino-7-trifluoro methylquinazoline and 5 ml of chloroform, under ice cooling, and the mixture was stirred at room temperature for 4 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure. The resulting residue was applied to a silica gel column chromatography to obtain 270 mg of 2-(4-chloro-2-ethylsulfonylphenyl)-4-ethylamino-7-trifluoro methylquinazoline (Compound of Present Invention 16).

Compound of Present Invention 16

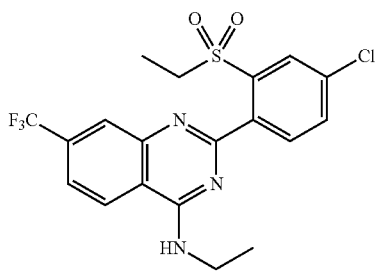 [SMILES: CCNc1nc(-c2ccc(Cl)cc2S(=O)(=O)CC)nc2cc(C(F)(F)F)ccc12]

$^1$H-NMR (CDCl$_3$) δ: 8.13 (1H, d), 8.01 (1H, s), 7.82 (1H, d), 7.77 (1H, d), 7.70 (1H, dd), 7.62 (1H, dd), 5.92 (1H, brs), 3.93 (2H, q), 3.69-3.61 (2H, m), 1.42 (3H, t), 1.33 (3H, t).

Production Example 14 (1)

A mixture of 5.14 g of 3-amino-2-chloro-5-trifluoromethylpyridine, 3.92 g of zinc cyanide, 1.19 g of tris(dibenzylideneacetone)dipalladium(0), 1.45 g of 1,1'-bis(diphenylphosphino)ferrocene and 20 ml of DMF was stirred at 150° C. for 40 minutes. Ethyl acetate and water were added to the cooled reaction mixture, and the mixture was filtered. The aqueous layer of the filtrate was extracted with ethyl acetate, then combined with the organic layer of the filtrate and washed with water, and dried over anhydrous magnesium sulfate. The mixture was concentrated under reduced pressure, and then the resulting residue was applied to a silica gel column chromatography to obtain 2.23 g of 3-amino-2-cyano-5-trifluoromethylpyridine.

3-Amino-2-cyano-5-trifluoromethylpyridine

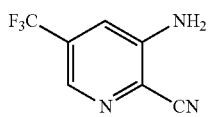

$^1$H-NMR (CDCl$_3$) δ: 8.29 (1H, d), 7.33 (1H, d), 4.70 (2H, s).

Production Example 14 (2)

2 ml of a 30% aqueous hydrogen peroxide solution was added to a mixture of 100 mg of 3-amino-2-cyano-5-trifluoromethylpyridine, 2 ml of a 10% aqueous sodium hydroxide solution and 6 ml of methanol, under ice cooling, and the mixture was stirred at room temperature for 1 hour. Water was added to the reaction mixture, and the mixture was extracted with t-butyl methyl ether. The organic layer was washed with a 10% aqueous sodium thiosulfate solution and dried over anhydrous magnesium sulfate, and then concentrated under reduced pressure to obtain 100 mg of 3-amino-5-trifluoromethylpyridine-2-carboxylic acid amide.

3-Amino-5-trifluoromethylpyridine-2-carboxylic acid amide

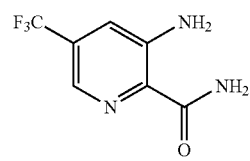 [SMILES: NC(=O)c1ncc(C(F)(F)F)cc1N]

$^1$H-NMR (CDCl$_3$) δ: 8.08 (1H, d), 7.85 (1H, brs), 7.22 (1H, d), 6.19 (2H, brs), 5.49 (1H, brs).

Production Example 14 (3)

A mixture of 1.0 g of 3-amino-5-trifluoromethylpyridine-2-carboxylic acid amide, 850 mg of 2-ethylsulfanylbenzaldehyde, 1.60 g of sodium bisulfite and 3 ml of DMA was stirred at 150° C. for 20 hours. Water was added to the cooled reaction mixture, and the mixture was extracted with ethyl acetate. The organic layer was washed with water, then dried over anhydrous magnesium sulfate, and concentrated under reduced pressure. The resulting residue was applied to a silica gel column chromatography to obtain 927 mg of 2-(2-ethylsulfanylphenyl)-7-trifluoromethyl-3H-pyrido[3,2-d]pyrimidin-4-one.

2-(2-Ethylsulfanylphenyl)-7-trifluoromethyl-3H-pyrido[3,2-d]pyrimidin-4-one

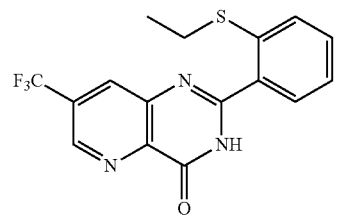 [SMILES: CCSc1ccccc1-c1nc2cc(C(F)(F)F)cnc2c(=O)[nH]1]

$^1$H-NMR (CDCl$_3$) δ: 10.79 (1H, brs), 9.07 (1H, d), 8.41 (1H, d), 7.98 (1H, dd), 7.57 (1H, dd), 7.53 (1H, td), 7.43 (1H, td), 2.95 (2H, q), 1.30 (3H, t).

Production Example 14 (4)

A mixture of 400 mg of 2-(2-ethylsulfanylphenyl)-7-trifluoromethyl-3H-pyrido[3,2-d]pyrimidin-4-one, 0.16 ml of phosphorus oxychloride, 221 mg of N,N-diisopropylethylamine and 6 ml of toluene was stirred at 100° C. for 30 minutes. The reaction mixture was cooled, and the precipitated solid was filtered. The resulting solid was sequentially washed with a saturated aqueous sodium bicarbonate solution, water and toluene, and then dried to obtain 320 mg of 4-chloro-2-(2-ethylsulfanylphenyl)-7-trifluoromethylpyrido[3,2-d]pyrimidine (Compound of Present Invention 17).

Compound of Present Invention 17

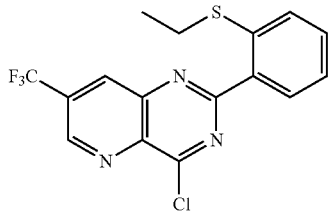 [SMILES: CCSc1ccccc1-c1nc(Cl)c2ncc(C(F)(F)F)cc2n1]

¹H-NMR (CDCl₃) δ: 9.27 (1H, d), 8.74 (1H, d), 8.27 (1H, d), 7.51-7.47 (2H, m), 7.35-7.30 (1H, m), 3.02 (2H, q), 1.35 (3H, t).

Production Example 15 (1)

41 µl of hydrazine monohydrate was added to a mixture of 263 mg of 4-chloro-2-(2-ethylsulfanylphenyl)-7-trifluoromethylpyrido[3,2-d]pyrimidine and 4 ml of THF, under ice cooling, and the mixture was stirred at room temperature for 15 minutes. A saturated aqueous sodium bicarbonate solution was added to the reaction mixture, and the mixture was extracted with t-butyl methyl ether. The organic layer was washed with water and then concentrated under reduced pressure to obtain 246 m of [2-(2-ethylsulfanylphenyl)-7-trifluoromethylpyrido[3,2-d]pyrimidin-4-yl]-hydrazine.

[2-(2-Ethylsulfanylphenyl)-7-trifluoromethylpyrido[3,2-d]pyrimidin-4-yl]-hydrazine

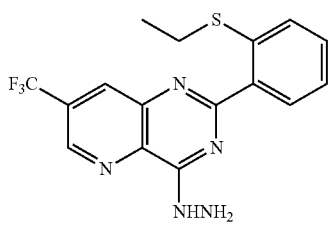 [SMILES: CCSc1ccccc1-c1nc(NN)c2ncc(C(F)(F)F)cc2n1]

¹H-NMR (CDCl₃) δ: 8.89 (1H, d), 8.46 (1H, d), 8.20 (1H, brs), 8.12 (1H, d), 7.45-7.42 (2H, m), 7.30-7.27 (1H, m), 4.44 (2H, brs), 2.98 (2H, q), 1.33 (3H, t).

Production Example 15 (2)

152 mg of p-toluenesulfonyl chloride was added to a mixture of 246 mg of [2-(2-ethylsulfanylphenyl)-7-trifluoromethylpyrido[3,2-d]pyrimidin-4-yl]-hydrazine, 74 mg of pyridine and 5 ml of acetonitrile, under ice cooling, and the mixture was stirred at room temperature for 15 minutes. A saturated aqueous sodium bicarbonate solution was added to the reaction mixture, and the mixture was extracted with t-butyl methyl ether. The organic layer was washed with water and dried over anhydrous magnesium sulfate, and then concentrated under reduced pressure. The resulting residue was washed with t-butyl methyl ether and n-hexane, and then dried to obtain 156 mg of 1-[2-(2-ethylsulfanylphenyl)-7-trifluoromethylpyrido[3,2-d]pyrimidin-4-yl]-2-tosylhydrazine.

1-[2-(2-Ethylsulfanylphenyl)-7-trifluoromethylpyrido[3,2-d]pyrimidin-4-yl]-2-tosylhydrazine

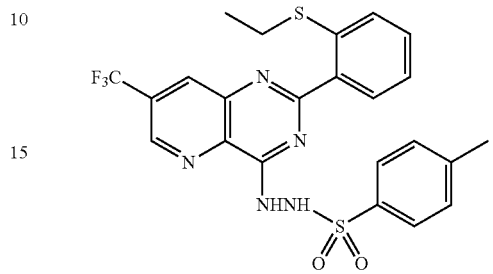

¹H-NMR (CDCl₃) δ: 8.94 (1H, s), 8.78 (1H, brs), 8.43 (1H, s), 7.96 (1H, brs), 7.76 (1H, dd), 7.57 (2H, d) 7.48-7.40 (2H, m), 7.25-7.20 (1H, m), 6.79 (2H, d), 2.99 (2H, q), 2.11 (3H, s), 1.35 (3H, t).

Production Example 15 (3)

A mixture of 156 mg of 1-[2-(2-ethylsulfanylphenyl)-7-trifluoromethylpyrido[3,2-d]pyrimidin-4-yl]-2-tosylhydrazine and 12 ml of ethylene glycol was added to a mixture of 4 ml of an 8% aqueous sodium hydroxide solution and 2 ml of ethylene glycol at 80° C., and the mixture was stirred at 100° C. for 40 minutes. Water was added to the cooled reaction mixture, and the mixture was extracted with t-butyl methyl ether. The organic layer was washed with water, dried over anhydrous magnesium sulfate and concentrated under reduced pressure. The mixture was concentrated under reduced pressure, and the resulting residue was applied to a silica gel column chromatography to obtain 40 mg of 2-(2-ethylsulfanylphenyl)-7-trifluoromethylpyrido[3,2-d]pyrimidine (Compound of Present Invention 18).

Compound of Present Invention 18

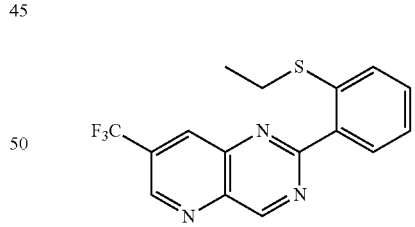

¹H-NMR (CDCl₃) δ: 9.83 (1H, s), 9.24 (1H, d), 8.73 (1H, d), 8.23 (1H, d), 7.51-7.46 (2H, m), 7.36-7.31 (1H, m), 3.00 (2H, q), 1.34 (3H, t).

Production Example 16

60 mg of 3-chloroperbenzoic acid (purity of 65% or more) was added to a mixture of 40 mg of 2-(2-ethylsulfanylphenyl)-7-trifluoromethylpyrido[3,2-d]pyrimidine and 3 ml of chloroform, under ice cooling, and the mixture was stirred at room temperature for 4 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure to obtain 44 mg of 2-(2-ethylsulfonylphenyl)-7-trifluoromethylpyrido[3,2-d]pyrimidine (Compound of Present Invention 19).

Compound of Present Invention 19

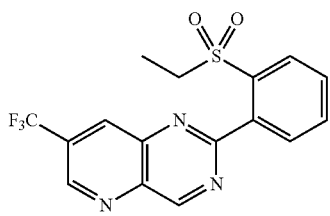 [SMILES: CCS(=O)(=O)c1ccccc1-c1ncc2ncc(C(F)(F)F)cc2n1]

$^1$H-NMR (CDCl$_3$) δ: 9.79 (1H, s), 9.30 (1H, d), 8.64 (1H, d), 8.19 (1H, dd), 7.89 (1H, dd), 7.82 (1H, td), 7.74 (1H, td), 3.82 (2H, q), 1.43 (3H, t).

Production Example 17 (1)

A mixture of 5.22 g of 2-amino-3-bromo-5-trifluoromethylpyridine, 3.80 g of zinc cyanide, 600 mg of tris(dibenzylideneacetone)dipalladium(0), 720 g of 1,1'-bis(diphenylphosphino)ferrocene and 20 ml of DMF was stirred at 120° C. for 30 minutes. Ethyl acetate and water were added to the cooled reaction mixture, and the mixture was filtered. The aqueous layer of the filtrate was extracted with ethyl acetate, then combined with the organic layer of the filtrate and washed with water, and dried over anhydrous magnesium sulfate. The mixture was concentrated under reduced pressure, and then the resulting residue was applied to a silica gel column chromatography to obtain 3.65 g of 2-amino-3-cyano-5-trifluoromethylpyridinepyridine.

2-Amino-3-cyano-5-trifluoromethylpyridinepyridine

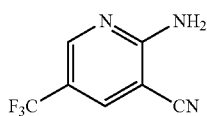

$^1$H-NMR (CDCl$_3$) δ: 8.50 (1H, d), 7.93 (1H, d), 5.60 (2H, brs).

Production Example 17 (2)

15 ml of a 30% aqueous hydrogen peroxide solution was added to a mixture of 3.65 g of 2-amino-3-cyano-5-trifluoromethylpyridinepyridine, 10 ml of a 10% aqueous sodium hydroxide solution and 20 ml of methanol, under ice cooling, and the mixture was stirred at 0° C. for 30 minutes and then stirred at room temperature for 1 hour. Water was added to the reaction mixture, and the precipitated solid was filtered. The resulting solid was washed with water and n-hexane and then dried to obtain 2.59 g of 2-amino-5-trifluoromethylpyridine-3-carboxylic acid amide. The filtrate was extracted with t-butyl methyl ether, and the organic layer was sequentially washed with a 10% aqueous sodium thiosulfate solution, water and a saturated aqueous sodium chloride solution. The resulting matter was dried over anhydrous magnesium sulfate, and then concentrated under reduced pressure to further obtain 800 mg of 2-amino-5-trifluoromethylpyridine-3-carboxylic acid amide.

2-Amino-5-trifluoromethylpyridine-3-carboxylic acid amide

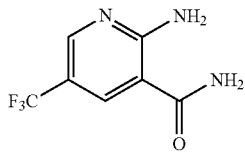 [SMILES: NC(=O)c1cc(C(F)(F)F)cnc1N]

$^1$H-NMR (CDCl$_3$) δ: 8.43 (1H, d), 7.82 (1H, d), 6.86 (2H, brs).

Production Example 17 (3)

A mixture of 1.0 g of 2-amino-5-trifluoromethylpyridine-3-carboxylic acid amide, 810 mg of 2-ethylsulfanylbenzaldehyde, 1.01 g of sodium bisulfite and 3 ml of DMA was stirred at 150° C. for 12 hours. Water was added to the cooled reaction mixture, and the mixture was extracted with ethyl acetate. The organic layer was washed with water, then dried over anhydrous magnesium sulfate, and concentrated under reduced pressure. The resulting residue was applied to a silica gel column chromatography to obtain 975 mg of 2-(2-ethylsulfanylphenyl)-6-trifluoromethyl-3H-pyrido[2,3-d]pyrimidin-4-one.

2-(2-Ethylsulfanylphenyl)-6-trifluoromethyl-3H-pyrido[2,3-d]pyrimidin-4-one

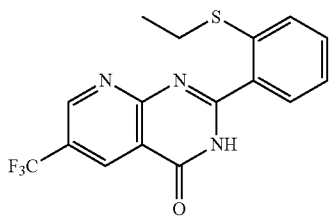 [SMILES: CCSc1ccccc1-c1nc2ncc(C(F)(F)F)cc2c(=O)[nH]1]

$^1$H-NMR (CDCl$_3$) δ: 11.14 (1H, brs), 9.23 (1H, d), 8.90 (1H, d), 8.27 (1H, dd), 7.60 (1H, dd), 7.53 (1H, td), 7.46 (1H, td), 2.93 (2H, q), 1.29 (3H, t).

Production Example 17 (3)

A mixture of 970 mg of 2-(2-ethylsulfanylphenyl)-6-trifluoromethyl-3H-pyrido[2,3-d]pyrimidin-4-one, 0.39 ml of phosphorus oxychloride, 428 mg of N,N-diisopropylethylamine and 20 ml of toluene was stirred at 100° C. for 5 hours. A saturated aqueous sodium bicarbonate solution was added to the cooled reaction mixture, and the mixture was extracted with t-butyl methyl ether. The organic layer was washed with water and dried over anhydrous magnesium sulfate, and then concentrated under reduced pressure to obtain 996 mg of 4-chloro-2-(2-ethylsulfanylphenyl)-6-trifluoromethylpyrido[2,3-d]pyrimidine (Compound of Present Invention 22).

Compound of Present Invention 22

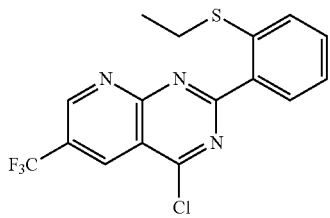 [SMILES: CCSc1ccccc1-c1nc(Cl)c2cc(C(F)(F)F)cnc2n1]

$^1$H-NMR (CDCl$_3$) δ: 9.49 (1H, s), 8.89 (1H, s), 8.39 (1H, d), 7.52-7.45 (2H, m), 7.34-7.29 (1H, m), 3.02 (2H, q), 1.36 (3H, t).

Production Example 18 (1)

180 mg of a 60% sodium hydride (oil-based) and 240 µl of methyl iodide were sequentially added to a mixture of 1.0 g of 2-amino-5-iodo-3-nitropyridine and 20 ml of DMF, under ice cooling. The mixture was heated to room temperature and then stirred for 1 hour. Water was added to the reaction mixture, and the precipitated solid was filtered and then dried.

The resulting solid was dissolved in THF, and this solution was added dropwise to a separately prepared mixture of 633 mg of iron powder, 1 ml of acetic acid, 30 ml of ethanol and 20 ml of water, at 70° C. This mixture was heated and stirred at 70° C. for 3.5 hours. The cooled reaction mixture was filtered. The resulting filtrate was concentrated under reduced pressure. The resulting residue was applied to a silica gel column chromatography to obtain 980 mg of 5-iodo-N$^2$-methylpyridine-2,3-diamine.

5-Iodo-N$^2$-methylpyridine-2,3-diamine

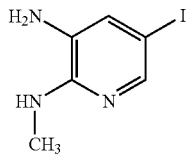

$^1$H-NMR (CDCl$_3$) δ: 7.93 (1H, d), 7.09 (1H, d), 4.16 (1H, brs), 3.19 (2H, brs), 3.00-2.96 (3H, m).

Production Example 18 (2)

A mixture of 0.50 g of 5-iodo-N$^2$-methylpyridine-2,3-diamine and 6 ml of trifluoroacetic acid was stirred at room temperature for 1 hour, and then stirred under heat-reflux for 9 hours. The cooled reaction mixture was concentrated under reduced pressure, then water was added, and the mixture was extracted with ethyl acetate. The organic layer was washed with water, then dried over anhydrous sodium sulfate and concentrated under reduced pressure. The resulting residue was applied to a silica gel column chromatography to obtain 0.57 g of 6-iodo-3-methyl-2-trifluoromethyl-3H-imidazo[4,5-b]pyridine 6-Iodo-3-methyl-2-trifluoromethyl-3H-imidazo[4,5-b]pyridine

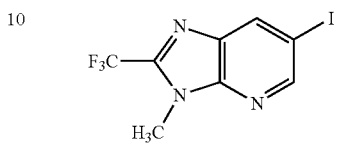

$^1$H-NMR (CDCl$_3$) δ: 8.72 (1H, d), 8.49 (1H, d), 4.02 (3H, s).

Production Example 18 (3)

A mixture of 0.37 g of 2-ethylsulfanylphenylboronic acid pinacol ester, 0.46 g of 6-iodo-3-methyl-2-trifluoromethyl-3H-imidazo[4,5-b]pyridine, 0.03 g of tris(dibenzylideneacetone)dipalladium(0), 0.08 g of 2-dicyclohexylphosphino-2',4',6'-triisopropylphenyl, 0.74 g of tripotassium phosphate, 0.1 ml of water and 10 ml of 1,4-dioxane was stirred at 100° C. for 4 hours. Ethyl acetate and water were added to the cooled reaction mixture, and the mixture was filtered. The filtrate was extracted with ethyl acetate and then dried over anhydrous sodium sulfate. The mixture was concentrated under reduced pressure, and the resulting residue was applied to a silica gel column chromatography to obtain 0.49 g of 6-(2-ethylsulfanylphenyl)-3-methyl-2-trifluoromethyl-3H-imidazo[4,5-b]pyridine (Compound of Present Invention 24).

Compound of Present Invention 24

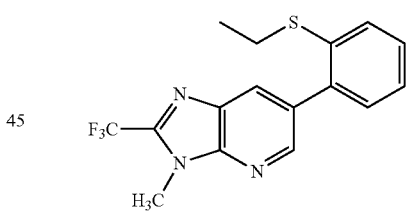

$^1$H-NMR (CDCl$_3$) δ: 8.60 (1H, d), 8.22 (1H, d), 7.47-7.35 (2H, m), 7.30-7.27 (2H, m), 4.10-4.06 (3H, m), 2.82 (2H, q), 1.22 (3H, t).

Production Example 19

0.70 g of 3-chloroperbenzoic acid (purity of 65% or more) was added to a mixture of 0.35 g of 6-(2-ethylsulfanylphenyl)-3-methyl-2-trifluoromethyl-3H-imidazo[4,5-b]pyridine and 10 ml of chloroform under ice cooling, and then the mixture was stirred at room temperature for 4 hours. A 10% aqueous sodium thiosulfate solution and a saturated aqueous sodium bicarbonate solution were added to the reaction mixture, and the mixture was extracted with ethyl acetate and then dried with anhydrous sodium sulfate. The mixture was concentrated under reduced pressure, and the resulting residue was applied to a silica gel column chromatography to obtain 0.31 g of 6-(2-ethylsulfonylphenyl)-3-methyl-2-trifluoromethyl-3H-imidazo[4,5-b]pyridine (Compound of Present Invention 25).

Compound of Present Invention 25

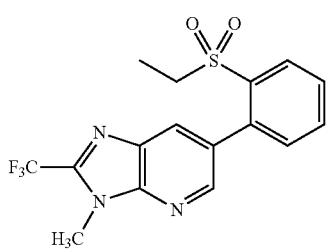 [SMILES: CCS(=O)(=O)c1ccccc1-c1cnc2c(c1)nc(C(F)(F)F)n2C]

¹H-NMR (CDCl₃) δ: 8.60 (1H, d), 8.23 (1H, dd), 8.18 (1H, d), 7.73 (1H, td), 7.67 (1H, td), 7.40 (1H, dd), 4.10 (3H, s), 2.72 (2H, q), 1.09 (3H, t).

Production Example 20

A mixture of 0.53 g of 2-ethylsulfanylphenylboronic acid pinacol ester, 0.52 g of 6-bromo-2-trifluoromethylimidazo[1,2-a]pyridine, 0.02 g of tris(dibenzylideneacetone)dipalladium(0), 0.05 g of 2-dicyclohexylphosphino-2',6'-dimethoxyphenyl, 0.84 g of tripotassium phosphate and 6 ml of 1,4-dioxane was stirred at 110° C. for 7 hours. Ethyl acetate and water were added to the cooled reaction mixture, and the mixture was filtered. The filtrate was extracted with ethyl acetate and then dried over anhydrous sodium sulfate. The mixture was concentrated under reduced pressure, and the resulting residue was applied to a silica gel column chromatography to obtain 0.28 g of 6-(2-ethylsulfanylphenyl)-2-trifluoromethylimidazo[1,2-a]pyridine (Compound of Present Invention 26).

Compound of Present Invention 26

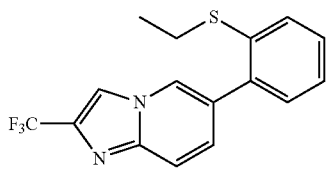 [SMILES: CCSc1ccccc1-c1ccc2nc(C(F)(F)F)cn2c1]

¹H-NMR (CDCl₃) δ: 8.16 (1H, s), 7.91 (1H, s), 7.70 (1H, d), 7.43-7.37 (3H, m), 7.28-7.24 (2H, m), 2.87 (2H, q), 1.27 (3H, t).

Production Example 21

220 mg of 3-chloroperbenzoic acid (purity of 65% or more) was added to a mixture of 134 mg of 6-(2-ethylsulfanylphenyl)-2-trifluoromethylimidazo[1,2-a]pyridine and 4 ml of chloroform, under ice cooling, and the mixture was stirred at room temperature for 4 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure. 93 mg of 6-(2-ethylsulfonylphenyl)-2-trifluoromethylimidazo[1,2-a]pyridine (Compound of Present Invention 27) was obtained.

Compound of Present Invention 27

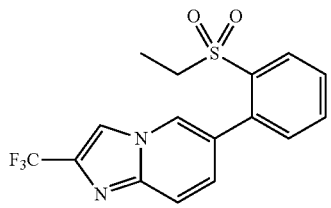 [SMILES: CCS(=O)(=O)c1ccccc1-c1ccc2nc(C(F)(F)F)cn2c1]

¹H-NMR (CDCl₃) δ: 8.39-8.37 (1H, m), 8.25 (1H, dd), 7.95 (1H, s), 7.77-7.71 (2H, m), 7.67 (1H, td), 7.44 (1H, dd), 7.31 (1H, dd), 2.77 (2H, q), 1.11 (3H, t).

Production Example 22 (1)

A mixture of 1.91 g of 3-bromo-1,1,1-trifluoropropan-2-one and 10 ml of DME was added to a mixture of 1.87 g of 2-amino-5-bromo-6-methylpyridine and 10 ml of DME, and the mixture was stirred at room temperature for 3 hours. The precipitated solid was taken by filtration, washed with 10 ml of DME, and dried to obtain 3.39 g of 6-bromo-5-methyl-2-trifluoromethyl-2,3-dihydroimidazo[1,2-a]pyridin-2-ol hydrobromide.

6-Bromo-5-methyl-2-trifluoromethyl-2,3-dihydroimidazo[1,2-a]pyridin-2-ol hydrobromide

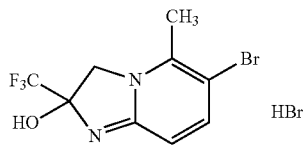

¹H-NMR (DMSO-D₆) δ: 11.02 (1H, s), 8.66 (1H, s), 8.33 (1H, d), 7.01 (1H, d), 5.13 (1H, d), 4.92 (1H, d), 2.66 (3H, s).

Production Example 22 (2)

A mixture of 3.29 g of 6-bromo-5-methyl-2-trifluoromethyl-2,3-dihydroimidazo[1,2-a]pyridin-2-ol hydrobromide and 10 ml of ethanol was stirred under heat-reflux for 3 hours. The cooled reaction mixture was concentrated under reduced pressure, then water was added, and the mixture was extracted with ethyl acetate. The mixture was dried over anhydrous sodium sulfate and concentrated under reduced pressure to obtain 2.72 g of 6-bromo-5-methyl-2-trifluoromethylimidazo[1,2-a]pyridine.

6-Bromo-5-methyl-2-trifluoromethylimidazo[1,2-a]pyridine

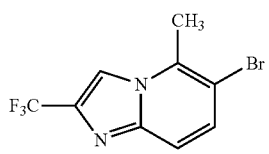

¹H-NMR (CDCl₃) δ: 7.83 (1H, s), 7.52-7.43 (2H, m), 2.78 (3H, s).

Production Example 22 (3)

A mixture of 0.52 g of 2-ethylsulfanylphenylboronic acid pinacol ester, 0.56 g of 6-bromo-5-methyl-2-trifluoromethylimidazo[1,2-a]pyridine, 0.02 g of tris(dibenzylideneacetone)dipalladium(0), 0.05 g of 2-dicyclohexylphosphino-2',4',6'-triisopropylphenyl, 0.84 g of tripotassium phosphate and 6 ml of 1,4-dioxane was stirred under heat-reflux for 3 hours. 0.1 ml of water was added to the cooled reaction mixture, and the mixture was stirred under heat-reflux for 5 hours. Ethyl acetate and water were added to the cooled reaction mixture, and the mixture was filtered. The filtrate was extracted with ethyl acetate and then dried over anhydrous sodium sulfate. The dried matter was concentrated under reduced pressure, and then the resulting residue was applied to a silica gel column chromatography to obtain 0.16 g of 6-(2-ethylsulfanylphenyl)-5-methyl-2-trifluoromethylimidazo [1,2-a]pyridine (Compound of Present Invention 28).

Compound of Present Invention 28

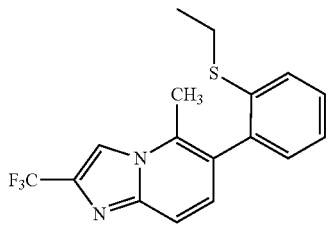 [SMILES: CCSc1ccccc1-c1ccc2nc(C(F)(F)F)cn2c1C]

$^1$H-NMR (CDCl$_3$) δ: 7.86 (1H, s), 7.63 (1H, d), 7.44-7.34 (2H, m), 7.25-7.14 (3H, m), 2.86 (2H, q), 2.40 (3H, s), 1.26 (3H, t).

Production Example 23 (1)

A mixture of 2.4 g of 1-bromo-3,3,4,4,4-pentafluorobutan-2-one and 5 ml of DME was added to a mixture of 1.87 g of 2-amino-5-bromo-6-methylpyridine and 10 ml of DME, and the mixture was stirred at room temperature for 3 hours. The precipitated solid was filtered, and washed with 10 ml of DME to obtain 3.95 g of 6-bromo-5-methyl-2-pentafluoroethyl-2,3-dihydroimidazo[1,2-a]pyridin-2-ol hydrobromide.

6-Bromo-5-methyl-2-pentafluoroethyl-2,3-dihydroimidazo[1,2-a]pyridin-2-ol hydrobromide

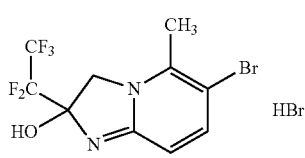

$^1$H-NMR (DMSO-D$_6$) δ: 10.86 (1H, s), 8.82 (1H, s), 8.35 (1H, d), 7.04 (1H, d), 5.06 (2H, dd), 2.69 (3H, s).

Production Example 23 (2)

A mixture of 3.95 g of 6-bromo-5-methyl-2-pentafluoroethyl-2,3-dihydroimidazo[1,2-a]pyridin-2-ol hydrobromide and 20 ml of ethanol was stirred under heat-reflux for 1 day. The cooled reaction mixture was concentrated under reduced pressure, then water and a saturated aqueous sodium bicarbonate solution were added, and the precipitated solid was taken by filtration. The resulting solid was dried to obtain 2.92 g of 6-bromo-5-methyl-2-pentafluoroethylimidazo[1,2-a]pyridine.

6-Bromo-5-methyl-2-pentafluoroethylimidazo[1,2-a]pyridine

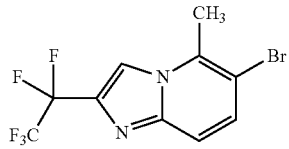

$^1$H-NMR (CDCl$_3$) δ: 7.85 (1H, s), 7.52 (1H, d), 7.46 (1H, d), 2.79 (3H, s).

Production Example 23 (3)

A mixture of 0.53 g of 2-ethylsulfanylphenylboronic acid pinacol ester, 0.65 g of 6-bromo-5-methyl-2-pentafluoroethylimidazo[1,2-a]pyridine, 0.02 g of tris(dibenzylideneacetone)dipalladium(0), 0.05 g of 2-dicyclohexylphosphino-2',4',6'-triisopropylphenyl, 1.0 g of tripotassium phosphate and 3 ml of 1,4-dioxane was stirred under heat-reflux for 9 hours. Ethyl acetate and water were added to the cooled reaction mixture, and the mixture was filtered. The filtrate was extracted with ethyl acetate and then dried over anhydrous sodium sulfate. The dried matter was concentrated under reduced pressure, and then the resulting residue was applied to a silica gel column chromatography to obtain 0.79 g of 6-(2-ethylsulfanylphenyl)-5-methyl-2-pentafluoroethylimidazo[1,2-a]pyridine (Compound of Present Invention 29).

Compound of Present Invention 29

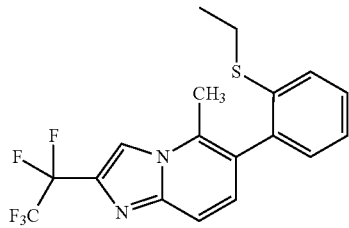 [SMILES: CCSc1ccccc1-c1ccc2nc(C(F)(F)C(F)(F)F)cn2c1C]

$^1$H-NMR (CDCl$_3$) δ: 7.87 (1H, d), 7.66 (1H, d), 7.43-7.35 (2H, m), 7.25-7.20 (2H, m), 7.18-7.14 (1H, m), 2.86 (2H, q), 2.42 (3H, s), 1.26 (3H, t).

Production Example 24

0.51 g of 3-chloroperbenzoic acid (purity of 65% or more) was added to a mixture of 0.59 g of 6-(2-ethylsulfanylphenyl)-5-methyl-2-pentafluoroethylimidazo[1,2-a]pyridine and 5 ml of chloroform under ice cooling, and then the mixture was stirred at room temperature for 2 hours. A 10% aqueous sodium thiosulfate solution and a saturated aqueous sodium bicarbonate solution were added to the reaction mixture, and the mixture was extracted with ethyl acetate and then dried with anhydrous sodium sulfate. The mixture was concentrated under reduced pressure, and then the resulting residue was applied to a silica gel column chromatography to obtain 0.19 g of 6-(2-ethylsulfinyphenyl)-5-methyl-2-pentafluoroethylimidazo[1,2-a]pyridine (Compound of Present Invention 30) and 0.38 g of 6-(2-ethylsulfonyphenyl)-5-methyl-2-pentafluoroethyl-imidazo[1,2-a]pyridine (Compound of Present Invention 31).

Compound of Present Invention 30

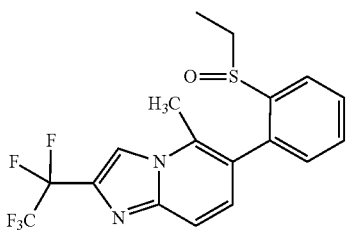 [SMILES: CCS(=O)c1ccccc1-c1ccc2nc(C(F)(F)C(F)(F)F)cn2c1C]

¹H-NMR (CDCl₃) δ: 8.11 (1H, dd), 7.93-7.87 (1H, m), 7.75-7.67 (2H, m), 7.65-7.58 (1H, m), 7.30-7.25 (1H, m), 7.16-7.08 (1H, m), 2.65 (1H, m), 2.52-2.46 (3H, m), 2.42 (1H, m), 1.05 (3H, t).

Compound of Present Invention 31

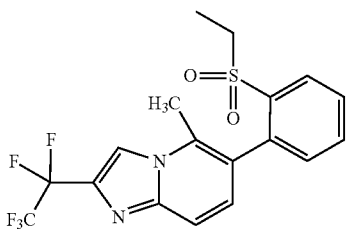 [SMILES: CCS(=O)(=O)c1ccccc1-c1ccc2nc(C(F)(F)C(F)(F)F)cn2c1C]

¹H-NMR (CDCl₃) δ: 8.24 (1H, dd), 7.89 (1H, d), 7.77-7.65 (3H, m), 7.37-7.33 (1H, m), 7.17 (1H, d), 2.91-2.78 (2H, m), 2.40 (3H, s), 1.16 (3H, t).

Production Example 25 (1)

A mixture of 700 mg of 3-amino-6-chloropyridazine, 1.42 g of 2-ethylsulfanylphenylboronic acid pinacol ester, 148 mg of tris(dibenzylideneacetone)dipalladium(0), 603 mg of tricyclohexylphosphine (18% toluene solution), 3.43 g of tripotassium phosphate, 4.5 ml of 1,4-dioxane and 1.5 ml of water was stirred at 100° C. for 3 hours. Water was added to the cooled reaction mixture, and the mixture was extracted with ethyl acetate. The organic layer was washed with water, then dried over anhydrous magnesium sulfate, and concentrated under reduced pressure. The resulting residue was applied to a silica gel column chromatography to obtain 927 mg of 3-amino-6-(2-ethylsulfanylphenyl)pyridazine.

3-Amino-6-(2-ethylsulfanylphenyl)pyridazine

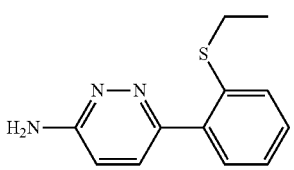 [SMILES: CCSc1ccccc1-c1ccc(N)nn1]

¹H-NMR (CDCl₃) δ: 7.57 (1H, d), 7.53 (1H, dd), 7.46 (1H, dd), 7.36 (1H, td), 7.30 (1H, td), 6.79 (1H, d), 4.80 (2H, brs), 2.79 (2H, q), 1.20 (3H, t).

Production Example 25 (2)

783 mg of 3-bromo-1,1,1-trifluoropropan-2-one was added to a mixture of 789 mg of 3-amino-6-(2-ethylsulfanylphenyl)pyridazine, 566 mg of potassium carbonate and 3.5 ml of ethanol, and the mixture was stirred at 60° C. for 1 hour. Water was added to the cooled reaction mixture, and the precipitated solid was taken by filtration. The resulting solid was washed with water and n-hexane and then dried to obtain 860 mg of 6-(2-ethylsulfanylphenyl)-2-trifluoromethyl-2,3-dihydroimidazo[1,2-b]pyridin-2-ol.

6-(2-Ethylsulfanylphenyl)-2-trifluoromethyl-2,3-dihydroimidazo[1,2-b]pyridin-2-ol

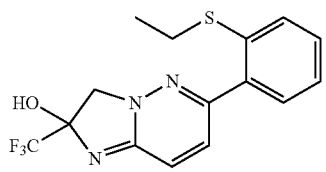 [SMILES: CCSc1ccccc1C1=NN2CC(O)(C(F)(F)F)N=C2C=C1]

¹H-NMR (CDCl₃) δ: 7.46-7.27 (5H, m), 6.98 (1H, d), 4.42 (1H, d), 4.33 (1H, d), 2.90 (2H, q), 1.28 (3H, t).

Production Example 25 (3)

A mixture of 860 mg of 6-(2-ethylsulfanylphenyl)-2-trifluoromethyl-2,3-dihydroimidazo[1,2-b]pyridin-2-ol and 3 ml of DMF was refluxed for 5 hours. Water was added to the cooled reaction mixture, and the mixture was extracted with t-butyl methyl ether. The organic layer was washed with water and dried over anhydrous magnesium sulfate, and then concentrated under reduced pressure. The resulting residue was applied to a silica gel column chromatography to obtain 615 mg of 6-(2-ethylsulfanylphenyl)-2-trifluoromethylimidazo[1,2-b]pyridine (Compound of Present Invention 33).

Compound of Present Invention 33

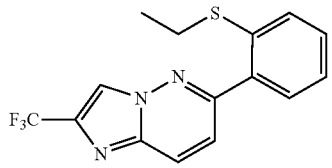 [SMILES: CCSc1ccccc1-c1ccc2nc(C(F)(F)F)cn2n1]

¹H-NMR (CDCl₃) δ: 8.28 (1H, s), 8.02 (1H, d), 7.53-7.42 (4H, m), 7.37-7.31 (1H, m), 2.88 (2H, q), 1.25 (3H, t).

Production Example 26

646 mg of 3-chloroperbenzoic acid (purity of 65% or more) was added to a mixture of 395 mg of 6-(2-ethylsulfanylphenyl)-2-trifluoromethylimidazo[1,2-b]pyridine and 8 ml of chloroform, under ice cooling, and the mixture was stirred at room temperature for 4 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure to obtain 410 mg of 6-(2-ethylsulfonylphenyl)-2-trifluoromethylimidazo[1,2-b]pyridine (Compound of Present Invention 34).

Compound of Present Invention 34

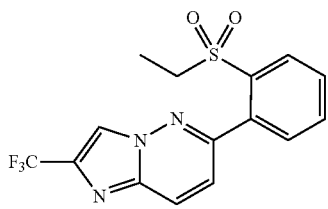

$^1$H-NMR (CDCl$_3$) δ: 8.21 (1H, s), 8.18 (1H, dd), 8.07 (1H, d), 7.80 (1H, td), 7.75 (1H, td), 7.52 (1H, dd), 7.31 (1H, d), 3.33 (2H, q), 1.31 (3H, t).

Production Example 27 (1)

A mixture of 1.91 g of 3-bromo-1,1,1-trifluoropropan-2-one and 5 ml of DME was added to a mixture of 1.74 g of 2-amino-5-bromopyrimidine and 15 ml of DME, and the mixture was stirred at room temperature for 1 day. The precipitated solid was taken by filtration, washed with 10 ml of DME, and dried to obtain 1.02 g of 6-bromo-2-trifluoromethyl-2,3-dihydroimidazo[1,2-a]pyrimidin-2-ol hydrobromide.

A mixture of 0.97 g of resulting 6-bromo-2-trifluoromethyl-2,3-dihydroimidazo[1,2-a]pyrimidin-2-ol hydrobromide and 10 ml of ethanol was stirred under heat-reflux for 5 hours. The cooled reaction mixture was concentrated under reduced pressure, then water was added, and the mixture was extracted with ethyl acetate. The resulting matter was dried over anhydrous sodium sulfate and concentrated under reduced pressure. The resulting residue was applied to a silica gel column chromatography to obtain 0.54 g of 6-bromo-2-trifluoromethyl-imidazo[1,2-a]pyrimidine.

6-Bromo-2-trifluoromethylimidazo[1,2-a]pyrimidine

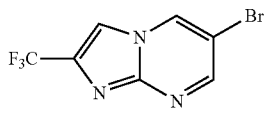

$^1$H-NMR (CDCl$_3$) δ: 8.68 (1H, d), 8.63 (1H, d), 7.84 (1H, d).

Production Example 27 (2)

A mixture of 0.52 g of 2-ethylsulfanylphenylboronic acid pinacol ester, 0.44 g of 6-bromo-2-trifluoromethylimidazo[1,2-a]pyrimidine, 0.02 g of tris(dibenzylideneacetone)dipalladium(0), 0.05 g of 2-dicyclohexylphosphino-2',4',6'-triisopropylphenyl, 1.0 g of tripotassium phosphate and 6 ml of 1,4-dioxane was stirred under heat-reflux for 4 hours. Ethyl acetate and water were added to the cooled reaction mixture, and the mixture was filtered. The filtrate was extracted with ethyl acetate and then dried over anhydrous sodium sulfate. The mixture was concentrated under reduced pressure, and the resulting residue was applied to a silica gel column chromatography to obtain 0.20 g of 6-(2-ethylsulfanylphenyl)-2-trifluoromethylimidazo[1,2-a]pyrimidine (Compound of Present Invention 35).

Compound of Present Invention 35

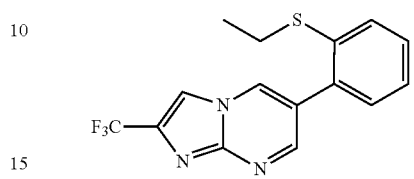

$^1$H-NMR (CDCl$_3$) δ: 8.76 (1H, d), 8.48 (1H, d), 7.88 (1H, d), 7.50-7.43 (2H, m), 7.35-7.29 (2H, m), 2.89 (2H, q), 1.27 (3H, t).

Production Example 28

252 mg of 3-chloroperbenzoic acid (purity of 65% or more) was added to a mixture of 154 mg of 6-(2-ethylsulfanylphenyl)-2-trifluoromethylimidazo[1,2-a]pyrimidine and 4 ml of chloroform, under ice cooling, and the mixture was stirred at room temperature for 4 hours. A 10% aqueous sodium thiosulfate solution was added to the reaction mixture, and the mixture was extracted with chloroform. The organic layer was washed with a saturated aqueous sodium bicarbonate solution and dried over anhydrous magnesium sulfate, and then concentrated under reduced pressure. 80 mg of 6-(2-ethylsulfonylphenyl)-2-trifluoromethylimidazo[1,2-a]pyrimidine (Compound of Present Invention 36) was obtained.

Compound of Present Invention 36

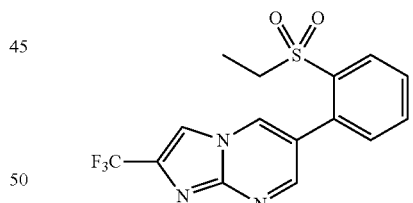

$^1$H-NMR (CDCl$_3$) δ: 8.74 (1H, d), 8.64 (1H, d), 8.26 (1H, dd), 7.92 (1H, s), 7.80 (1H, td), 7.74 (1H, td), 7.47 (1H, dd), 2.80 (2H, q), 1.14 (3H, t).

Production Example 29 (1)

A mixture of 1.14 g of 3-bromo-1,1,1-trifluoropropan-2-one and 10 ml of DME was added to a mixture of 1.04 g of 2-amino-4-bromopyrimidine and 10 ml of DME, and the mixture was stirred at room temperature for 1 day. The precipitated solid was taken by filtration, washed with 10 ml of DME, and dried to obtain 1.92 g of 7-bromo-2-trifluoromethyl-2,3-dihydroimidazo[1,2-a]pyridin-2-ol hydrobromide.

7-Bromo-2-trifluoromethyl-2,3-dihydroimidazo[1,2-a]pyridin-2-ol hydrobromide

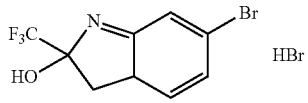

$^1$H-NMR (DMSO-D$_6$) δ: 11.14 (1H, s), 8.71 (1H, s), 8.33-8.27 (1H, m), 7.51-7.46 (2H, m), 5.03 (1H, d), 4.78 (1H, d).

Production Example 29 (2)

A mixture of 1.82 g of 7-bromo-2-trifluoromethyl-2,3-dihydroimidazo[1,2-a]pyridin-2-ol hydrobromide and 10 ml of ethanol was stirred under heat-reflux for 1 day. The cooled reaction mixture was concentrated under reduced pressure, then water was added, and the mixture was extracted with ethyl acetate. The mixture was dried over anhydrous sodium sulfate and concentrated under reduced pressure to obtain 1.33 g of 7-bromo-2-trifluoromethylimidazo[1,2-a]pyridine.

7-Bromo-2-trifluoromethylimidazo[1,2-a]pyridine

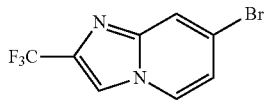

$^1$H-NMR (CDCl$_3$) δ: 8.02 (1H, d), 7.90-7.86 (2H, m), 7.03 (1H, dd).

Production Example 29 (3)

A mixture of 0.53 g of 2-ethylsulfanylphenylboronic acid pinacol ester, 0.52 g of 7-bromo-2-trifluoromethylimidazo[1,2-a]pyridine, 0.02 g of tris(dibenzylideneacetone)dipalladium(0), 0.05 g of 2-dicyclohexylphosphino-2',4',6'-triisopropylphenyl, 1.0 g of tripotassium phosphate and 6 ml of 1,4-dioxane was stirred under heat-reflux for 6 hours. Ethyl acetate and water were added to the cooled reaction mixture, and the mixture was filtered. The filtrate was extracted with ethyl acetate and then dried over anhydrous sodium sulfate. The mixture was concentrated under reduced pressure, and the resulting residue was applied to a silica gel column chromatography to obtain 0.40 g of 7-(2-ethylsulfanylphenyl)-2-trifluoromethylimidazo[1,2-a]pyridine (Compound of Present Invention 37).

Compound of Present Invention 37

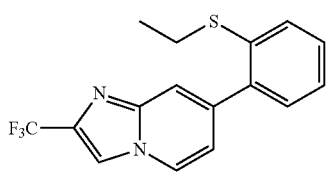 [SMILES: CCSc1ccccc1-c1ccn2cc(C(F)(F)F)nc2c1]

$^1$H-NMR (CDCl$_3$) δ: 8.15 (1H, dd), 7.91 (1H, s), 7.68 (1H, s), 7.43 (1H, d), 7.41-7.35 (1H, m), 7.30-7.27 (2H, m), 7.08 (1H, dd), 2.84 (2H, q), 1.24 (3H, t).

The compounds described in the production examples described above and the compounds produced by the production method according to the method described in the production examples described above are shown in the tables.

Compounds represented by the formula (1-1):

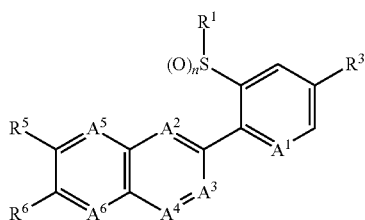

(1-1)

wherein $R^1$, $R^3$, $R^5$, $R^6$, $A^1$, $A^2$, $A^3$, $A^4$, $A^5$, $A^6$ and n represent the combinations shown in [Table 17] shown below.

TABLE 17

| Compound of Present Invention | $R^1$ | $R^3$ | $R^5$ | $R^6$ | $A^1$ | $A^2$ | $A^3$ | $A^4$ | $A^5$ | $A^6$ | n |
|---|---|---|---|---|---|---|---|---|---|---|---|
| 1 | Et | H | H | CF$_3$ | CH | N | CH | N | CH | CH | 0 |
| 2 | Et | H | H | CF$_3$ | CH | N | CMe | N | CH | CH | 0 |
| 3 | Et | H | CF$_3$ | H | CH | N | N | CBr | CH | CH | 0 |
| 4 | Et | H | CF$_3$ | H | CH | N | N | CCl | CH | CH | 0 |
| 5 | Et | H | CF$_3$ | H | CH | N | N | CNH$_2$ | CH | CH | 0 |
| 6 | Et | H | CF$_3$ | H | CH | N | N | CNHMe | CH | CH | 0 |
| 7 | Et | H | CF$_3$ | H | CH | N | N | CNHEt | CH | CH | 0 |
| 8 | Et | H | CF$_3$ | H | CH | N | N | CNHPr | CH | CH | 0 |
| 9 | Et | H | CF$_3$ | H | CH | N | N | CNHPr | CH | CH | 1 |
| 10 | Et | H | CF$_3$ | H | CH | N | N | CNHPr | CH | CH | 2 |
| 11 | Et | H | CF$_3$ | H | CH | N | N | CH | CH | CH | 0 |
| 12 | Et | H | CF$_3$ | H | CH | N | N | CH | CH | CH | 2 |
| 13 | Et | H | CF$_3$ | H | CH | N | N | CMe | CH | CH | 0 |
| 14 | Et | Cl | CF$_3$ | H | CH | N | N | CCl | CH | CH | 0 |
| 15 | Et | Cl | CF$_3$ | H | CH | N | CH | CNHPr | CH | CH | 0 |
| 16 | Et | Cl | CF$_3$ | H | CH | N | CH | CNHPr | CH | CH | 2 |
| 17 | Et | H | CF$_3$ | H | CH | N | N | CCl | CH | N | 0 |
| 18 | Et | H | CF$_3$ | H | CH | N | N | CH | CH | N | 0 |
| 19 | Et | H | CF$_3$ | H | CH | N | N | CH | CH | N | 2 |
| 20 | Et | H | CF$_3$ | H | CH | N | N | CMe | CH | N | 0 |
| 21 | Et | H | CF$_3$ | H | CH | N | N | CMe | CH | N | 2 |
| 22 | Et | H | H | CF$_3$ | CH | N | N | CCl | N | CH | 2 |
| 23 | Et | H | H | CF$_3$ | CH | N | N | CNH$_2$ | N | CH | 2 |

Compounds represented by the formula (1-2):

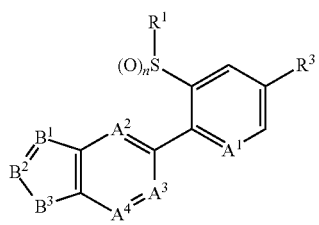

(1-2)

wherein $R^1$, $R^3$, $A^1$, $A^2$, $A^3$, $A^4$, $B^1$, $B^2$, $B^3$ and n represent the combinations shown in [Table 18] shown below.

TABLE 18

| Compound of Present Invention | $R^1$ | $R^3$ | $A^1$ | $A^2$ | $A^3$ | $A^4$ | $B^1$ | $B^2$ | $B^3$ | n |
|---|---|---|---|---|---|---|---|---|---|---|
| 24 | Et | H | CH | CH | CH | N | N | CCF$_3$ | NMe | 0 |
| 25 | Et | H | CH | CH | CH | N | N | CCF$_3$ | NMe | 2 |

Compounds represented by the formula (1-3):

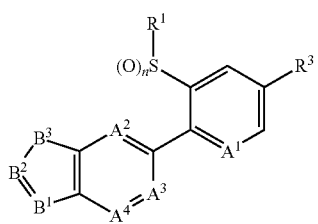

(1-3)

wherein $R^1$, $R^3$, $A^1$, $A^2$, $A^3$, $A^4$, $B^1$, $B^2$, $B^3$ and n represent the combinations shown in [Table 19] shown below.

TABLE 19

| Compound of Present Invention | $R^1$ | $R^3$ | $A^1$ | $A^2$ | $A^3$ | $A^4$ | $B^1$ | $B^2$ | $B^3$ | n |
|---|---|---|---|---|---|---|---|---|---|---|
| 39 | Et | H | CH | N | CH | CN | N | CCF$_3$ | NMe | 0 |
| 40 | Et | H | CH | N | CH | CN | N | CCF$_3$ | NMe | 2 |

Compounds represented by the formula (1-4):

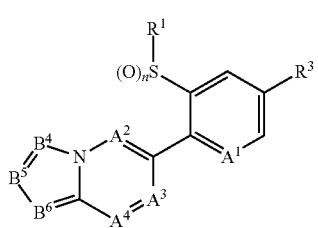

(1-4)

wherein $R^1$, $R^3$, $A^1$, $A^2$, $A^3$, $A^4$, $B^4$, $B^5$, $B^6$ and n represent the combinations shown in [Table 20] shown below.

TABLE 20

| Compound of Present Invention | $R^1$ | $R^3$ | $A^1$ | $A^2$ | $A^3$ | $A^4$ | $B^4$ | $B^5$ | $B^6$ | n |
|---|---|---|---|---|---|---|---|---|---|---|
| 26 | Et | H | CH | CH | CH | CH | CH | CCF$_3$ | N | 0 |
| 27 | Et | H | CH | CH | CH | CH | CH | CCF$_3$ | N | 2 |
| 28 | Et | H | CH | CMe | CH | CH | CH | CCF$_3$ | N | 0 |
| 29 | Et | H | CH | CMe | CH | CH | CH | CCF$_2$CF$_3$ | N | 0 |
| 30 | Et | H | CH | CMe | CH | CH | CH | CCF$_2$CF$_3$ | N | 1 |
| 31 | Et | H | CH | CMe | CH | CH | CH | CCH$_2$CF$_3$ | N | 2 |
| 32 | Et | H | CH | CH | CMe | CH | CH | CCF$_3$ | N | 0 |
| 33 | Et | H | CH | N | CH | CH | CH | CCF$_3$ | N | 0 |
| 34 | Et | H | CH | N | CH | CH | CH | CCF$_3$ | N | 2 |
| 35 | Et | H | CH | CH | CH | N | CH | CCF$_3$ | N | 0 |
| 36 | Et | H | CH | CH | CH | N | CH | CCF$_3$ | N | 2 |

Compounds represented by the formula (1-5):

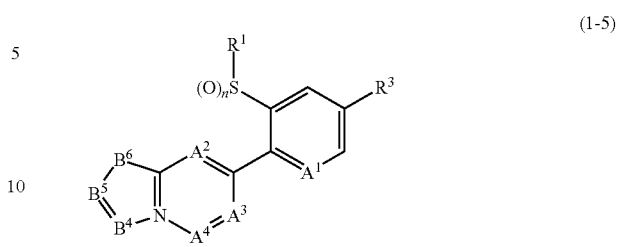

(1-5)

wherein $R^1$, $R^3$, $A^1$, $A^2$, $A^3$, $A^4$, $B^4$, $B^5$, $B^6$ and n represent the combinations shown in [Table 21] shown below.

TABLE 21

| Compound of Present Invention | $R^1$ | $R^3$ | $A^1$ | $A^2$ | $A^3$ | $A^4$ | $B^4$ | $B^5$ | $B^6$ | n |
|---|---|---|---|---|---|---|---|---|---|---|
| 37 | Et | H | CH | CH | CH | CH | CH | CCF$_3$ | N | 0 |
| 38 | Et | H | CH | CH | CH | CH | CH | CCF$_3$ | N | 2 |

(In [Table 17] to [Table 21] above, Me represents a methyl group, Et represents an ethyl group, and Pr represents a propyl group)

$^1$H-NMR data of the compounds of the present invention shown in [Table 17] to [Table 21] are shown below.

Compound of Present Invention 6

$^1$H-NMR (CDCl$_3$) δ: 8.24 (1H, s), 8.11 (1H, dd), 7.81 (1H, d), 7.62 (1H, dd), 7.45-7.36 (2H, m), 7.28-7.23 (1H, m), 5.85 (1H, brs), 3.34 (3H, d), 2.97 (2H, q), 1.32 (3H, t).

Compound of Present Invention 7

$^1$H-NMR (CDCl$_3$) δ: 8.23 (1H, s), 8.09 (1H, dd), 7.82 (1H, d), 7.62 (1H, dd), 7.44-7.36 (2H, m), 7.28-7.23 (1H, m), 5.76 (1H, brs), 3.90-3.83 (2H, m), 2.96 (2H, q), 1.41 (3H, t), 1.31 (3H, t).

Compound of Present Invention 20

$^1$H-NMR (CDCl$_3$) δ: 9.18 (1H, d), 8.67 (1H, d), 8.15 (1H, dd), 7.50-7.43 (2H, m), 7.31 (1H, td), 3.19 (3H, s), 2.99 (2H, q), 1.32 (3H, t).

Compound of Present Invention 21

$^1$H-NMR (CDCl$_3$) δ: 9.23 (1H, d), 8.58 (1H, d), 8.18 (1H, dd), 7.87 (1H, dd), 7.81 (1H, td), 7.71 (1H, td), 3.84 (2H, q), 3.16 (3H, s), 1.43 (3H, t).

Compound of Present Invention 23

$^1$H-NMR (CDCl$_3$) δ: 9.32 (1H, d), 8.44 (1H, d), 8.16 (1H, d), 7.43-7.41 (2H, m), 7.25-7.22 (1H, m), 6.03 (2H, brs), 2.97 (2H, q), 1.32 (3H, t).

Compound of Present Invention 32

$^1$H-NMR (CDCl$_3$) δ: 7.91 (1H, s), 7.81 (1H, s), 7.52 (1H, d), 7.41 (1H, td), 7.34 (1H, d), 7.22 (1H, dd), 7.14 (1H, dd), 2.96-2.81 (2H, m), 2.16-2.13 (3H, m), 1.29 (3H, t).

Next, formulation examples of the compound of the present invention are shown. The part means part by weight.

Formulation Example 1

10 parts of any one of Compounds of Present Invention 1 to 40 are dissolved in a mixture of 35 parts of xylene and 35 parts of DMF, and 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 40 are further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 40. Subsequently, an appropriate amount of water is added to this mixture, and the mixture is further stirred, granulated with a granulator, and forced-air dried to obtain each granule.

Formulation Example 4

1 part of any one of Compounds of Present Invention 1 to 40 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 40 and 55 parts of water are mixed, and finely pulverized by wet grinding method to obtain each flowable.

Formulation Example 6

0.1 parts of any one of Compounds of Present Invention 1 to 40 are dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1 to 40 is dissolved in 0.5 ml of acetone, and this solution is applied to 5 g of solid feed powder for animal (solid feed powder for breeding CE-2, product of CLEA Japan, Inc), and the mixture is uniformly mixed. Subsequently, acetone is evaporated to dryness to obtain each poisonous bait.

Formulation Example 8

0.1 parts of any one of Compounds of Present Invention 1 to 40 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1 to 40, 0.01 parts of BHT (2,6-di-tert-butyl-4-methylphenol), 5 parts of xylene, 3.39 parts of deodorized kerosene and 1 part of emulsifier {RHEODOL MO-60 (trade name of Kao Corporation)} are mixed and dissolved, and the resulting solution and 50 parts of distilled water are filled into an aerosol container. A valve is attached to the container, and then 40 parts of a propellant (LPG) is filled under pressure through the valve to obtain an aqueous aerosol.

Formulation Example 10

0.1 g of any one of Compounds of Present Invention 1 to 40 is dissolved in 2 ml of propylene glycol, and the solution is impregnated in a porous ceramic plate with a size of 4.0 cm×4.0 cm and 1.2 cm in thickness to obtain a heating type smoking agent.

Formulation Example 11

5 parts of any one of Compounds of Present Invention 1 to 40 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 12

5 parts of any one of Compounds of Present Invention 1 to 40 and 95 parts of a soft vinyl chloride resin are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 13

100 mg of any one of Compounds of Present Invention 1 to 40, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture is compressed to an appropriate size to obtain a tablet.

Formulation Example 14

25 mg of any one of Compounds of Present Invention 1 to 40, 60 mg of lactose, 25 mg of corn starch, 6 mg of carmellose calcium and an appropriate amount of 5% hydroxypropyl methylcellulose, and the resulting mixture is filled into a hard shell gelatin capsule or a hydroxypropyl methylcellulose capsule to obtain an encapsulated formulation.

Formulation Example 15

Distilled water is added to 1000 mg of any one of Compounds of Present Invention 1 to 40, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co), 35 mg of flavor and 500 mg of colorant, such that a final volume is 100 ml, and the mixture is mixed to obtain a suspension for oral administration.

Formulation Example 16

5 parts of any one of Compounds of Present Invention 1 to 40 are dissolved in 5 parts of polysorbate 85, 3 parts of benzyl alcohol, and 30 parts of propylene glycol, and a phosphate buffer is added to this solution so as to have a pH of 6.0 to 6.5, and then water is added until a total amount is 100 parts to obtain a liquid formulation for oral administration.

Formulation Example 17

5 parts of aluminum distearate is dispersed in 57 parts of fractionated palm oil and 3 parts of polysorbate 85 by heating, and 25 parts of saccharin is dispersed in an oily vehicle obtained by cooling this dispersion to room temperature. Further, 10 parts of any one of Compounds of Present Invention 1 to 40 are added thereto to obtain a paste formulation for oral administration.

Formulation Example 18

5 parts of any one of Compounds of Present Invention 1 to 40 and 95 parts of limestone filler are mixed, and a granule for oral administration is obtained using wet granulation method.

Formulation Example 19

5 parts of any one of Compounds of Present Invention 1 to 40 are dissolved in 80 parts of diethylene glycol monoethyl ether, and 15 parts of propylene carbonate are mixed therewith to obtain a spot-on solution.

Formulation Example 20

10 parts of any one of Compounds of Present Invention 1 to 40 are dissolved in 70 parts of diethylene glycol monoethyl ether, and 20 parts of 2-octyl dodecanol are mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1 to 40, and the mixture is sufficiently stirred and mixed until it becomes a uniform solution, and then 19.5 parts of water are added and further sufficiently stirred and mixed to obtain a shampoo agent as a uniform solution.

Formulation Example 22

0.15 parts of any one of Compounds of Present Invention 1 to 40, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1 to 40 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention is shown as test examples.

Test Example 1

The formulations of Compounds of Present Invention 24, 25, 28 to 31, 33 and 35 as obtained in Formulation Example 5 were diluted with water, so as to have a concentration of the active ingredient of 500 ppm, to prepare a test drug solution.

On the other hand, on a cucumber seedling (the first true leaf stage) planted in a plastic cup was inoculated with about 30 *Aphis gossypii*, and leaving it for 1 day. 20 ml of the test drug solution was sprayed on the seedling.

Six days after spraying, the number of surviving *Aphis gossypii* parasitized on the leaves of the cucumber was examined, and the controlling value was calculated according to the following equation:

Controlling value (%)=$\{1-(Cb \times Tai)/(Cai \times Tb)\} \times 100$ wherein the symbols represent as follows:
Cb: the number of insects in a non-treated section before treatment,
Cai: the number of insects in a non-treated section on observation,
Tb: the number of insects in a treated section before treatment,
Tai: the number of insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using a test drug solution containing each of Compounds of Present Invention 24, 25, 28 to 31, 33 and 35, the controlling value was 90% or more.

Test Example 2

The formulation of Compound of Present Invention 36 as obtained in Formulation Example 5 was diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated 30 *Aphis gossypii* (whole stage), and further kept in the greenhouse for 6 days, then the number of surviving *Aphis gossypii* parasitized on the leaves of the cucumber was examined, and the controlling value was calculated according to the following equation:

Controlling value (%)=$\{1-(Cb \times Tai)/(Cai \times Tb)\} \times 100$ wherein the symbols represent as follows:
Cb: the number of insects in a non-treated section before treatment,
Cai: the number of insects in a non-treated section on observation,
Tb: the number of insects in a treated section before treatment,
Tai: the number of insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using the test drug solution containing Compound of Present Invention 36, the controlling value was 90% or more.

Test Example 3

The formulations of Compounds of Present Invention 1, 24, 28, 29 and 33 as obtained in Formulation Example 5 were diluted with water, so as to have a concentration of the active ingredient of 500 ppm, to prepare a test drug solution.

On a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of *Nilaparvata lugens* parasitized on the rice was examined, and the controlling value was calculated according to the following equation:

Controlling value (%)={1−(Cb×Tai)/(Cai×Tb)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the test drug solution prepared by diluting the formulation not containing the compound of the present invention as in Formulation Example 5 with the same amount of water as in the treated section was sprayed.

As a result, in the treated section using a test drug solution containing each of Compounds of Present Invention 1, 24, 28, 29 and 33, the controlling value was 90% or more.

Test Example 4

The formulations of Compounds of Present Invention 28 and 34 as obtained in Formulation Example 5 were diluted with water, so as to have a concentration of the active ingredient of 500 ppm, to prepare a test drug solution.

On the other hand, a rice seedling (2 weeks after sowing, the second leaf stage) planted in a plastic cup was drenched at its foot with 5 ml of each test drug solution, and kept in a greenhouse of 25° C. for 7 days. 20 third-fourth instar larvae of *Nilaparvata lugens* were released, and further kept in the greenhouse for 6 days, then the number of surviving *Nilaparvata lugens* parasitized on the rice was examined, and the controlling value was calculated according to the following equation:

Controlling value (%)={1−(Cb×Tai)/(Cai×Tb)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the test drug solution prepared by diluting the formulation not containing the compound of the present invention as in Formulation Example 5 with the same amount of water as in the treated section was sprayed.

As a result, in the treated section using a test drug solution containing each of Compounds of Present Invention 28 and 34, the controlling value was 90% or more.

Test Example 5

The formulation of the compound of the present invention as obtained in Formulation Example 5 is diluted with water, so as to have a concentration of the active ingredient of 500 ppm, to prepare a test drug solution.

On the other hand, *Bemisia tabaci* adult is released on a tomato seedling (the third true leaf stage) planted in a polyethylene cup, and made to lay eggs for about 72 hours. The tomato seedling is kept in a greenhouse for 8 days, and when instar larvae hatches from the eggs, the above test drug solution is sprayed in an amount of 20 ml/cup, and the cup is kept in a greenhouse at 25° C. After 7 days, the number of surviving instar larvae on the tomato leaves is examined, and the controlling value is calculated according to the following equation:

Controlling value (%)={1−(Cb×Tai)/(Cai×Tb)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the test drug solution prepared by diluting the formulation not containing the compound of the present invention as in Formulation Example 5 with the same amount of water as in the treated section was sprayed.

As a result, in the treated section using the test drug solution of the compound of the present invention, a sufficient controlling value is obtained.

Test Example 6

The formulations of Compounds of Present Invention 1, 2, 7, 12, 25, 29 to 31, 33 and 34 as obtained in Formulation Example 5 were diluted with water, so as to have a concentration of the active ingredient of 500 ppm, to prepare a test drug solution.

On the other hand, on cabbage at the third leaf stage planted in a polyethylene cup was sprayed in an amount of 20 mL/cup of the test drug solution. After the drug solution was dried, the foliage part was cut off, and then placed in a 50 mL volume cup. 5 second instar larvae of *Plutella xylostella* were released into the cup, and the cup was sealed with a lid. After the cup was kept at 25° C. for 5 days, the number of surviving insects was counted. The death rate was calculated according to the following equation:

Death rate (%)=(Number of dead insects/Number of tested insects)×100.

As a result, in the treated section using each test drug solution of Compounds of Present Invention 1, 2, 7, 12, 25, 29 to 31, 33 and 34, the death rate was 80% or more.

Test Example 7

The formulations of Compounds of Present Invention 1, 2, 7, 15, 25, 27, 29 to 31, 33 and 34 as obtained in Formulation Example 5 were diluted with water, so as to have a concentration of the active ingredient of 500 ppm, to prepare a test spray solution.

On the other hand, an apple tree was planted in a plastic cup, and grown until the seventh-eighth true leaf was spread.

To the apple tree was sprayed in an amount of 20 mL/cup of the test drug solution. After the drug solution was dried, 60 first-instar *Adoxophyes orana fasciata* were released, and the plastic cup the bottom of which was cut off and on which a filter paper was put was upside-down and covered. After 7 days, the number of surviving insects was counted, and the death rate was calculated according to the following equation:

Death rate (%)=(Number of dead insects/Number of tested insects)×100.

As a result, in the treated section using each test drug solution of Compounds of Present Invention 1, 2, 7, 15, 25, 27, 29 to 31, 33 and 34, the death rate was 90% or more.

Test Example 8

The formulations of Compounds of Present Invention 25 and 35 as obtained in Formulation Example 5 were diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 10 female imagoes of *Musca domestica* were released, and the cup was sealed with a lid. After 24 hours, the life and death of *Musca domestica* was examined, and the death rate was calculated.

As a result, in the treatment with Compounds of Present Invention 25 and 35, the death rate was 100% or more.

Test Example 9

The formulation of Compound of Present Invention as obtained in Formulation Example 5 is diluted with water, so as to have a concentration of the active ingredient of 500 ppm, to prepare a test drug solution.

A filter paper having a diameter of 5.5 cm is spread on the bottom of a polyethylene cup having the same diameter and 0.7 ml of the test drug solution is added dropwise onto the filter paper, and 30 mg of sucrose is uniformly placed as bait. Into the polyethylene cup, 2 male imagoes of *Blattella germanica* are released, and the cup is sealed with a lid. After 6 days, the life and death of *Blattella germanica* is examined, and the death rate is calculated.

As a result, in the treated section using the test drug solution of the compound of the present invention, a sufficient death rate is obtained.

Test Example 10

The formulations of Compounds of Present Invention 1 and 33 as obtained in Formulation Example 5 were diluted with water, so as to have a concentration of the active ingredient of 500 ppm, to prepare a test drug solution.

0.7 ml of the test drug solution was added to 100 ml of ion-exchanged water (active ingredient concentration: 3.5 ppm). 20 last-instar larvae of *Culex pipiens pallens* were released into the solution. One day later, the life and death of the *Culex pipiens pallens* was examined, and the death rate of the pest was calculated.

As a result, in the treatment with Compounds of Present Invention 1 and 33, the death rate was 91% or more.

Test Example 11

2 mg of each of Compounds of Present Invention 6, 8, 10, 26, 28, 29, 33, 35 and 37 was weighed in a screw tube (Maruemu No. 5; 27×55 mm), and 0.2 mL of acetone was added thereto and sealed with a cap to dissolve the compound. The screw tube was rotated and inverted to uniformity coat the drug solution onto the whole inner wall of the tube. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead ticks was examined, and the death rate was calculated according to the following equation:

Death rate (%)=100×(Number of dead ticks/Number of tested ticks).

As a result, in the treatment with Compounds of Present Invention 6, 8, 10, 26, 28, 29, 33, 35 and 37, the death rate was 100%.

INDUSTRIAL APPLICABILITY

The compound of the present invention has a controlling effect on pests and is useful as an active ingredient of a pest control agent.

The invention claimed is:
1. A fused heterocyclic compound represented by formula (H-1):

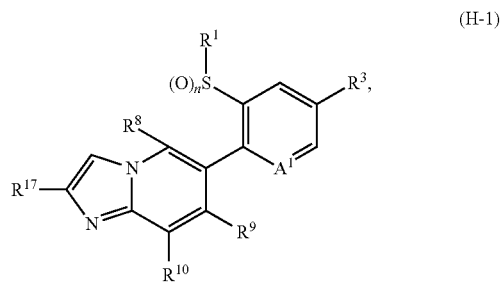

(H-1)

wherein
$A^1$ represents a nitrogen atom or $CR^7$,
$R^1$ represents a C1 to C6 chain hydrocarbon group optionally substituted with one or more atoms or groups selected from group X or a C3 to C6 alicyclic hydrocarbon group optionally substituted with one or more atoms or groups selected from group Y,
$R^3$ and $R^7$ are the same or different and represent a C1 to C6 chain hydrocarbon group optionally substituted with one or more atoms or groups selected from group X, a phenyl group optionally substituted with one or more atoms or groups selected from group Z, a 5- or 6-membered heterocyclic group optionally substituted with one or more atoms or groups selected from group Z, —OR$^{19}$, —S(O)$_m$R$^{19}$, —S(O)$_2$NR$^{19}$R$^{20}$, —NR$^{19}$R$^{20}$, —NR$^{19}$CO$_2$R$^{20}$, —NR$^{19}$C(O)R$^{20}$, —CO$_2$R$^{19}$, —C(O)R$^{19}$, —C(O)NR$^{19}$R$^{20}$, —SF$_5$, a cyano group, a nitro group, a halogen atom or a hydrogen atom,
$R^8$, $R^9$ and $R^{10}$ are the same or different and represent a C1 to C6 chain hydrocarbon group optionally substituted with one or more atoms or groups selected from group X, —OR$^{23}$, —S(O)$_m$R$^{24}$, —S(O)$_2$NR$^{24}$R$^{25}$, —NR$^{24}$R$^{25}$, —NR$^{24}$CO$_2$R$^{25}$, —NR$^{24}$C(O)NR$^{25}$, —CO$_2$R$^{23}$, —C(O)R$^{24}$, —C(O)NR$^{24}$R$^{25}$, —SF$_5$, a cyano group, a nitro group, a halogen atom or a hydrogen atom, R$^{17}$ represents a C1 to C6 chain hydrocarbon group optionally substituted with one or more atoms or groups selected from group X, a phenyl group optionally substituted with one or more atoms or groups selected from group Z, a 5- or 6-membered heterocyclic group optionally substituted with one or more atoms or groups selected from group Z, —OR$^{26}$, —S(O)$_m$R$^{26}$, —S(O)$_2$NR$^{26}$R$^{27}$, —NR$^{26}$R$^{27}$, —NR$^{26}$CO$_2$R$^{27}$, —NR$^{28}$C(O)R$^{29}$, —CO$_2$R$^{26}$, —C(O)R$^{26}$, —C(O)NR$^{26}$R$^{27}$, —SF$_5$, a cyano group, a nitro group, a halogen atom or a hydrogen atom, R$^{19}$, R$^{20}$, R$^{24}$, R$^{25}$, R$^{26}$ and R$^{27}$ are the same or different and represent a C1 to C6 chain hydrocarbon group optionally substituted with one or more atoms or groups selected from group X or a hydrogen atom, R$^{23}$ represents a C1 to C6 chain hydrocarbon group optionally substituted with one or more atoms or groups selected from group X, each m independently represents 0, 1 or 2, and n represents 0, 1 or 2;

wherein when m is 1 or 2 in —S(O)$_m$R$^{24}$, R$^{24}$ does not represent a hydrogen atom, and when m is 1 or 2 in —S(O)$_m$R$^{26}$, R$^{26}$ does not represent a hydrogen atom;

group X is selected from the group consisting of C1 to C6 alkoxy groups optionally substituted with one or more halogen atoms, C2 to C6 alkenyloxy groups optionally substituted with one or more halogen atoms, C2 to C6 alkynyloxy groups optionally substituted with one or more halogen atoms, C1 to C6 alkylsulfanyl groups optionally substituted with one or more halogen atoms, C1 to C6 alkylsulfinyl groups optionally substituted with one or more halogen atoms, C1 to C6 alkylsulfonyl groups optionally substituted with one or more halogen atoms, C2 to C6 alkylcarbonyl groups optionally substituted with one or more halogen atoms, C2 to C6 alkoxycarbonyl groups optionally substituted with one or more halogen atoms, C3 to C6 cycloalkyl groups optionally substituted with one or more halogen atoms or one or more C1 to C3 alkyl groups, cyano groups, hydroxy groups, and halogen atoms, group Y is selected from the group consisting of C1 to C6 chain hydrocarbon groups optionally substituted with one or more halogen atoms, C1 to C6 alkoxy groups optionally substituted with one or more halogen atoms, C2 to C6 alkenyloxy groups optionally substituted with one or more halogen atoms, C2 to C6 alkynyloxy groups optionally substituted with one or more halogen atoms, and halogen atoms, group Z is selected from the group consisting of C1 to C6 chain hydrocarbon groups optionally substituted with one or more halogen atoms, C1 to C6 alkoxy groups optionally substituted with one or more halogen atoms, C1 to C6 alkylsulfanyl groups optionally substituted with one or more halogen atoms, C1 to C6 alkylsulfinyl groups optionally substituted with one or more halogen atoms, C1 to C6 alkylsulfonyl groups optionally substituted with one or more halogen atoms, C2 to C6 alkylcarbonyl groups optionally substituted with one or more halogen atoms, C2 to C6 alkoxycarbonyl groups optionally substituted with one or more halogen atoms, C1 to C6 alkylamino groups optionally substituted with one or more halogen atoms, C2 to C8 dialkylamino groups optionally substituted with one or more halogen atoms, halogen atoms, cyano groups, nitro groups, and SF$_5$.

2. The fused heterocyclic compound according to claim 1, wherein

R$^1$ is a C1 to C6 alkyl group optionally substituted with one or more atoms or groups selected from halogen atoms and cyclopropyl groups (wherein the cyclopropyl group is optionally substituted with one or more halogen atoms or one or more C1 to C3 alkyl groups), a C2 to C6 alkenyl group optionally substituted with one or more halogen atoms, a C2 to C6 alkynyl group optionally substituted with one or more halogen atoms, or a cyclopropyl group optionally substituted with one or more halogen atoms or one or more C1 to C3 alkyl groups, R$^7$ is a halogen atom or a hydrogen atom, R$^3$ is a C1 to C6 alkyl group optionally substituted with one or more halogen atoms, a C2 to C6 alkenyl group optionally substituted with one or more halogen atoms, a C2 to C6 alkynyl group optionally substituted with one or more halogen atoms, a 5- or 6-membered aromatic heterocyclic group (wherein the 5- or 6-membered aromatic heterocyclic group is optionally substituted with one or more atoms or groups selected from the group consisting of halogen atoms, C1 to C3 alkyl groups optionally substituted with a halogen atom, and C1 to C3 alkoxy groups optionally substituted with a halogen atom), —OR$^{19}$ (wherein R$^{19}$ is a C1 to C6 alkyl group optionally substituted with one or more halogen atoms), —S(O)$_m$R$^{19}$ (wherein R$^{19}$ is a C1 to C6 alkyl group optionally substituted with one or more halogen atoms, and m is 0, 1 or 2), —SF$_5$, a cyano group, a nitro group, a halogen atom or a hydrogen atom, R$^8$, R$^9$ and R$^{10}$ are the same or different and are a C1 to C6 alkyl group optionally substituted with one or more halogen atoms, —NR$^{24}$R$^{25}$ (wherein R$^{24}$ and R$^{25}$ are the same or different and are a C1 to C6 alkyl group optionally substituted with one or more halogen atoms or a hydrogen atom), a halogen atom or a hydrogen atom, R$^{17}$ is a C1 to C6 alkyl group optionally substituted with one or more halogen atoms, —OR$^{26}$ (wherein R$^{26}$ is a C1 to C6 alkyl group optionally substituted with one or more halogen atoms), —S(O)$_m$R$^{26}$ (wherein R$^{26}$ is a C1 to C6 alkyl group optionally substituted with one or more halogen atoms, and m is 0, 1 or 2), —SF$_5$ or a halogen atom.

3. The fused heterocyclic compound according to claim 1, wherein

R$^1$ is an ethyl group, a cyclopropyl group or a cyclopropylmethyl group,

R$^7$ is a hydrogen atom,

R$^3$ is a C1 to C6 alkyl group optionally substituted with one or more halogen atoms, —OR$^{19}$ (wherein R$^{19}$ is a C1 to C6 alkyl group optionally substituted with one or more halogen atoms), —S(O)$_m$R$^{19}$ (wherein R$^{19}$ is a C1 to C6 alkyl group optionally substituted with one or more halogen atoms, and m is 0, 1 or 2), a halogen atom or a hydrogen atom, R$^8$, R$^9$ and R$^{10}$ are the same or different and are a methyl group, a halogen atom or a hydrogen atom, R$^{17}$ is a C1 to C6 haloalkyl group, —OR$^{26}$ (wherein R$^{26}$ is a C1 to C6 haloalkyl group), —S(O)$_m$R$^{26}$ (wherein R$^{26}$ is a C1 to C6 haloalkyl group, and m is 0, 1 or 2), or a halogen atom.

4. A pest control composition comprising the fused heterocyclic compound as defined in claim 1, and an inert carrier.

5. A method for controlling pests comprising applying an effective amount of the fused heterocyclic compound as defined in claim 1 to a pest or a pest-infested area.

6. The fused heterocyclic compound according to claim 1, wherein $A^1$ is a nitrogen atom.

7. The fused heterocyclic compound according to claim 1, wherein $A^1$ is $CR^7$.

* * * * *